United States Patent
Schoeberl et al.

(10) Patent No.: US 8,961,966 B2
(45) Date of Patent: *Feb. 24, 2015

(54) ANTIBODIES AGAINST ERBB3 AND USES THEREOF

(75) Inventors: Birgit Schoeberl, Cambridge, MA (US); Ulrik Nielsen, Quincy, MA (US); Michael Feldhaus, Grantham, NH (US); Arumugam Muruganandam, Bangalore (IN); David Buckler, Chester, NJ (US)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 1155 days.

This patent is subject to a terminal disclaimer.

(21) Appl. No.: 12/904,492

(22) Filed: Oct. 14, 2010

(65) Prior Publication Data

US 2011/0123523 A1 May 26, 2011

Related U.S. Application Data

(63) Continuation of application No. 12/425,874, filed on Apr. 17, 2009, now abandoned, which is a continuation-in-part of application No. 12/281,925, filed as application No. PCT/US2008/002119 on Feb. 15, 2008, now Pat. No. 7,846,440.

(60) Provisional application No. 60/901,904, filed on Feb. 16, 2007, provisional application No. 61/009,796, filed on Jan. 2, 2008.

(51) Int. Cl.
  *A61K 39/395* (2006.01)
  *C07K 16/00* (2006.01)
  *C07K 16/28* (2006.01)
  *C07K 16/32* (2006.01)
  *A61K 31/337* (2006.01)
  *A61K 31/517* (2006.01)
  *A61K 33/24* (2006.01)
  *A61K 39/00* (2006.01)

(52) U.S. Cl.
  CPC ............ *C07K 16/2863* (2013.01); *C07K 16/32* (2013.01); *A61K 31/337* (2013.01); *A61K 31/517* (2013.01); *A61K 33/24* (2013.01); *A61K 39/3955* (2013.01); *A61K 39/39558* (2013.01); *A61K 2039/505* (2013.01); *C07K 2316/96* (2013.01); *C07K 2317/21* (2013.01); *C07K 2317/55* (2013.01); *C07K 2317/92* (2013.01)
  USPC .................. 424/133.1; 424/143.1; 530/387.3; 530/388.1

(58) Field of Classification Search
  USPC .............. 424/133.1, 143.1; 530/387.3, 388.1
  See application file for complete search history.

(56) References Cited

U.S. PATENT DOCUMENTS

| | | |
|---|---|---|
| 5,344,760 A | 9/1994 | Harvey et al. |
| 5,480,968 A | 1/1996 | Kraus et al. |
| 5,968,511 A | 10/1999 | Akita et al. |
| 6,696,290 B2 | 2/2004 | Fitzpatrick et al. |
| 6,983,227 B1 | 1/2006 | Thalhammer-Reyero |
| 7,097,840 B2 | 8/2006 | Erickson et al. |
| 7,125,680 B2 | 10/2006 | Singer et al. |
| 7,285,649 B2 | 10/2007 | Akita et al. |
| 7,846,440 B2 * | 12/2010 | Schoeberl et al. ......... 424/141.1 |
| 2002/0001587 A1 | 1/2002 | Erickson et al. |
| 2002/0002276 A1 | 1/2002 | Fitzpatrick et al. |
| 2002/0119148 A1 | 8/2002 | Gerritsen et al. |
| 2002/0165193 A1 | 11/2002 | Greene et al. |
| 2003/0040605 A1 | 2/2003 | Siegel |
| 2003/0199020 A1 | 10/2003 | Fitzpatrick et al. |
| 2004/0052786 A1 | 3/2004 | Gerritsen et al. |
| 2004/0071696 A1 | 4/2004 | Adams et al. |
| 2004/0082510 A1 | 4/2004 | Ullrich et al. |
| 2004/0138417 A1 | 7/2004 | Fitzpatrick et al. |
| 2004/0197332 A1 | 10/2004 | Ullrich et al. |
| 2004/0229380 A1 | 11/2004 | Chan-Hui et al. |
| 2004/0248151 A1 | 12/2004 | Bacus et al. |
| 2004/0248196 A1 | 12/2004 | Adams et al. |
| 2005/0004018 A1 | 1/2005 | Jimeno et al. |
| 2005/0079184 A1 | 4/2005 | Hsing-Chang et al. |
| 2005/0187745 A1 | 8/2005 | Lurie et al. |
| 2005/0267720 A1 | 12/2005 | Hill et al. |
| 2006/0040363 A1 | 2/2006 | Kucherlapati et al. |
| 2006/0093603 A1 | 5/2006 | Gerritsen et al. |
| 2006/0136139 A1 | 6/2006 | Elcock et al. |
| 2006/0167637 A1 | 7/2006 | Agur et al. |
| 2006/0204505 A1 | 9/2006 | Sliwkowski et al. |

(Continued)

FOREIGN PATENT DOCUMENTS

| | | |
|---|---|---|
| EP | 1058562 B1 | 12/2000 |
| EP | 1187634 B1 | 3/2002 |
| EP | 1283053 A1 | 2/2003 |
| EP | 1728802 A2 | 12/2006 |
| WO | 97/35885 A1 | 10/1997 |
| WO | 98/02540 A1 | 1/1998 |
| WO | 99/54800 A2 | 10/1999 |
| WO | 99/60023 A1 | 11/1999 |
| WO | 00/78347 A1 | 12/2000 |
| WO | 02/060470 A1 | 8/2002 |

(Continued)

OTHER PUBLICATIONS

Lederman et al (Molecular Immunology 28:1171-1181, 1991).*

(Continued)

*Primary Examiner* — Lynn Bristol
(74) *Attorney, Agent, or Firm* — Nelson Mullins Riley & Scarborough LLP; Jane E. Remillard, Esq.; Jill Gorny Sloper, Esq.

(57) ABSTRACT

The present invention provides a novel class of monoclonal antibodies which bind ErbB3 receptor and inhibits various ErbB3 functions. For example, the antibodies described herein are capable of binding to ErbB3 and inhibiting EGF-like ligand mediated phosphorylation of the receptor.

15 Claims, 54 Drawing Sheets

(56) References Cited

U.S. PATENT DOCUMENTS

| | | |
|---|---|---|
| 2006/0210561 A1 | 9/2006 | Baughman et al. |
| 2007/0059785 A1 | 3/2007 | Bacus et al. |
| 2007/0081994 A1 | 4/2007 | Fitzpatrick et al. |
| 2007/0092513 A1 | 4/2007 | Gerritsen et al. |
| 2007/0122407 A1 | 5/2007 | Akita et al. |
| 2007/0134251 A1 | 6/2007 | Ashkenazi et al. |
| 2007/0134252 A1 | 6/2007 | Bacus et al. |
| 2007/0190583 A1 | 8/2007 | Spector et al. |
| 2007/0254295 A1 | 11/2007 | Harvey et al. |
| 2008/0026415 A1 | 1/2008 | Rimm et al. |
| 2008/0057064 A1 | 3/2008 | Zhou |
| 2008/0090233 A1 | 4/2008 | Garcia et al. |
| 2008/0112958 A1 | 5/2008 | Mass |
| 2008/0124334 A1 | 5/2008 | Akita et al. |
| 2008/0124345 A1 | 5/2008 | Rothe et al. |
| 2008/0187948 A1 | 8/2008 | Chan-Hui et al. |
| 2008/0207615 A1 | 8/2008 | Bell et al. |
| 2008/0214584 A1 | 9/2008 | Ohta et al. |
| 2008/0254497 A1 | 10/2008 | Singh |
| 2009/0181022 A1 | 7/2009 | Nielsen et al. |
| 2009/0246206 A1 | 10/2009 | Nielsen et al. |
| 2009/0291085 A1 | 11/2009 | Schoeberl et al. |
| 2011/0027291 A1 | 2/2011 | Schoeberl et al. |
| 2011/0123523 A1 | 5/2011 | Schoeberl et al. |

FOREIGN PATENT DOCUMENTS

| | | |
|---|---|---|
| WO | 03/012072 A2 | 2/2003 |
| WO | 03/013602 A1 | 2/2003 |
| WO | 2004/003019 A3 | 1/2004 |
| WO | 2005/017493 A2 | 2/2005 |
| WO | 2006/017538 A2 | 2/2006 |
| WO | 2006/020706 A2 | 2/2006 |
| WO | 2006/044748 A2 | 4/2006 |
| WO | 2006/091209 A2 | 8/2006 |
| WO | 2007/015935 A2 | 2/2007 |
| WO | 2007/039705 A1 | 4/2007 |
| WO | 2007/041502 A2 | 4/2007 |
| WO | 2007/077028 A2 | 7/2007 |
| WO | 2007/115571 A2 | 10/2007 |
| WO | 2007/130677 A2 | 11/2007 |
| WO | 2008/064884 A1 | 6/2008 |
| WO | 2008/100624 A2 | 8/2008 |
| WO | 2008/109440 A2 | 9/2008 |
| WO | 2010/019952 A2 | 2/2010 |

OTHER PUBLICATIONS

Li et al (Proc. Natl. Acad. Sci. USA 77:3211-3214, 1980).*
Brummell et al. (Biochemistry 32:1180-1187 (1993)).*
Kobayashi et al. (Protein Engineering 12:879-844 (1999)).*
Burks et al. (Pnas 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Dufner (Trends Biotechnol. 24(11):523-29 (2006)).*
Aaronson, S.A. et al., "Growth factor-regulated pathways in epithelial cell proliferation," Am. Rev. Respir. Dis., vol. 142(6 pt. 2):S7-S10 (1990).
Alberts, Bruce et al., Molecular Biology of the Cell, Third Edition, Garland Publishing, Inc., New York, pp. 897-899 (1994).
Alimandi, Maurizio et al., "Cooperative signaling of ErbB3 and ErbB2 in neoplastic transformation and human mammary carcinomas," Oncogene, vol. 10:1813-1821 (1995).
Alimandi, Maurizio et al., "Epidermal growth factor and betacellulin mediate signal transduction through co-expressed ErbB2 adn ErbB3 receptors," The EMBO Journal, vol. 16(18):5608-5617 (1997).
Balint, Robert F. et al., "Antibody engineering by parsimonious mutagenesis," Gene, vol. 137:109-118 (1993).
Becerril, Baltazar et al., "Toward Selection of Internalizing Antibodies from Phage Libraries," Biochemical and Biophysical Research Communications, vol. 255:386-393 (1999).
Beerli, Roger R. et al., "Neu Differentiation Factor Activation of ErbB-3 and ErbB-4 Is Cell Specific and Displays a Differential Requirement for ErbB-2," Molecular and Cellular Biology, vol. 15(12):6496-6505 (1995).
Bodey, Bela et al., "Immunophenotypically Varied Cell Subpopulations in Primary and Metastatic Human Melanomas. Monoclonal Antibodies for Diagnosis, Detection of Neoplastic Progression and Receptor Directed Immunotherapy," Anticancer Research, vol. 16:517-532 (1996).
Bortoletto, Nicola et al., "Optimizing anti-CD3 affinity for effective T cell targeting against tumor cells," Eur. J. Immunol., vol. 32:3102-3107 (2002).
Bostwick, David G., "c-erbB-2 Oncogene Expression in Prostatic Intraepithelial Neoplasia: Mounting Evidence for a Precursor Role," Journal of the National Cancer Institute, vol. 86(15):1108-1110 (1994).
Brotherick, Ian et al., "A flow cytometric study of c-erbB-3 expression in breast cancer," Cancer Immunol. Immunother., vol. 41:280-286 (1995).
Carraway, Kermit L. III et al., "A Neu Acquaintance for ErbB3 and ErbB4: A Role for the Receptor Heterodimerization in Growth Signaling," Cell, vol. 78:5-8 (1994).
Carraway, Kermit L. III et al., "Heregulin Stimulates Mitogenesis and Phosphatidylinositol 3-Kinase in Mouse Fibroblasts Transfected with erbB2/neu and erbB3," The Journal of Biological Chemistry, vol. 270(13):7111-7116 (1995).
Carraway, Kermit L. III et al., "The erbB3 Gene Product Is a Receptor for Heregulin," The Journal of Biological Chemistry, vol. 269(19):14303-14306 (1994).
Chen, Xiaomei et al., "An Immunological Approach Reveals Biological Differences between the Two NDF/Heregulin Receptors, ErbB-3 and ErbB-4," The Journal of Biological Chemistry, vol. 271(13):7620-7629 (1996).
Ciardiello, Fortunato et al., "Differential expression of epidermal growth factor-related proteins in human colorectal tumors," Proc. Natl. Acad. Sci. USA, vol. 88:7792-7796 (1991).
Davies, Jullian et al., "Affinity improvement of single antibody VH domains: residues in all three hypervariable regions affect antigen binding," Immunotechnology, vol. 2:169-179 (1996).
Di Fiore, Pier Paolo et al., "Mechanisms involving an expanding erbB/EGF receptor family of tyrosine kinases in human neoplasia," Genes, Oncogenes, and Hormones, Robert B. Dickson, Ed., Kluwer Academic Publishers, pp. 139-160 (1992).
Dorvillius, Mylene et al., "Targeting of Human Breast Cancer by a Bispecific Antibody Directed against Two Tumour-Associated Antigens: ErbB-2 and Carcinoembryonic Antigen," Tumor Biol., vol. 23:337-347 (2002).
Drebin, Jeffrey A. et al., "Monoclonal antibodies reactive with distinct domains of the neu oncogene-encoded p185 molecule exert synergistic anti-tumor effects in vivo," Oncogene, vol. 2:273-277 (1988).
Eccles, Suzanne A. et al., "Significance of the c-erbB Family of Receptor Tyrosine Kinases in Metastatic Cancer and Their Potential as Targets for Immunotherapy," Invasion Metastasis, vol. 14:337-348 (1995).
Ethier, Stephen P. et al., "erbB Family Receptor Expression and Growth Regulation in a Newly Isolated Human Breast Cancer Cell Line," Cancer Research, vol. 56:899-907 (1996).
Faksvag, Dagny R. et al., "Expression of c-erbB-3 and c-erbB-4 Proteins in Papillary Thyroid Carcinomas," Cancer Research, vol. 56:1184-1188 (1996).
Fendly, Brian M. et al., "Characterization of Murine Monoclonal Antibodies Reactive to Either the Human Epidermal Growth Factor Receptor or HER2/neu Gene Product," Cancer Research, vol. 50:1550-1558 (1990).
Fiddes, Rodney J. et al., "Heregulin (HRG)-induced Mitogenic Signaling and Cytotoxic Activity of a HRG/PE40 Ligand Toxin in Human Breast Cancer Cells," Cell Growth & Differentiation, vol. 6:1567-1577 (1995).
Fitzpatrick, V. Danial et al., "Formation of a high affinity heregulin binding site using the soluble extracellular domains of ErbB2 with ErbB3 or ErbB4," FEBS Letters, vol. 431:102-106 (1998).

(56) References Cited

OTHER PUBLICATIONS

Francois, Christine et al., "Antibodies directed at mouse IL-2-R a and b chains act in synergy to abolish T-cell proliferation in vitro and delayed type hypersensitivity reaction in vivo," Transpl. Int., vol. 9:46-50 (1996).
Friess, Helmut et al., "Enhanced erbB-3 Expression in Human Pancreatic Cancer Correlates with Tumor Progression," Clinical Cancer Research, vol. 1:1413-1420 (1995).
Friess, H. et al., "Pancreatic cancer: the potential clinical relevance of alterations in growth factors and their receptors," J. Mol. Med., vol. 74:35-42 (1996).
Fuchs, C.S., "Gastric Carcinoma," The New England Journal of Medicine, vol. 333(21):1426-1428 (1995).
Gamett, Daniel C. et al., "Heregulin-stimulated Signaling in Rat Pheochromocytoma Cells," The Journal of Biological Chemistry, vol. 270(32):19022-19027 (1995).
Gorgoulis, V. et al., "Molecular and immunohistochemical study of class I growth factor receptors in squamous cell lung carcinomas," Abstracts / Lung Cancer, vol. 14:381 (1996).
Grasso, Adam W. et al., "ErbB kinases and NDF signaling in human prostate cancer cells," Oncogene, vol. 15:2705-2716 (1997).
Gullick, W.J., "The c-erbB3/HER3 Receptor in Human Cancer," Cancer Surveys, vol. 27:339-349 (1996).
Guy, Pamela M. et al., "Insect cell-expressed p180erbB3 possesses an impaired tyrosine kinase activity," Proc. Natl. Acad. Sci. USA, vol. 91:8132-8136 (1994).
Heldin, Carl-Henrik, "Dimerization of Cell Surface Receptors in Signal Transduction," Cell, vol. 80:213-223 (1995).
Hellyer, Nathan J. et al., "Cloning of the rat ErbB3 cDNA and characterization of the recombinant protein," Gene, vol. 165:279-284 (1995).
Hofmann, Francesco et al., "Blocking insulin-like growth factor-I receptor as a strategy for targeting cancer," DDT, vol. 10(15):1041-1047 (2005).
Holmes, William E. et al., "Identification of Heregulin, a Specific Activator of p185erbB2," Science, vol. 256:1205-1210 (1992).
Holt, Lucy J. et al., "Domain antibodies: proteins for therapy," TRENDS in Biotechnology, Vo. 21(11):484-490 (2003).
Horan, Thomas et al., "Binding of Neu Differentiation Factor with the Extracellular Domain of Her2 and Her3," The Journal of Biological Chemistry, vol. 270(40):24604-24608 (1995).
Hsieh, AC et al., "Targeting HER proteins in cancer therapy and the role of the non-target HER3," British Journal of Cancer, vol. 97:453-457 (2007).
Htun Van Der Horst, Edward et al., "Anti-HER-3 MAbs Inhibit HER-3-Mediated Signaling in Breast Cancer Cell Lines Resistant to Anti-HER-2 Antibodies," Int. J. Cancer, vol. 115:519-527 (2005).
Information Disclosure Submission concerning Agreement between Dyax Corporation and Merrimack Pharmaceuticals.
Issing, W.J. et al., "erbB-3, a third member of the erbB/epidermal growth factor receptor gene family: its expression in head and neck cancer cell lines," Eur. Arch. Otorhinolaryngol, vol. 250:392-395 (1993).
Jeschke, Margit et al., "Targeted Inhibition of Tumor-cell Growth by Recombinant Heregulin-toxin Fusion Proteins," Int. J. Cancer, vol. 60:730-739 (1995).
Jo, Sangmee Ahn et al., "Neuregulins are concentrated at nerve-muscle synapses and activate ACh-receptor gene expression," Nature, vol. 373:158-161 (1995).
Jones, Jennifer T. et al., "Binding specificities and affinities of egf domains for ErbB receptors," FEBS Letters, vol. 447:227-231 (1999).
Karunagaran, Devarajan et al., "ErbB-2 is a common auxiliary subunit of NDF and EGF receptors: implications for breast cancer," The EMBO Journal, vol. 15(2):254-264 (1996).
Kasprzyk, Philip G. et al., "Therapy of an Animal Model of Human Gastric Cancer Using a Combination of Anti-erbB-2 Monoclonal Antibodies," Cancer Research, vol. 52:2771-2776 (1992).

Lee, Hakjoo et al., "A Naturally Occurring Secreted Human ErbB3 Receptor Isoform Inhibits Heregulin-stimulated Activation of ErbB2, ErbB3, and ErbB4,"Cancer Research, vol. 61:4467-4473 (2001).
Lee, Hakjoo et al., "Isolation and characterization of four alternate c-erbB3 transcripts expressed in ovarian carcinoma-derived cell lines and normal human tissues," Oncogene, vol. 6:3243-3252 (1998).
Lemoine, Nicholas R. et al.,"The erbB-3 Gene in Human Pancreatic Cancer," Journal of Pathology, vol. 168:269-273 (1992).
Levi, Allan D.O. et al., "The Influence of Heregulins on Human Schwann Cell Proliferation," The Journal of Neuroscience, vol. 15(2):1329-1340 (1995).
Lewis, Gail D. et al., "Growth Regulation of Human Breast and Ovarian Tumor Cells by Herebulin: Evidence for the Requirement of ErbB2 as a Critical Component in Mediating Heregulin Responsiveness," Cancer Research, vol. 56:1457-1465 (1996).
Little, M. et al., "Of mice and men: hybridoma and recombinant antibodies," Immunology Today, vol. 21(8):364-370 (2000).
Lu, Dan et al., "Complete Inhibition of Vascular Endothelial Growth Factor (VEGF) Activities with a Bifunctional Diabody Directed against Both VEGF Kinase Receptors, fms-like Tyrosine Kinase Receptor and Kinase Insert Domain-containing Receptor," Cancer Research, vol. 61:7002-7008 (2001).
Marchionni, Mark A. et al., "Glial growth factors are alternatively spliced erbB2 ligands expressed in the nervous system," Nature, vol. 362:312-318 (1993).
Marte, Barbara M. et al., "Neu Differentiation Factor/Heregulin Modulates Growth and Differentiation of HC11 Mammary Epithelial Cells," Molecular Endocrinology, vol. 9:14-23 (1995).
McCall, Adrian M. et al., "Increasing the Affinity for Tumor Antigen Enhances Bispecific Antibody Cytotoxicity," The Journal of Immunology, vol. 166:6112-6117 (2001).
Morrissey, Thomas K. et al., "Axon-induced mitogenesis of human Schwann cell involves heregulin and p185erbB2," Proc. Natl. Acad. Sci. USA, vol. 92:1431-1435 (1995).
Moscosco, Lisa M. et al., "Synapse-Associated Expression of an Acetylcholine Receptor-Inducing Protein, ARIA/Heregulin, and Its Putative Receptors, ErbB2 and ErbB3, in Developing Mammalian Muscle," Developmental Biology, vol. 172:158-169 (1995).
Myers, Russell B. et al., "Expression of p160erbB-3 and p185erbB-2 in Prostatic Intraepithelial Neoplasia and Prostatic Adenocarcinoma," Journal of the National Cancer Institute, vol. 86(15):1140-1145 (1994).
Nielsen, Ulrik B. et al., "Targeting of Bivalent Anti-ErbB2 Diabody Antibody Fragments to Tumor Cells Is Independent of the Intrinsic Antibody Affinity," Cancer Research, vol. 60:6434-6440 (2000).
Oikawa, Tetsuro et al., "Frequent Expression of Genes for Receptor Tyrosine Kinases and Their Ligands in Human Pancreatic Cancer Cells," International Journal of Pancreatology, vol. 18(1):15-23 (1995).
Orr-Urtreger, Avi et al., "Neural expression and chromosomal mapping of Neu differentiation factor to 8 p. 12-p. 21," Proc. Natl. Acad. Sci. USA, vol. 90:1867-1871 (1993).
Peles, Elior et al., "Cell-type specific interaction of Neu differentiation factor (NDF/heregulin) with Neu/HER-2 suggests complex ligand-receptor relationships," The EMBO Journal, vol. 12(3):961-971 (1993).
Pierce, Jacalyn H. et al., "Signal Transduction Through the EGF Receptor Transfected in IL-3-Dependent Hematopoietic Cells," Science, vol. 239:628-631 (1988).
Pinkas-Kramarski, Ronit et al., "Diversification of Neu differentiation factor and epidermal growth factor signaling by combinatorial receptor interactions," The EMBO Journal, vol. 15(10):2452-2467 (1996).
Pinkas-Kramarski, Ronit et al., "Neu Differentiation Factor/ Neuregulin Isoforms Activate Distinct Receptor Combinations," The Journal of Biological Chemistry, vol. 271(32):19029-19032 (1996).
Pinkas-Kramarski, Ronit et al., "The oncogenic ErbB-2/ErbB-3 heterdimer is a surrogate receptor of the epidermal growth factor and betacellulin," Oncogene, vol. 16:1249-1258 (1998).
Plowman, Gregory D. et al., "Heregulin induces tyrosine phosphorylation of HER4/p180erbB4," Nature, vol. 366:473-475 (1993).

(56) References Cited

OTHER PUBLICATIONS

Plowman, Gregory D. et al., "Ligand-specific activation of HER4/p180erbB4, a fourth member of the epidermal growth factor receptor family," Proc. Natl. Acad. Sci. USA, vol. 90:1746-1750 (1993).
Plowman, Gregory D. et al., "Molecular cloning and expression of an additional epidermal growth factor receptor-related gene," Proc. Natl. Acad. Sci. USA, vol. 87:4905-4909 (1990).
Poller, D.N. et al., "Production and Characterization of a Polyclonal Antibody to the c-erbB-3 Protein: Examination of c-erbB-3 Protein Expression in Adenocarcinomas," Journal of Pathology, vol. 168:275-280 (1992).
Presta, Leonard, "Antibody engineering for therapeutics," Current Opinion in Structural Biology, vol. 13:519-525 (2003).
Prigent, S.A. et al., "Expression of the c-erbB-3 protein in normal human adult and fetal tissues," Oncogene, vol. 7:1273-1278 (1992).
Prigent, Sally A. et al., "The Type 1 (EGFR-related) Family of Growth Factor Receptors and Their Ligands," Progress in Growth Factor Research, vol. 4:1-24 (1992).
Quinn, C.M. et al., "c-erbB-3 protein expression in human breast cancer: comparison with othe tumour variables and survival," Histopathology, vol. 25:247-252 (1994).
Rajkumar, T. et al., "A monoclonal antibody to the human c-erbB3 protein stimulates the anchorage-independent growth of breast cancer cell lines," Br. J. Cancer, vol. 70:459-465 (1994).
Rajkumar, Thangarajan et al., "Experssion of the C-erbB-3 Protein in Gastrointestinal Tract Tumours Determined by Monoclonal Antibody RTJ1," Journal of Pathology, vol. 170:271-278 (1993).
Rajkumar, T. et al., "Prevalence of c-erbB3 expression in squamous cell carcinomas of the cervix as determined by the monoclonal antibody RTJ2," International Journal of Oncology, vol. 6:105-109 (1995).
Rajkumar, Thangarajan et al., "The Type I growth factor receptors in human breast cancer," Breast Cancer Research and Treatment, vol. 29:3-9 (1994).
Ross, Jeffrey S. et al., "The HER-2/neu Oncogene in Breast Cancer: Prognostic Factor, Predictive Factor, and Target for Therapy," The Oncologist, vol. 3:237-252 (1998).
Sadick, Michael D. et al., "Analysis of Heregulin-Induced ErbB2 Phosphorylation wtih a High-Throughput Kinase Receptor Activation Enzyme-Linked Immunosorbant Assay," Analytical Biochemistry, vol. 235:207-214 (1996).
Salomon, David S. et al., "Epidermal growth factor-related peptides and their receptors in human malignancies," Critical Reviews in Oncology/Hematology, vol. 19:183-232 (1995).
Sanidas, E.E. et al., "Expression of the c-erbB-3 Gene Product in Gastric Cancer," Int. J. Cancer, vol. 54:935-940 (1993).
Schaefer, Karl-Ludwig et al., "Constitutive Activation of Neuregulin/ERBB3 Signaling Pathway in Clear Cell Sarcoma of Soft Tissue," Neoplasia, vol. 8(7):613-622 (2006).
Schaefer, Karl-Ludwig et al., "Expression Profiling of t(12;22) Positive Clear Cell Sarcoma of Soft Tissue Cell Lines Reveals Characteristic Up-Regulation of Potential New Marker Genes Including ERBB3," Cancer Research, vol. 64:3395-3405 (2004).
Baselga, Jose et al., "Novel anticancer targets: revisiting ERBB2 and discovering ERBB3," Nature Reviews Cancer, vol. 9(7):463-475 (2009).
Campbell, Marcia R. et al., "NER3 Comes of Age: New Insights into the Functions and Role in Signaling, Tumor Biology, and Cancer Therapy," Clin. Cancer Res., vol. 16(5):1373-1383 (2010).
Erjala, Kaisa et al., "Signaling via ErbB2 and ErbB3 Associates with Resistance and Epidermal Growth Factor Receptor (EGFR) Amplification with Sensitivity to EGFR Inhibitor Gefitinib in Head and Neck Squamous Cell Carcinoma Cells," Clin. Cancer Res., vol. 12(13):4103-4111 (2006).
Foley, John et al., "EGFR Signaling in Breast Cancer: Bad to the Bone," Semin. Cell Dev. Biol., vol. 21(9):951-960 (2010).
Harris, Lyndsay N. et al., "Molecular subtypes of breast cancer in relation to paclitaxel response and outcomes in women with metastatic disease: results from CALGB 9342," Breast Cancer Research, vol. 8(6):R66, 12 pp. doi: 10.1186/bcr1622 (2006).

Lee-Hoeflich, Si Tuen et al., "A Central Role for HER3 in HER2-Amplified Breast Cancer: Implications for Targeted Therapy," Cancer Res., vol. 68(14):5878-5887 (2008).
Nie, Lin et al., "Efficacy of MM121 in ER+ and triple negative breast cancer studies," Proceedings of the American Association for Cancer Research, vol. 51:436, Poster Presentation No. 1806 (2010).
Schneider, Bryan P. et al., "Triple-Negative Breast Cancer: Risk Factors to Potential Targets," Clin. Cancer Res., vol. 14(24):8010-8018 (2008).
Schoeberl, Birgit et al., "An ErbB3 Antibody, Mm-121, Is Active in Cancers with Ligand-Dependent Activation," Cancer Res., vol. 70(6):2485-2494 (2010).
Schoeberl, Birgit et al., "Computational modeling and simulation lead to the development of MM-121, a human monoclonal antibody ErbB3 antagonist," 99th AACR Annual Meeting, Poster Presentation Abstract No. 1638 (2008).
Schoeberl, Birgit et al., "MM-121:a human monoclonal antibody ErbB3 antagonist," 99th AACR Annual Meeting, Poster Presentation Abstract No. 3974 (2008).
International Preliminary Report on Patentability for Application No. PCT/US2009/054051, dated Feb. 15, 2011.
International Search Report and Written Opinion for Application No. PCT/US20091054051, dated May 4, 2010.
International Search Report for Application No. PCT/US2011/028129, 4 pages, dated Oct. 13, 2011.
International Preliminary Report on Patentability and Written Opinion for Application No. PCT/US2011/028129, 8 pages, dated Sep. 11, 2012.
ATCC, "AdrR," retrieved online at: http://www.atcc.org/ATCCAdvancedCatalogSearch/AllCollectionSearch/tabid/454/Default.aspx (2011).
Beckman, Robert A. et al., "Antibody Constructs in Cancer Therapy, Protein Engineering Strategies to Improve Exposure in Solid Tumors," Cancer, vol. 109:170-179 (2007).
Casset, Florence et al., "A peptide mimetic of an anti-CD4 monoclonal antibody by rational design," Biochemical and Biophysical Research Communications, vol. 307:198-205 (2003).
Cespedes, Maria Virtudes et al., "Mouse models in oncogenesis and cancer therapy," Clin. Transl. Oncol., vol. 8 (5):318-329 (2006).
Chen, Yvonne et al., "Selection and Analysis of an Optimized Anti-VEGF Antibody: Crystal Structure of an Affinity-matured Fab in Complex with Antigen," J. Mol. Biol., vol. 293:865-881 (1999).
De Pascalis, Roberto et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, vol. 169:3076-3084 (2002).
Dennis, Carina, "OFf by a whisker," Nature, vol. 442:739-741 (2006).
Fujimori, Kenji et al., "A Modeling Analysis of Monoclonal Antibody Percolation Through Tumors: A Binding-Site Barrier," J. Nucl. Med., vol. 31:1191-1198 (1990).
Holm, Patrik et al., "Functional mapping and single chain construction of the anti-cytokeratin 8 monoclonal antibody TS1," Molecular Immunology, vol. 44:1075-1084 (2007).
Kumar, Sanjeev et al., "Molecular Cloning and Expression of the Fabs of Human Autoantibodies in *Escherichia coli*," The Journal of Biological Chemistry, vol. 275(45):35129-35136 (2000).
MacCallum, Robert M. et al., "Antibody-antigen Interactions: Contact Analysis and Binding Site Topography," J. Mol. Biol., vol. 262:732-745 (1996).
Rudikoff, Stuart et al., "Single amino acid substitution altering antigen-binding specificity," Proc. Natl. Acad. Sci. USA, vol. 79:1979-1983 (1982).
Rudnick, Stephen I. et al., "Affinity and Avidity in Antibody-Based Tumor Targeting," Cancer Biotherapy and Radiopharmaceuticals, vol. 24(2):155-161 (2009).
Smith-Gill, Sandra J. et al., "Contributions of Immunoglobulin Heavy and Light Chains to Antibody Specificity for Lysozyme and Two Haptens," The Journal of Immunology, vol. 139:4135-4144 (1987).

(56) References Cited

OTHER PUBLICATIONS

Song, Mi-Kyung et al., "Light Chain of Natural Antibody Plays a Dominant Role in Protein Antigen Binding," Biochemical and Biophysical Research Communications, vol. 268:390-394 (2000).
Thurber, Greg M. et al., "Antibody tumor penetration: Transport opposed by systemic and antigen-mediated clearance," Advanced Drug Delivery Reviews, vol. 60:1421-1434 (2008).
Vajdos, Felix F. et al., "Comprehensive Functional Maps of the Antigen-binding Site of an Anti-ErbB2 Antibody Obtained with Shotgun Scanning Mutagenesis," J. Mol. Biol., vol. 320:415-428 (2002).
Voskoglou-Nomikos, Theodora et al., "Clinical Predictive Value of the in Vitro Cell Line, Human Xenograft, and Mouse Allograft Preclinical Cancer Models," Clinical Cancer Research, vol. 9:4227-4239 (2003).
Ward, E. Sally et al., "Binding activities of a repertoire of single immunoglobulin variable domains secreted from *Escherichia coli*," Nature, vol. 341:544-546 (1989).
Wu, Herren et al., "Humanization of a Murine Monoclonal Antibody by Simultaneous Optimization of Framework and CDR Residues," J. Mol. Biol., vol. 294:151-162 (1999).
Katoh, Masaru et al., "c-erbB3 Gene Encodes Secreted as Well as Transmembrane Receptor Tyrosine Kinase," Biochemical and Biophysical Research Communications, vol. 192(3):1189-1197 (1993).
Kim, Hong-Hee et al., "Epidermal Growth Factor-dependent Association of Phosphatidylinositol 3-Kinase with the erbB3 Gene Product," The Journal of Biological Chemistry, vol. 269(40):24747-24755 (1994).
Kim, Hong-Hee et al., "Signal transduction by epidermal growth factor and heregulin via the kinase-deficient ErbB3 protein," Biochem. J., vol. 334:189-195 (1998).
Kinugasa, Yumi et al., "Neuroglycan C, a novel member of the neuregulin family," Biochemical and Biophysical Research Communications, vol. 321:1045-1049 (2004).
Kita, Yoshiko et al., "Bioactive Synthetic Peptide of NDF/Heregulin," Biochemical and Biophysical Research Communicatnions, vol. 210(2):441-451 (1995).
Kita, Yoshiko A. et al., "NDF/heregulin stimulates the phosphorylation of Her3/erbB3," FEBS Letters, vol. 349:139-143 (1994).
Klapper, Leah N. et al., "A subclass of tumor-inhibitory monoclonal antibodies to ErbB-2/HER2 blocks crosstalk with growth factor receptors," Oncogene, vol. 14:2099-2109 (1997).
Korabiowska, Monika et al., "Differential Expression of cerbB3 in Naevi and Malignant Melanomas," Anticancer Research, vol. 16:471-474 (1996).
Kraus, Matthias H. et al., "Demonstration of ligand-dependent signaling by the erbB-3 tyrosine kinase and its constitutive activation in human breast tumor cells," Proc. Natl. Acad. Sci. USA, vol. 90:2900-2904 (1993).
Kraus, Matthias H. et al., "Isolation and characterization of ERBB3, a third member of the ERBB/epidermal growth factor receptor family: Evidence for overexpression in a dubset of human mammary tumors," Proc. Natl. Acad. Sci. USA, vol. 86:9193-9197 (1989).
Kraus, Matthias H. et al., "Overexpression of the EGF receptor-related proto-oncogene erbB-2 in human mammary tumor cell lines by different molecular mechanisms," The EMBO Journal, vol. 6(3):605-610 (1987).
Lemoine, Nicholas R. et al., "The erbB-3 Gene in Human Pancreatic Cancer," Journal of Pathology, vol. 168:269-273 (1992).
Moscosco, Lisa M. et al., "Synapse-Associated Expression of an Acetylcholine Receptor-Inducing Protein, ARIA/ Heregulin, and Its Putative Receptors, ErbB2 and ErbB3, in Developing Mammalian Muscle," Developmental Biology, vol. 172:158-169 (1995).
Orr-Urtreger, Avi et al., "Neural expression and chromosomal mapping of Neu differentiation factor to 8p12-p21," Proc. Natl. Acad. Sci. USA, vol. 90:1867-1871 (1993).
Schmidt, M. et al., "Targeted inhibition of tumour cell growth by a bispecific single-chain toxin containing an antibody domain and TGFa," British Journal of Cancer, vol. 74:853-862 (1996).

Semba, Kentaro et al., "A v-erbB-related protooncogene, c-erbB-2, is distinct from the c-erbB-1/epidermal growth factor-receptor gene and is amplified in a human salivary gland adenocarcinoma," Proc. Natl. Acad. Sci. USA, vol. 82:6497-6501 (1985).
Shintani, Satoru et al., "Expression of C-erbB Family Gene Products in Adenoid Cystic Carcinoma of Salivary Glands: An Immunohistochemical Study," Anticancer Research, vol. 15:2623-2626 (1995).
Shintani, Satoru et al., "Prognostic significance of ERRB3 overexpression in oral squamous cell carcinoma," Cancer Letters, vol. 95:79-83 (1995).
Simpson, Barbara J.B. et al., "c-erbB Growth-factor-receptor Proteins in Ovarian Tumours," Int. J. Cancer (Pred. Oncol.), vol. 64:202-206 (1995).
Simpson, BJB et al., "c-erbB-3 protein expression in ovarian tumours," British Journal of Cancer, vol. 71:758-762 (1995).
Singer, Elizabeth et al., "Identification of a Heregulin Binding Site in HER3 Extracellular Domain," The Journal of Biological Chemistry, vol. 276(47):44266-44274 (2001).
Skinner, Ann et al., "Transcriptional regulation of the c-erbB-3 gene in human breast carcinoma cell lines," Oncogene, vol. 8:3393-3401 (1993).
Slamon, Dennis J. et al., "Human Breast Cancer: Correlation of Relapse and Survival with Amplification of the HER-2/neu Oncogene," Science, vol. 235:177-182 (1987).
Slamon, Dennis J. et al., "Studies of the HER-2/neu Proto-oncogene in Human Breast and Ovarian Cancer," Science, vol. 244:707-712 (1989).
Sliwkowski, Mark X. et al., "Coexpression of erbB2 and erbB3 Proteins Reconstitutes a High Affinity Receptor for Heregulin," The Journal of Biological Chemistry, vol. 269(2):14661-14665 (1994).
Smith, B. L. et al. "The efficacy of Herceptin therapies is influenced by the expression of other erbB receptors, their ligands and the activation of downstream signalling proteins," British Journal of Cancer, vol. 91:1190-1194 (2004).
Soltoff, Stephen P. et al., "ErbB3 Is Involved in Activation of Phosphatidylinositol 3-Kinase by Epidermal Growth Factor," Molecular and Cellular Biology, vol. 14(6):3550-3558 (1994).
Surmacz, Eva, "Growth factor receptors as therapeutic targets: strategies to inhibit the insulin-like growth factor I receptor," Oncogene, vol. 22:6589-6597 (2003).
Tzahar, Eldad et al., "A Hierarchical Network of Interreceptor Interactions Determines Signal Transduction by Neu Differentiation Factor/Neuregulin and Epidermal Growth Factor," Molecular and Cellular Biology, vol. 16 (10):5276-5287 (1996).
Tzahar, Eldad et al., "ErbB-3 and ErbB-4 Function as the Respective Low and High Affinity Receptors of All Neu Differentiation Factor/Heregulin Isoforms," The Journal of Biological Chemistry, vol. 269(40):25226-25233 (1994).
Ullrich, Axel et al., "Signal Transduction by Receptors with Tyrosine Kinase Activity," Cell, vol. 61:203-212 (1990).
Vaidya, Pradeep et al., "Overexpression of Different Members of the Type 1 Growth Factor Receptor Family and Their Association with Cell Proliferation in Periampullary Carcinoma," Journal of Pathology, vol. 178:140-145 (1996).
Wainstein, Mark A. et al., "CWR22: Androgen-dependent Xenograft Model Derived from a Primary Human Prostatic Carcinoma," Cancer Research, vol. 54:6049-6052 (1994).
Wallasch, Christian et al., "Heregulin-dependent regulation of HER2/neu oncogenic signaling by heterodimerization with HER3," The EMBO Journal, vol. 14(17):4267-4275 (1995).
Wingens, Miriam et al., "Structural Analysis of an Epidermal Growth Factor/Transforming Growth Factor-a Chimera with Unique ErbB Binding Specificity," The Journal of Biological Chemistry, vol. 278(40):39114-39123 (2003).
Wu, Dianging et al., "Human Epidermal Growth Factor (EGF) Receptor Sequence Recognized by EGF Competitive Monoclonal Antibodies," The Journal of Biological Chemistry, vol. 264(29):17469-17475 (1989).

(56) References Cited

OTHER PUBLICATIONS

Yamamoto, Tadashi et al., "Similarity of protein encoded by the human c-erb-B-2 gene to epidermal growth factor receptor," Nature, vol. 319:230-234 (1986).

Ye, Dingwei et al., "Augmentation of a humanized Anti-HER2 mAb 4D6 induced growth inhibition by a human-mouse chimeric anti-EGF receptor mAb C225," Oncogene, vol. 18:731-738 (1999).

Zelada-Hedman, Moraima et al., "High Expression of the EGFR in Fibroadenomas Compared to Breast Carcinomas," Anticancer Research, vol. 14:1679-1688 (1994).

Zhang, Ke et al., "Transformation of NIH 3T3 Cells by HER3 or HER4 Receptors Requires the Presence of HER1 or HER2," The Journal of Biological Chemistry, vol. 271(7):3884-3890 (1996).

Invitation to Pay Additional Fees for Application No. PCT/US2008/002119, dated Oct. 7, 2008.

International Search Report and Written Opinion for Application No. PCT/US2008/002119, dated Dec. 3, 2008.

International Preliminary Report on Patentability for Application No. PCT/US2008/002119, dated May 18, 2009.

* cited by examiner

Binding of Antibodies to ErbB3 as Measured by SPR $$K_D = k_d/k_a$$

Cell Binding Assay for Antibodies to MALME-3M cells $$Y = Bmax*X/K_D + X$$

Antibody#6 causes a decrease in total ErbB3 levels in MALME 3M melanoma cells *in vitro* measured by ELISA

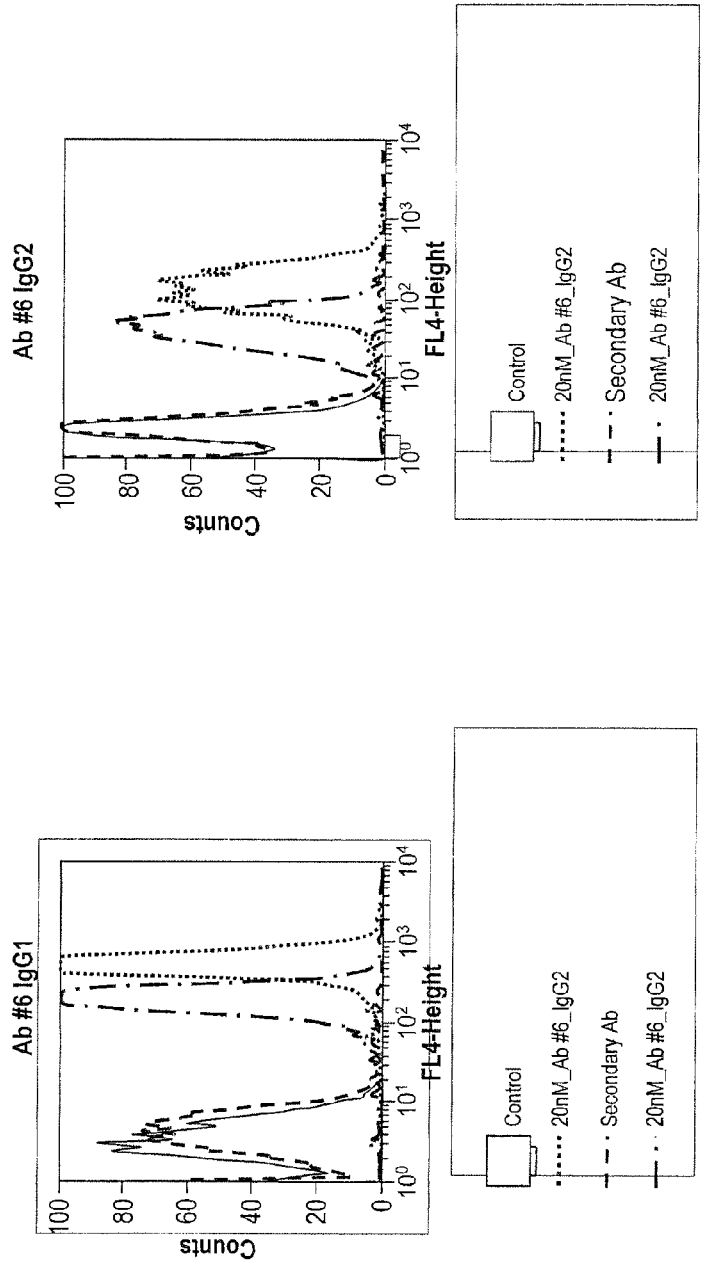

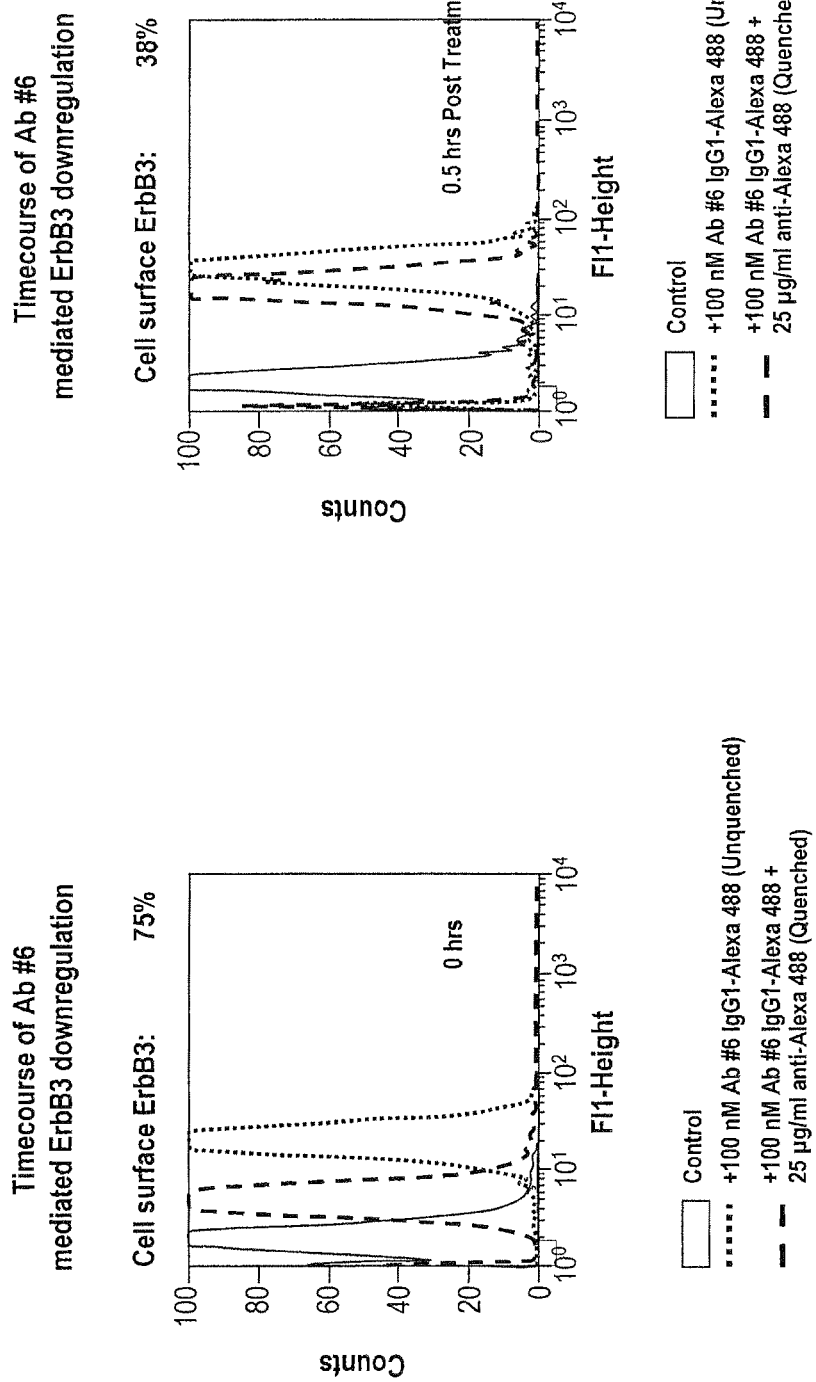

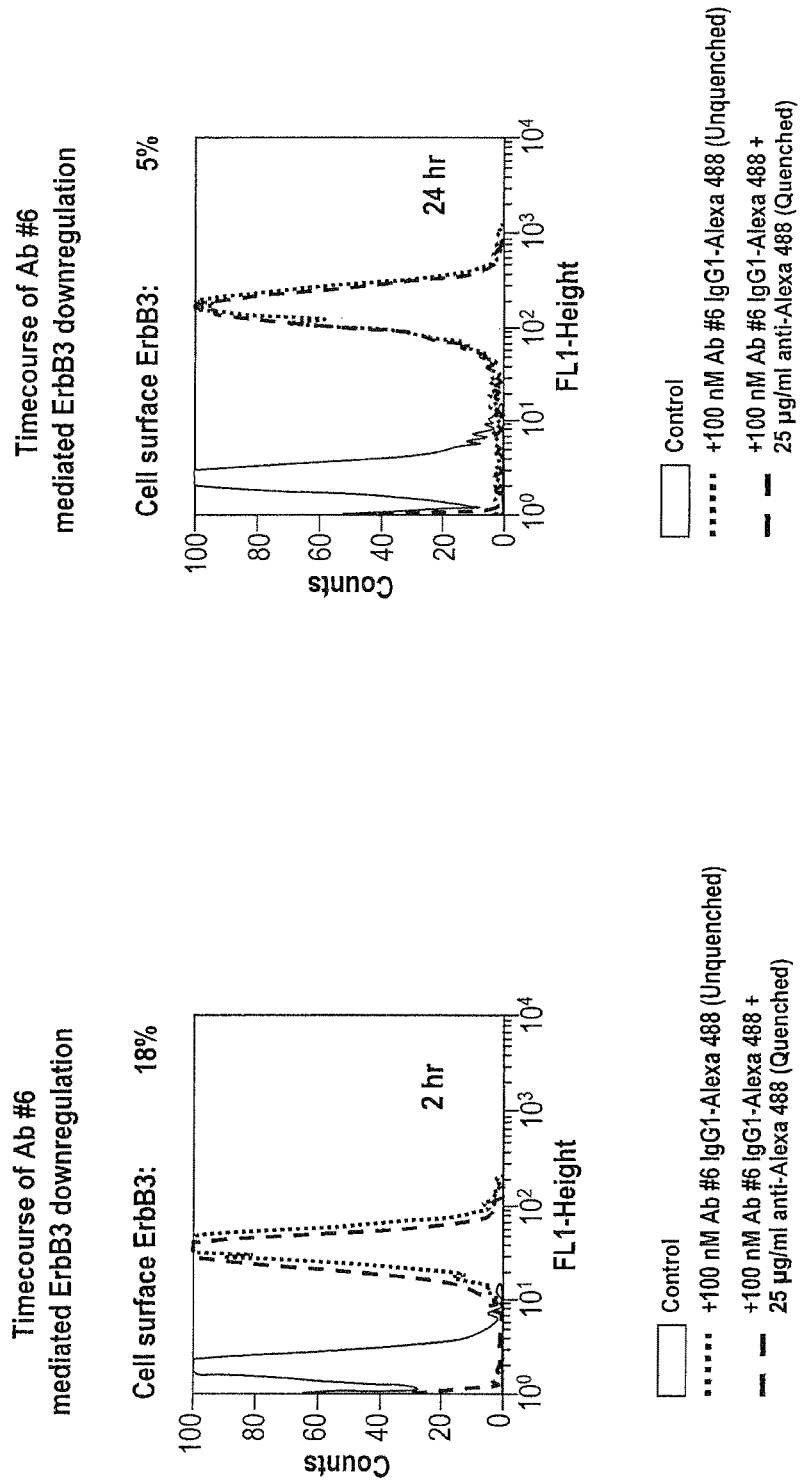

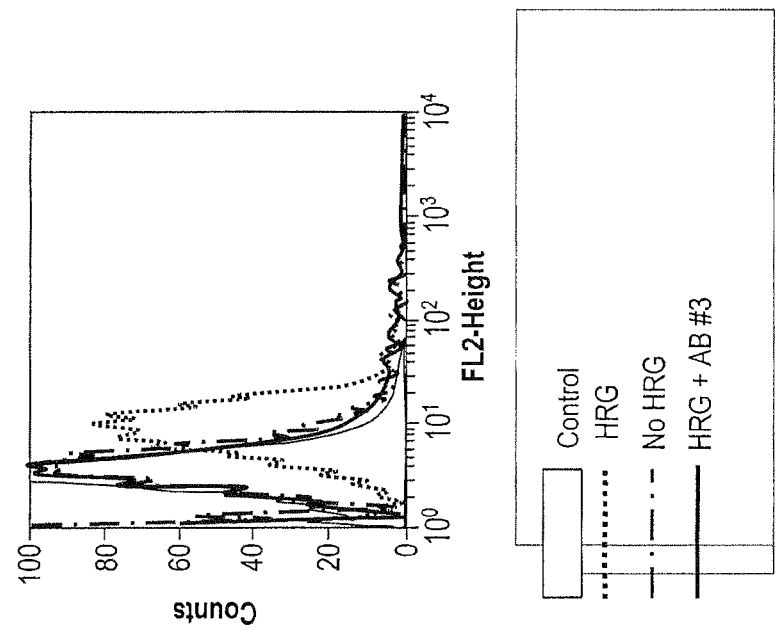
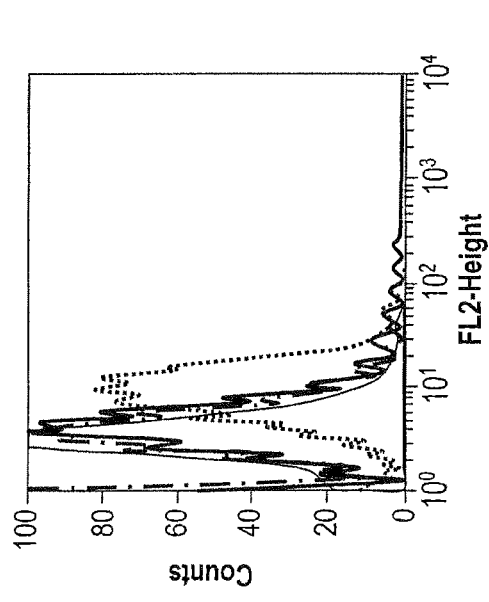
Fig. 18B
Fig. 18A

Ab # 6 VH amino acid sequence (SEQ ID NO:1)
EVQLLESGGGLVQPGGSLRLSCAASGFTFSHYVMAWVRQAPGKGLEWVSSISSS
GGWTLYADSVKGRFTISRDNSKNTLYLQMNSLRAEDTAVYYCTRGLKMATIFD
YWGQGTLVTVSS Ab # 6 VL amino acid sequence (SEQ ID NO:2)
QSALTQPASVSGSPGQSITISCTGTSSDVGSYNVVSWYQQHPGKAPKLIIYEVSQR
PSGVSNRFSGSKSGNTASLTISGLQTEDEADYYCCSYAGSSIFVIFGGGTKVTVL Ab # 3 VH amino acid sequence (SEQ ID NO:3)
EVQLLESGGGLVQPGGSLRLSCAASGFTFSAYNMRWVRQAPGKGLEWVSVIYPS
GGATRYADSVKGRFTISRDNSKNTLYLQMNSLRAEDTAVYYCARGYYYYGMDV
WGQGTLVTVSS Ab # 3 VL amino acid sequence (SEQ ID NO:4)
QSVLTQPPSASGTPGQRVTISCSGSDSNIGRNYIYWYQQFPGTAPKLLIYRNNQRP
SGVPDRISGSKSGTSASLAISGLRSEDEAEYHCGTWDDSLSGPVFGGGTKLTVL Ab # 14 VH amino acid sequence (SEQ ID NO:5)
EVQLLESGGGLVQPGGSLRLSCAASGFTFSAYGMGWVRQAPGKGLEWVSYISPS
GGHTKYADSVKGRFTISRDNSKNTLYLQMNSLRAEDTAVYYCAKVLETGLLVD
AFDIWGQGTMVTVSS Ab # 14 VL amino acid sequence (SEQ ID NO:6)
QYELTQPPSVSVYPGQTASITCSGDQLGSKFVSWYQQRPGQSPVLVMYKDKRRP
SEIPERFSGSNSGNTATLTISGTQAIDEADYYCQAWDSSTYVFGTGTKVTVL Ab # 17 VH amino acid sequence (SEQ ID NO:35)
EVQLLESGGGLVQPGGSLRLSCAASGFTFSWYGMGWVRQAPGKGLEWVSYISPS
GGITVYADSVKGRFTISRDNSKNTLYLQMNSLRAEDTAVYYCARLNYYYGLDV
WGQGTTVTVSS Ab # 17 VL amino acid sequence (SEQ ID NO:36)
QDIQMTQSPSSLSASVGDRITITCQASQDIGDSLNWYQQKPGKAPRLLIYDASNLE
TGVPPRFSGSGSGTDFTFTFRSLQPEDIATYFCQQSANAPFTFGPGTKVDIK Ab # 19 VH amino acid sequence (SEQ ID NO:37)
EVQLLESGGGLVQPGGSLRLSCAASGFTFSRYGMWWVRQAPGKGLEWVSYIGSS
GGPTYYVDSVKGRFTISRDNSKNTLYLQMNSLRAEDTAVYYCAGGRGTPYYFDS
WGQGTLVTVSS Ab # 19 VL amino acid sequence (SEQ ID NO:38)
QYELTQPASVSGSPGQSITISCTGTSSDIGRWNIVSWYQQHPGKAPKLMIYDVSNRPSGVSNRF
SGSKSGNTASLTISGLQAEDEADYYCSSYTSSSTWVFGGGTKLTVL

*Fig. 21A*

Ab # 6 VH CDR1 (SEQ ID NO:7)
HYVMA

Ab # 6 VH CDR2 (SEQ ID NO:8)
SISSSGGWTLYADSVKG

Ab # 6 VH CDR3 (SEQ ID NO:9)
GLKMATIFDY

Ab # 6 VL CDR1 (SEQ ID NO:10)
TGTSSDVGSYNVVS

Ab # 6 VL CDR2 (SEQ ID NO:11)
EVSQRPS

Ab # 6 VL CDR3 (SEQ ID NO:12)
CSYAGSSIFVI

Ab # 3 VH CDR1 (SEQ ID NO:13)
AYNMR

Ab # 3 VH CDR2 (SEQ ID NO:14)
VIYPSGGATRYADSVKG

Ab # 3 VH CDR3 (SEQ ID NO:15)
GYYYYGMDV

Ab # 3 VL CDR1 (SEQ ID NO:16)
SGSDSNIGRNYIY

Ab # 3 VL CDR2 (SEQ ID NO:17)
RNNQRPS

Ab # 3 VL CDR3 (SEQ ID NO:18)
GTWDDSLSGPV

*Fig. 21B*

Ab # 14 VH CDR1 (SEQ ID NO:19)
AYGMG

Ab # 14 VH CDR2 (SEQ ID NO:20)
YISPSGGHTKYADSVKG

Ab # 14 VH CDR3 (SEQ ID NO:21)
VLETGLLVDAFDI

Ab # 14 VL CDR1 (SEQ ID NO:22)
SGDQLGSKFVS

Ab # 14 VL CDR2 (SEQ ID NO:23)
YKDKRRPS

Ab # 14 VL CDR3 (SEQ ID NO:24)
QAWDSSTYV

Ab # 17 VH CDR1 (SEQ ID NO:39)
WYGMG

Ab # 17 VH CDR2 (SEQ ID NO:40)
YISPSGGITVYADSVKG

Ab # 17 VH CDR3 (SEQ ID NO:41)
LNYYYGLDV

Ab # 17 VL CDR1 (SEQ ID NO:42)
QASQDIGDSLN

Ab # 17 VL CDR2 (SEQ ID NO:43)
DASNLET

Ab # 17 VL CDR3 (SEQ ID NO:44)
QQSANAPFT

Ab # 19 VH CDR1 (SEQ ID NO:45)
RYGMW

Ab # 19 VH CDR2 (SEQ ID NO:46)
YIGSSGGPTYYVDSVKG

Ab # 19 VH CDR3 (SEQ ID NO:47)
GRGTPYYFDS

Ab # 19 VL CDR1 (SEQ ID NO:48)
TGTSSDIGRWNIVS

Ab # 19 VL CDR2 (SEQ ID NO:49)
DVSNRPS

Ab # 19 VL CDR3 (SEQ ID NO:50)
SSYTSSSTWV

*Fig. 21C*

Ab # 6 VH Codon Optimized Nucleic Acid Sequence (SEQ ID NO:25)

gaggtgcagctgctggagagcggcggagggctggtccagccaggcggcagcctgaggctgtcctgcgccgccagcggcttcac
cttcagccactacgtgatggcctgggtgcggcaggccccaggcaagggcctggaatgggtgtccagcatcagcagcagcggcgg
ctggaccctgtacgccgacagcgtgaagggcaggttcaccatcagcagggacaacagcaagaacaccctgtacctgcagatgaac
agcctgagggccgaggacaccgccgtgtactactgcaccaggggcctgaagatggccaccatcttcgactactggggccagggc
accctggtgaccgtgagcagc Ab # 6 VL Codon Optimized Nucleic Acid Sequence (SEQ ID NO:26)

cagtccgccctgacccagcccgccagcgtgagcggcagcccaggccagagcatcaccatcagctgcaccggcaccagcagcga
cgtgggcagctacaacgtggtgtcctggtatcagcagcaccccggcaaggcccccaagctgatcatctacgaggtgtcccagagg
cccagcggcgtgagcaacaggttcagcggcagcaagagcggcaacaccgccagcctgaccatcagcggcctgcagaccgagg
acgaggccgactactactgctgcagctacgccggcagcagcatcttcgtgatcttcggcggagggaccaaggtgaccgtccta Ab # 3 VH Codon Optimized Nucleic Acid Sequence (SEQ ID NO:27)

gaggtgcagctgctggaaagcggcggagggctggtgcagccaggcggcagcctgaggctgtcctgcgccgccagcggcttcac
cttcagcgcctacaacatgagatgggtgcggcaggccccaggcaagggcctggaatgggtgtccgtgatctaccccagcggcgg
agccaccagatacgccgacagcgtgaagggcaggttcaccatcagcagggacaacagcaagaacaccctgtacctgcagatgaa
cagcctgagggccgaggacaccgccgtgtactactgcgccaggggctactactactacggcatggacgtgtggggccagggcac
cctggtgaccgtgagcagc Ab # 3 VL Codon Optimized Nucleic Acid Sequence (SEQ ID NO:28)

cagagcgtgctgacccagcccccaagcgccagcggcaccccaggccagagggtgaccatcagctgcagcggcagcgacagca
acatcggcaggaactacatctactggtatcagcagttccccggcaccgcccccaagctgctgatctacaggaacaaccagaggccc
agcggcgtgcccgacaggatcagcggcagcaagagcggcaccagcgccagcctggccatcagcggcctgagaagcgaggac
gaggccgagtaccactgcggcacctgggacgacagcctgagcggcccagtgttcggcggagggaccaagctgaccgtccta

*Fig. 22A*

Ab # 14 VH Nucleic Acid Sequence (SEQ ID NO:29)

gaagttcaattgttagagtctggtggcggtcttgttcagcctggtggttctttacgtctttcttgcgctgcttccggattcactttctct
gcttacggtatgggttgggttcgccaagctcctggtaaaggtttggagtgggtttcttatatctctccttctggtggccatactaag
tatgctgactccgttaaaggtcgcttcactatctctagagacaactctaagaatactctctacttgcagatgaacagcttaagggc
tgaggacacggccgtatattactgtgcgaaagtactggaaactggcttattggttgatgcttttgatatctggggccaagggaca
atggtcaccgtctcaagc Ab # 14 VL Nucleic Acid Sequence (SEQ ID NO:30)

cagtacgaattgactcagccacccctcagtgtccgtgtacccaggacagacagccagcatcacctgctctggagatcaattggg
gagtaaatttgtttcctggtatcagcagaggccaggccagtcccctgtgttggtcatgtataaagataaaaggcggccgtcaga
gatccctgagcgattctctggctccaactctgggaacacagccactctgaccatcagcgggacccaggctatagatgaggct
gactattattgtcaggcgtgggacagcagcacttatgtcttcggcactgggaccaaggtcaccgtccta Ab # 6 VH Pre-Optimization Nucleic Acid Sequence (SEQ ID NO:31)

gaagttcaattgttagagtctggtggcggtcttgttcagcctggtggttctttacgtctttcttgcgctgcttccggattcactttctct
cattacgttatggcttgggttcgccaagctcctggtaaaggtttggagtgggtttcttctatctcttcttctggtggctggactctttat
gctgactccgttaaaggtcgcttcactatctctagagacaactctaagaatactctctacttgcagatgaacagcttaagggctg
aggacacagccgtgtattactgtactagaggtctcaagatggctacaattttttgactactggggccagggcaccctggtcaccg
tctcaagc Ab # 6 VL Pre-Optimization Nucleic Acid Sequence (SEQ ID NO:32)

cagagcgctttgactcagcctgcctccgtgtctgggtctcctggacagtcgatcaccatctcctgcactggaaccagcagtgat
gttgggagttataatgttgtctcctggtaccaacaacacccaggcaaagcccccaaactcatcatttatgaggtcagtcagcgg
ccctcaggggttctaatcgcttctctggctccaagtctggcaacacggcctccctgacaatctctgggctccagactgaggac
gaggctgattattactgctgctcatatgcaggtagtagtatttcgtgatattcggcggagggaccaaggtgaccgtccta Ab # 3 VH Pre-Optimization Nucleic Acid Sequence (SEQ ID NO:33)

gaagttcaattgttagagtctggtggcggtcttgttcagcctggtggttctttacgtctttcttgcgctgcttccggattcactttctct
gcttacaatatgcgttgggttcgccaagctcctggtaaaggtttggagtgggtttctgttatctatccttctggtggcgctactcgtt
atgctgactccgttaaaggtcgcttcactatctctagagacaactctaagaatactctctacttgcagatgaacagcttaagggct
gaggacacggccgtgtattactgtgcgagagggtactactactacggtatggacgtctggggccaaggcaccctggtcaccg
tctcaagc Ab # 3 VL Pre-Optimization Nucleic Acid Sequence (SEQ ID NO:34)

cagagcgtcttgactcagccacccctcagcgtctgggaccccgggcagagggtcaccatctcgtgttctggaagcgactcca
acatcggaagaaattatatatattggtaccagcaattcccaggaacggccccaagctcctcatctataggaataatcagcggc
cctcaggggtccctgaccgaatctctggctccaagtctggcacctcagcctccctggccatcagtgggctccggtccgaggat
gaggctgagtatcactgtggaacatgggatgacagcctgagtggtccggtattcggcggagggactaagctgaccgtccta

*Fig. 22B*

- Ab #6 VLb:
- QSALTQPASVSGSPGQSITISCTGTSSDVGSYNVVSWYQQHPGKAPK
  LMIYEVSKRPSGVSNRFSGSKSGNTASLTISGLQAEDEADYYCCSYA
  GSSIFVIFGGGTKVTVL (SEQ ID NO:51)

- Ab #17 VK1b:
- QDIQMTQSPSSLSASVGDRITITCQASQDIGDSLNWYQQKPGKAPRLL
  IYDASNLETGVPPRFSGSGSGTDFTFTFRSLQPEDIATYFCQQSANAP
  FTFGPGTKVDIR (SEQ ID NO:52)

- Ab #19 VL2b:
- QYELTQPASVSGSPGQSITISCTGTSSDIGRWNIVSWYQQHPGKAPK
  LMIYDVSNRPSGVSNRFSGSKSGNTASLTISGLQAEDEADYYCSSYTS
  SSTVVFGGGTKLTVL (SEQ ID NO:53)

ANTIBODIES AGAINST ERBB3 AND USES THEREOF

BACKGROUND OF THE INVENTION

The ErbB/HER subfamily of polypeptide growth factor receptors include the epidermal growth factor (EGF) receptor (EGFR, ErbB1/HER1), the neu oncogene product (ErbB2/HER2), and the more recently identified ErbB3/HER3 and ErbB4/HER4 receptor proteins (see, e.g., Hynes et. al. (1994) Biochim. Biophys. Acta Rev. Cancer 1198, 165-184). Each of these receptors is predicted to consist of an extracellular ligand-binding domain, a membrane-spanning domain, a cytosolic protein tyrosine kinase (PTK) domain and a C-terminal phosphorylation domain (see, e.g., Kim et al., (1998) Biochem. J. 334, 189-195).

Experiments in vitro have indicated that the protein tyrosine kinase activity of the ErbB3 protein is attenuated significantly relative to that of other ErbB/HER family members and this attenuation has been attributed, in part, to the occurrence of non-conservative amino acid substitutions in the predicted catalytic domain of ErbB3 (see, e.g., Guy et al. (1994) Proc. Natl. Acad. Sci. USA. 91, 8132-8136; Sierke et al. (1997) Biochem. J. 322, 757-763). However, the ErbB3 protein has been shown to be phosphorylated in a variety of cellular contexts. For example, ErbB3 is constitutively phosphorylated on tyrosine residues in a subset of human breast cancer cell lines overexpressing this protein (see, e.g., Kraus et al. (1993) Proc. Natl. Acad. Sci. USA. 90, 2900-2904; and Kim et al. Supra; see, also, Schaefer et al. (2006) Neoplasia 8(7):613-22 and Schaefer et al. Cancer Res (2004) 64(10): 3395-405).

Although, the role of ErbB3 in cancer has been explored (see, e.g., Horst et al. (2005) 115, 519-527; Xue et al. (2006) Cancer Res. 66, 1418-1426), ErbB3 remains largely unappreciated as a target for clinical intervention. Current immunotherapies primarily focus on inhibiting the action of ErbB2 and, in particular, heterodimerization of ErbB2/ErbB3 complexes (see, e.g., Sliwkowski et al. (1994) J. Biol. Chem. 269(20):14661-14665 (1994)). Accordingly, it is an object of the present invention to provide improved immunotherapies that effectively inhibit ErbB3 signaling, and can be used to treat and diagnose a variety of cancers.

SUMMARY OF THE INVENTION

The present invention provides a novel class of monoclonal antibodies which binds to the ErbB3 receptor and inhibits various ErbB3 functions. For example, the antibodies described herein are capable of binding to ErbB3 and inhibiting EGF-like ligand mediated phosphorylation of the receptor. As described herein, EGF-like ligands include EGF, TGF-α, betacellulin, heparin-binding epidermal growth factor, biregulin and amphiregulin, which bind to EGFR and induce dimerization of EGFR with ErbB3. This dimerization, in turn, causes phosphorylation of ErbB3, and activates signaling through the receptor. Monoclonal antibodies of the present invention, thus, are useful for treating and diagnosing a variety of cancers associated with ErbB3-mediated cellular signaling. Accordingly, in one embodiment, the present invention provides monoclonal antibodies (and antigen binding portions thereof) which bind to ErbB3 and inhibit EGF-like ligand mediated phosphorylation of ErbB3.

In another embodiment, the antibodies are further characterized by one or more of the following properties: (i) inhibition of ErbB3 ligand-mediated signaling, including signaling mediated by binding of ErbB3 ligands, such as heregulin, epiregulin, epigen and BIR, to ErbB3; (ii) inhibition of proliferation of cells expressing ErbB3; (iii) the ability to decrease levels of ErbB3 on cell surfaces (e.g., by inducing internalization of ErbB3); (iv) inhibition of VEGF secretion of cells expressing ErbB3; (v) inhibition of the migration of cells expressing ErbB3; (vi) inhibition of spheroid growth of cells expressing ErbB3; and/or (vii) binding to an epitope located on domain I (residues 20-209) of ErbB3, for example, an epitope involving or spanning residues 20-202 of the amino acid sequence of ErbB3, more preferably involving or spanning residues 93-104, even more preferably involving residues 93, 101, 102 and 104.

Particular monoclonal antibodies and antigen binding portions thereof of the present invention exhibit a $K_D$ of 50 nM or less, as measured by a surface plasmon resonance assay or a cell binding assay In further embodiments, particular monoclonal antibodies and antigen binding portions thereof of the present invention include a heavy chain variable region comprising an amino acid sequence which is at least 80% (e.g., 85%, 90%, 95%, 96%, 97%, 98% or 99%) identical to the heavy chain variable region amino acid sequence set forth in SEQ ID NO:1, SEQ ID NO:3, SEQ ID NO:5, SEQ ID NO:35, or SEQ ID NO: 37. Other particular monoclonal antibodies and antigen binding portions thereof of the present invention include a light chain variable region comprising an amino acid sequence which is at least 80% (e.g., 85%, 90%, 95%, 96%, 97%, 98% or 99%) identical to the light chain variable region amino acid sequence set forth in SEQ ID NO:2, SEQ ID NO:4, SEQ ID NO:6, SEQ ID NO:36, or SEQ ID NO:38. The antibodies may also include both of the aforementioned heavy chain and light chain variable regions.

The variable heavy and light chain regions of the antibodies or antigen binding portions thereof typically include one or more complementarity determining regions (CDRs). These include one or more CDR1, CDR2, and CDR3 regions. Accordingly, other particular antibodies and antigen binding portions thereof of the present invention include one or more CDR sequences selected from a heavy chain variable region CDR1 comprising SEQ ID NO:7; a heavy chain variable region CDR2 comprising SEQ ID NO:8; a heavy chain variable region CDR3 comprising SEQ ID NO:9; a light chain variable region CDR1 comprising SEQ ID NO:10; a light chain variable region CDR2 comprising SEQ ID NO:11; a light chain variable region CDR3 comprising SEQ ID NO:12; and combinations thereof.

Still other particular antibodies and antigen binding portions thereof of the present invention include one or more CDR sequences selected from a heavy chain variable region CDR1 comprising SEQ ID NO:13; a heavy chain variable region CDR2 comprising SEQ ID NO:14; a heavy chain variable region CDR3 comprising SEQ ID NO:15; a light chain variable region CDR1 comprising SEQ ID NO:16; a light chain variable region CDR2 comprising SEQ ID NO:17; a light chain variable region CDR3 comprising SEQ ID NO:18; and combinations thereof.

Still other particular antibodies and antigen binding portions thereof of the present invention include; or one or more CDR sequences selected from a heavy chain variable region CDR1 comprising SEQ ID NO:19; a heavy chain variable region CDR2 comprising SEQ ID NO:20; a heavy chain variable region CDR3 comprising SEQ ID NO:21; a light chain variable region CDR1 comprising SEQ ID NO:22; a light chain variable region CDR2 comprising SEQ ID NO:23; a light chain variable region CDR3 comprising SEQ ID NO:24; and combinations thereof.

Still other particular antibodies and antigen binding portions thereof of the present invention include; or one or more CDR sequences selected from a heavy chain variable region CDR1 comprising SEQ ID NO:39; a heavy chain variable region CDR2 comprising SEQ ID NO:40; a heavy chain variable region CDR3 comprising SEQ ID NO:41; a light chain variable region CDR1 comprising SEQ ID NO:42; a light chain variable region CDR2 comprising SEQ ID NO:43; a light chain variable region CDR3 comprising SEQ ID NO:44; and combinations thereof.

Still other particular antibodies and antigen binding portions thereof of the present invention include; or one or more CDR sequences selected from a heavy chain variable region CDR1 comprising SEQ ID NO:45; a heavy chain variable region CDR2 comprising SEQ ID NO:46; a heavy chain variable region CDR3 comprising SEQ ID NO:47; a light chain variable region CDR1 comprising SEQ ID NO:48; a light chain variable region CDR2 comprising SEQ ID NO:49; a light chain variable region CDR3 comprising SEQ ID NO:50; and combinations thereof.

The antibodies and antigen binding portions thereof may also comprise one or more CDRs which are at least 80% (e.g., 85%, 90%, 95%, 96%, 97%, 98% or 99%) identical to any of the aforementioned CDRs, or combinations of CDRs.

In one embodiment, the antibodies and antibody portions thereof are fully human (i.e., contains human CDR and framework sequences). Particular human antibodies of the present invention include those having a heavy chain variable region that is from a human VH3 germ line gene, and/or a light chain variable region from human VL2 germ line gene.

Also encompassed by the present invention are monoclonal antibodies and portions thereof that bind to the same or overlapping epitopes bound by any of the antibodies or portions thereof described herein (e.g., an epitope located on domain I of ErbB3, such as an epitope involving or spanning, residues 20-202 of the amino acid sequence of ErbB3, more preferably involving or spanning residues 93-104, even more preferably involving residues 93, 101, 102 and 104). Antibodies which have the same activity as the antibodies described herein, e.g., antibodies having the same sequence as Ab #6, are also encompassed by the present invention.

Antibodies of the present invention include all known forms of antibodies and other protein scaffolds with antibody-like properties. For example, the antibody can be a human antibody, a humanized antibody, a bispecific antibody, a chimeric antibody or a protein scaffold with antibody-like properties, such as fibronectin or Ankyrin repeats. The antibody also can be a Fab, Fab'2, ScFv, SMIP, affibody, nanobody, or a domain antibody. The antibody also can have any of the following isotypes: IgG1, IgG2, IgG3, IgG4, IgM, IgA1, IgA2, IgAsec, IgD, and IgE.

In yet another embodiment, the present invention further provides compositions comprising combinations of antibodies or antigen binding portions described herein, formulated with an acceptable carrier and/or adjuvant. In a particular embodiment, the composition comprises two or more antibodies that bind different epitopes on ErbB3 or antibodies described herein combined with anti-cancer antibodies which do not bind ErbB3.

In still another embodiment, the present invention provides isolated nucleic acids encoding the antibodies and antigen binding portions thereof described herein. In particular embodiments, the nucleic acid encodes a heavy chain variable region comprising a nucleotide sequence which is at least 80% (e.g., 85%, 90%, 95%, 96%, 97%, 98% or 99%) identical to, or which hybridizes under high stringency conditions to, SEQ ID NO:25, SEQ ID NO:27, SEQ ID NO:29, SEQ ID NO:35, or SEQ ID NO:37; or a light chain variable region comprising a nucleotide sequence which is at least 80% (e.g., 85%, 90%, 95%, 96%, 97%, 98% or 99%) identical to, or which hybridizes under high stringency conditions to, SEQ ID NO:26, SEQ ID NO:28, SEQ ID NO:30, SEQ ID NO:36, or SEQ ID NO:38; or combinations of such heavy and light variable regions.

The present invention further provides transgenic non-human mammals, hybridomas, and transgenic plants that express and/or produce the antibodies and antigen binding portions described herein.

Also provided by the invention are kits comprising one or more isolated monoclonal antibodies or antigen binding portions thereof described herein and, optionally, instructions for use in treating or diagnosing a disease associated with ErbB3 dependent signaling, such as cancers.

Antibodies and antigen binding portions thereof of the present invention can be used in a broad variety of therapeutic and diagnostic applications, particularly oncological applications. Accordingly, in another aspect, the invention provides method for inhibiting EGF-like ligand mediated phosphorylation of ErbB3 in a subject by administering one or more antibodies or antigen binding portions thereof described herein in an amount sufficient to inhibit EGF-like mediated phosphorylation of ErbB3. The invention further provides methods for treating a variety of cancers in a subject, including, but not limited to, melanoma, breast cancer, ovarian cancer, renal carcinoma, gastrointestinal/colon cancer, lung cancer, clear cell sarcoma, and prostate cancer, by administering one or more antibodies or antigen binding portions thereof described herein in an amount sufficient to treat the cancer. In one embodiment, the cancer comprises a KRAS mutation. In another embodiment, the cancer comprises a PI3K mutation. The antibodies or antigen binding portions thereof can be administered alone or in combination with other therapeutic agents, such as anti-cancer agents, e.g., other antibodies, chemotherapeutic agents and/or radiation. Preferred anti-cancer agents for combination therapy include erlotinib, paclitaxel and cisplatin.

In yet other embodiments, the invention provides methods for diagnosing and prognosing diseases (e.g., cancers) associated with ErbB3. In one embodiment, this is achieved by contacting antibodies or antigen binding portions of the invention (e.g., ex vivo or in vivo) with cells from the subject, and measuring the level of binding to ErbB3 on the cells, wherein abnormally high levels of binding to ErbB3 indicate that the subject has a cancer associated with ErbB3.

Other features and advantages of the invention will be apparent from the following detailed description, and from the claims.

BRIEF DESCRIPTION OF THE DRAWINGS

FIGS. 2A and 2B are graphs depicting the $K_D$ value of Antibody #6 (referred to as Ab #6) and Antibody #3 (referred to as Ab #3), respectively, as measured using surface plasmon resonance (SPR) technology. FIGS. 2C and 2D are graphs depicting the $K_D$ values of Ab #6 and Ab #3, respectively, as measured using a cell binding assay using MALME-3M melanoma cells.

FIGS. 5A and 5B are graphs depicting the ability of an anti-ErbB3 antibody (Ab #6) to downregulate ErbB3 receptors on MALME-3M cells, measured using FACS analysis. FIG. 5A shows the results using an IgG1 isotype of the antibody. FIG. 5B shows the results using an IgG2 isotype of the antibody.

FIGS. 6A-6D are graphs depicting the timecourse of antibody-mediated ErbB3 downregulation (Ab #6), as measured using FACS analysis.

FIG. 16A depicts the ability of the Ab #6 to inhibit heregulin-mediated phosphorylation of ErbB3 in MALME-3M cells and 16B depicts the ability of Ab #6 to inhibit phosphorylation of AKT in MALME-3M cells.

FIGS. 18A and 18B are graphs depicting the ability of Ab #6 (FIG. 18A) and Fab for Ab #3 (FIG. 18B) to inhibit heregulin binding to ErbB3 on MALME-3M cells, as measured using FACS analysis.

FIG. 19A depicts the binding of epiregulin to ADRr cells, and FIG. 19B depicts the ability of both Erbitux and Ab #6 to inhibit epiregulin binding to ADRr cells.

FIGS. 21A-21C show the amino acid sequences of the variable heavy and light chain regions of antibodies: Ab #6, Ab #3, Ab #14, Ab #17, and Ab #19.

FIGS. 22A-22B show the nucleotide sequences of the variable heavy and light chain regions of antibodies: Ab #6, Ab #3, and Ab #14.

FIG. 23 shows the amino acid sequences of the variable light chain regions of antibodies: Ab #6, Ab #17, and Ab #19, which have been reverted to the corresponding germline amino acid sequence. Amino acid residue changes are underlined.

DETAILED DESCRIPTION OF THE INVENTION

Figure 1A:
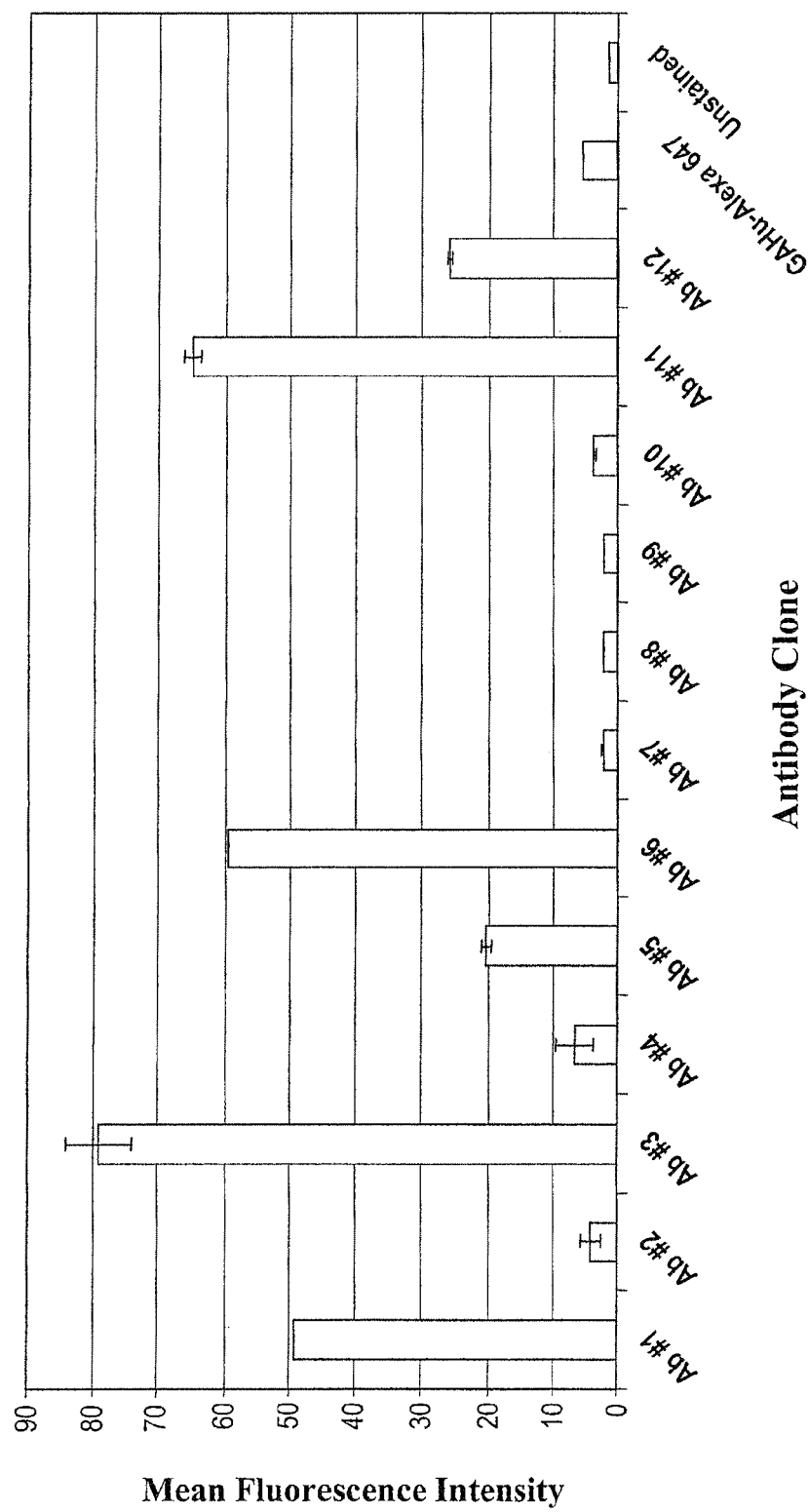
FIGS. 1A and 1B are bar graphs depicting the binding of various anti-ErbB3 antibody candidates (Fabs, referred to as Abs herein) to ErbB3 expressed on MALME-3M melanoma cells using a goat anti-human Alexa 647 secondary antibody.

In order that the present invention may be more readily understood, certain terms are first defined. Additional definitions are set forth throughout the detailed description.

I. Definitions

The terms "ErbB3," "HER3," "ErbB3 receptor," and "HER3 receptor," as used interchangeably herein, refer human ErbB3 protein, as described in U.S. Pat. No. 5,480,968 and Plowman et al., *Proc. Natl. Acad. Sci. USA*, 87:4905-4909 (1990); see, also, Kani et al., Biochemistry 44:15842-857 (2005), Cho and Leahy, Science 297:1330-1333 (2002)).

The term "EGF-like ligand," as used herein, refers to ligands of epidermal growth factor receptor (EGFR), including epidermal growth factor (EGF) and closely related proteins, such as transforming growth factor-α (TGF-α), betacellulin (BTC), heparin-binding epidermal growth factor (HB-EGF), biregulin (BIR) and amphiregulin (AR), which bind to EGFR on the surface of cells and stimulate the receptor's intrinsic protein-tyrosine kinase activity. Specifically, EGF-like ligands induce formation of EGFR (also referred to as ErbB1) and ErbB3 protein complex (see e.g., Kim et al., (1998) *Biochem J.*, 334:189-195), which results in phosphorylation of tyrosine residues in the complex.

The antibodies and antigen binding portions thereof of the present invention inhibit EGF-like ligand mediated phosphorylation of ErbB3 and, in certain embodiments, exhibit one or more of the following additional properties: (i) inhibition of one or more of heregulin, epiregulin, epigen and biregulin (BIR)-mediated signaling through ErbB3; (ii) inhibition of proliferation of cells expressing ErbB3; (iii) the ability to decrease levels of ErbB3 on cell surfaces; (iv) inhibition of VEGF secretion of cells expressing ErbB3; (v) inhibition of the migration of cells expressing ErbB3; (vi) inhibition of spheroid growth of cells expressing ErbB3; and/or (vii) binding to an epitope located on domain I of ErbB3, e.g., an epitope which involves or spans residues 20-202 of the amino acid sequence of ErbB3, more preferably involving or spanning or containing or comprising or including residues 93-104, even more preferably involving or containing or comprising or including residues 93, 101, 102 and 104. Further details on epitope mapping are provided in Example 18.

The term "inhibition" as used herein, refers to any statistically significant decrease in biological activity, including full blocking of the activity. For example, "inhibition" can refer to a decrease of about 10%, 20%, 30%, 40%, 50%, 60%, 70%, 80%, 90%, or 100% in biological activity.

Accordingly, the phrase "inhibition of EGF-like ligand mediated phosphorylation of ErbB3," as used herein, refers to the ability of an antibody or antigen binding portion to statistically significantly decrease the phosphorylation of ErbB3 induced by an EGF-like ligand, relative to the phosphorylation in an untreated (control) cell. The cell which expresses ErbB3 can be a naturally occurring cell or cell line or can be recombinantly produced by introducing nucleic acid encoding ErbB3 into a host cell. In one embodiment, the antibody or antigen binding portion thereof inhibits EGF-like ligand mediated phosphorylation of ErbB3 by at least 10%, or at least 20%, or at least 30%, or at least 40%, or at least 50%, or at least 60%, or at least 70%, or at least 80%, or at least 90%, or 100%, as determined, for example, by Western blotting followed by probing with an anti-phosphotyrosine antibody as described in Kim et al., (1998) *Biochem J.*, 334:189-195 and the Examples infra.

The phrase "inhibition of heregulin, epiregulin, epigen or biregulin-mediated signaling through ErbB3," as used herein, refers to the ability of an antibody or an antigen-binding portion thereof to statistically significantly decrease signaling mediated by an ErbB3 ligand (e.g., heregulin, epiregullin, epigen and biregulin) through ErbB3, relative to the signaling in the absence of the antibody (control). ErbB3-ligands are also referred to herein as "heregulin-like ligands." This means that, in the presence of the antibody or antigen binding portion thereof, a signal mediated in a cell expressing ErbB3 by one or more of heregulin, epiregulin, epigen and biregulin, relative to a control (no antibody), is statistically significantly decreased. An ErbB3-ligand mediated signal can be measured by assaying for the level or activity of an ErbB3 substrate, and/or a protein which is present in a cellular cascade involving ErbB3. In one embodiment, the antibody or antigen binding portion thereof decreases the level or activity of an ErbB3 substrate and/or that of a protein in a cellular cascade involving ErbB3, by at least 10%, or at least 20%, or at least 30%, or at least 40%, or at least 50%, or at least 60%, or at least 70%, or at least 80%, or at least 90%, or 100% relative to the level or activity in the absence of such antibody or antigen binding portion thereof (control). Such ErbB3-ligand mediated signaling can be measured using art recognized techniques which measure the level or activity of a substrate of ErbB3 (e.g., SHC or PI3K) or a protein in a cellular cascade involving ErbB3 (e.g., AKT) using kinase assays for such proteins (see, e.g., Horst et al. supra, Sudo et al. (2000) *Methods Enzymol*, 322:388-92; and Morgan et al. (1990) *Eur. J. Biochem.*, 191:761-767).

In a particular embodiment, the antibody or antigen binding portion thereof inhibits ErbB3-ligand (e.g., heregulin, epiregulin, epigen or biregulin) mediated signaling through ErbB3 by inhibiting the binding of the ErbB3-ligand (e.g., one or more of heregulin, epiregulin, epigen or biregulin) to ErbB3. Some ligands (e.g., biregulin or BIR) function both as EGF-like ligands (i.e., bind to EGFR/ErbB1) as well as ErbB3-like ligands (i.e., bind to ErbB3).

The phrase "inhibition of heregulin, epiregulin, epigen or biregulin binding to ErbB3," as used herein, refers to the ability of an antibody or an antigen-binding portion thereof to statistically significantly decrease the binding of an ErbB3 ligand (e.g., one or more of heregulin, epiregulin, epigen or biregulin) to ErbB3, relative to the binding in the absence of the antibody (control). This means that, in the presence of the antibody or antigen binding portion thereof, the amount of the ErbB3-ligand (e.g., heregulin, epiregulin, epigen or biregulin) which binds to ErbB3 relative to a control (no antibody), is statistically significantly decreased. The amount of an ErbB3 ligand which binds ErbB3 may be decreased in the presence of an antibody or antigen binding portion thereof of the invention by at least 10%, or at least 20%, or at least 30%, or at least 40%, or at least 50%, or at least 60%, or at least 70%, or at least 80%, or at least 90%, or 100% relative to the amount in the absence of the antibody or antigen binding portion thereof (control). A decrease in ErbB3-ligand binding can be measured using art recognized techniques which measure the level of binding of labeled ErbB3-ligand (e.g., radiolabelled heregulin, epiregulin, epigen or biregulin) to cells expressing ErbB3 in the presence or absence (control) of the antibody or antigen binding portion thereof.

The phrase "inhibition of proliferation of a cell expressing ErbB3," as used herein, refers to the ability of an antibody or an antigen-binding portion thereof to statistically significantly decrease proliferation of a cell expressing ErbB3 relative to the proliferation in the absence of the antibody. In one embodiment, the proliferation of a cell expressing ErbB3 (e.g., a cancer cell) may be decreased by at least 10%, or at least 20%, or at least 30%, or at least 40%, or at least 50%, or at least 60%, or at least 70%, or at least 80%, or at least 90%, or 100% when the cells are contacted with the antibody or antigen binding portion thereof of the present invention, relative to the proliferation measured in the absence of the antibody or antigen binding portion thereof (control). Cellular proliferation can be assayed using art recognized techniques which measure rate of cell division, the fraction of cells within a cell population undergoing cell division, and/or rate of cell loss from a cell population due to terminal differentiation or cell death (e.g., using a cell titer glow assay or thymidine incorporation).

The phrase "the ability to decrease levels of ErbB3 on cell surfaces," as used herein, refers to the ability of an antibody or antigen binding portion thereof to statistically significantly reduce the amount of ErbB3 found on the surface of a cell which has been exposed to the antibody relative to an untreated (control) cell. For example, a decrease in levels of ErbB3 on cell surfaces may result from increased internalization of ErbB3 (or increased ErbB3 endocytosis). In one embodiment, the antibody or antigen binding portion thereof decreases cell surface expression of ErbB3 by at least 10%, or at least 20%, or at least 30%, or at least 40%, or at least 50%, or at least 60%, or at least 70%, or at least 80%, or at least 90%, or 100% and/or increases internalization of the ErbB3 receptor by at least 10%, or at least 20%, or at least 30%, or at least 40%, or at least 50%, or at least 60%, or at least 70%, or at least 80%, or at least 90%, or 100% relative to the cell surface expression or internalization in the absence of the antibody or antigen binding portion thereof (control). The levels of ErbB3 on surfaces of cells and/or internalization of the ErbB3 receptor in the absence and the presence of an antibody or antigen-binding portion thereof can be readily measured using art recognized techniques, such as those described in Horst et al., supra and in the examples herein.

The phrase "inhibition of VEGF secretion of cells expressing ErbB3," as used herein, refers to the ability of an antibody or an antigen-binding portion thereof to statistically significantly decrease VEGF secretion of a cell expressing ErbB3 relative to the VEGF secretion in the absence of the antibody. In one embodiment, the VEGF secretion of a cell expressing ErbB3 (e.g., a cancer cell) may be decreased by at least 10%, or at least 20%, or at least 30%, or at least 40%, or at least 50%, or at least 60%, or at least 70%, or at least 80%, or at least 90%, or 100% when the cells are contacted with the antibody or antigen binding portion thereof of the present invention, relative to the VEGF secretion measured in the absence of the antibody or antigen binding portion thereof (control). VEGF secretion can be assayed using art recognized techniques, such as those described herein.

The phrase "inhibition of the migration of cells expressing ErbB3," as used herein, refers to the ability of an antibody or an antigen-binding portion thereof to statistically significantly decrease the migration of a cell expressing ErbB3 relative to the migration of the cell in the absence of the antibody. In one embodiment, the migration of a cell expressing ErbB3 (e.g., a cancer cell) may be decreased by at least 10%, or at least 20%, or at least 30%, or at least 40%, or at least 50%, or at least 60%, or at least 70%, or at least 80%, or at least 90%, or 100% when the cells are contacted with the antibody or antigen binding portion thereof of the present invention, relative to cell migration measured in the absence of the antibody or antigen binding portion thereof (control). Cell migration can be assayed using art recognized techniques, such as those described herein.

The phrase "inhibition of spheroid growth of cells expressing ErbB3," as used herein, refers to the ability of an antibody or an antigen-binding portion thereof to statistically significantly decrease the migration of a cell expressing ErbB3 relative to the migration of the cell in the absence of the antibody. In one embodiment, the migration of a cell expressing ErbB3 (e.g., a cancer cell) may be decreased by at least 10%, or at least 20%, or at least 30%, or at least 40%, or at least 50%, or at least 60%, or at least 70%, or at least 80%, or at least 90%, or 100% when the cells are contacted with the antibody or antigen binding portion thereof of the present invention, relative to cell migration measured in the absence of the antibody or antigen binding portion thereof (control). Cell migration can be assayed using art recognized techniques, such as those described herein.

The term "antibody" or "immunoglobulin," as used interchangeably herein, includes whole antibodies and any antigen binding fragment (i.e., "antigen-binding portion") or single chains thereof. An "antibody" comprises at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. Exemplary antibodies of the invention include antibodies#1, 3 and 14, and antigen-binding portions thereof.

The term "antigen-binding portion" of an antibody (or simply "antibody portion"), as used herein, refers to one or more fragments of an antibody that retain the ability to specifically bind to an antigen (e.g., ErbB3). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb including VH and VL domains; (vi) a dAb fragment (Ward et al. (1989) *Nature* 341, 544-546), which consists of a $V_H$ domain; (vii) a dAb which consists of a VH or a VL domain; and (viii) an isolated complementarity determining region (CDR) or (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242, 423-426; and Huston et al. (1988) *Proc. Natl. Acad. Sci. USA* 85, 5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies can be prepared using any art recognized technique and those described herein such as, for example, a hybridoma method, as described by Kohler et al. (1975) *Nature*, 256:495, a transgenic animal, as described by, for example, (see e.g., Lonberg, et al. (1994) Nature 368(6474): 856-859), recombinant DNA methods (see, e.g., U.S. Pat. No. 4,816,567), or using phage antibody libraries using the techniques described in, for example, Clackson et al., *Nature*, 352:624-628 (1991) and Marks et al., *J. Mol. Biol.*, 222:581-597 (1991). Monoclonal antibodies include chimeric antibodies, human antibodies and humanized antibodies and may occur naturally or be recombinantly produced.

The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies may have variable and constant regions derived from human germline immunoglobulin sequences. In certain embodiments, however, such recombinant human antibodies can be subjected to in vitro mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

The term "human antibody," as used herein, is intended to include antibodies having variable regions in which both the framework and CDR regions are derived from human germline immunoglobulin sequences as described, for example, by Kabat et al. (See Kabat, et al. (1991) *Sequences of proteins of Immunological Interest, Fifth Edition*, U.S. Department of Health and Human Services, NIH Publication No. 91-3242). Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The human antibody can have at least one ore more amino acids replaced with an amino acid residue, e.g., an activity enhancing amino acid residue which is not encoded by the human germline immunoglobulin sequence. Typically, the human antibody can have up to twenty positions replaced with amino acid residues which are not part of the human germline immunoglobulin sequence. In a particular embodiment, these replacements are within the CDR regions as described in detail below.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, (1990) *Clin. Exp. Immunol.* 79, 315-321; Kostelny et al. (1992) *J. Immunol.* 148, 1547-1553. In a particular embodiment, a bispecific antibody according to the present invention includes binding sites for both ErbB3 and IGF1-R (i.e., insulin-like growth factor 1-receptor). In another embodiment, a bispecific antibody according to the present invention includes binding sites for both ErbB3 and C-MET. In other embodiments, a bispecific antibody includes a binding site for ErbB3 and a binding site for ErbB2, ErbB3, ErbB4, EGFR, Lewis Y, MUC-1, EpCAM, CA125, prostate specific membrane antigen, PDGFR-α, PDGFR-β, C-KIT, or any of the FGF receptors.

As used herein, a "heterologous antibody" is defined in relation to the transgenic non-human organism or plant producing such an antibody.

An "isolated antibody," as used herein, is intended to refer to an antibody which is substantially free of other antibodies having different antigenic specificities (e.g., an isolated antibody that specifically binds to ErbB3 is substantially free of antibodies that specifically bind antigens other than ErbB3). In addition, an isolated antibody is typically substantially free of other cellular material and/or chemicals. In one embodiment of the invention, a combination of "isolated" monoclonal antibodies having different ErbB3 binding specificities are combined in a well defined composition.

As used herein, "isotype" refers to the antibody class (e.g., IgM or IgG1) that is encoded by heavy chain constant region genes. In one embodiment, an antibody or antigen binding portion thereof is of an isotype selected from an IgG1, an IgG2, an IgG3, an IgG4, an IgM, an IgA1, an IgA2, an IgAsec, an IgD, or an IgE antibody isotype. In some embodiments, a monoclonal antibody of the invention is of the IgG1 isotype. In other embodiments, a monoclonal antibody of the invention is of the IgG2 isotype.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the non-switched isotype is typically the first CH gene immediately downstream from the functionally rearranged VDJ gene. Isotype switching has been classified as classical or non-classical isotype switching. Classical isotype switching occurs by recombination events which involve at least one switch sequence regions in a gene encoding an antibody. Non-classical isotype switching may occur by, for example, homologous recombination between human $\sigma_\mu$ and human $\Sigma_\mu$ ($\delta$-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a $\mu$ switch region, will be 5' (i.e., upstream) of the construct region to be deleted during the switch recombination. The "switch acceptor" region will be between the construct region to be deleted and the replacement constant region (e.g., $\gamma$, $\epsilon$, etc.). As there is no specific site where recombination always occurs, the final gene sequence will typically not be predictable from the construct.

An "antigen" is an entity (e.g., a proteinaceous entity or peptide) to which an antibody or antigen-binding portion thereof binds. In various embodiments of the present invention, an antigen is ErbB3 or a ErbB3-like molecule. In a particular embodiment according to the invention, an antigen is human ErbB3.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance. See, e.g., *Epitope Mapping Protocols in Methods in Molecular Biology*, Vol. 66, G. E. Morris, Ed. (1996).

Also encompassed by the present invention are antibodies that bind the same or an overlapping epitope as the antibodies of the present invention, i.e., antibodies that compete for binding to ErbB3, or bind epitopes which overlap with epitopes bound by the antibodies described herein, i.e., an epitope located on domain I of ErbB3. Antibodies that recognize the same epitope can be identified using routine techniques such as an immunoassay, for example, by showing the ability of one antibody to block the binding of another antibody to a target antigen, i.e., a competitive binding assay. Competitive binding is determined in an assay in which the immunoglobulin under test inhibits specific binding of a reference antibody to a common antigen, such as ErbB3. Numerous types of competitive binding assays are known, for example: solid phase direct or indirect radioimmunoassay (RIA), solid phase direct or indirect enzyme immunoassay (EIA), sandwich competition assay (see Stahli et al., (1983) *Methods in Enzymology* 9:242); solid phase direct biotin-avidin EIA (see Kirkland et al., (1986) *J. Immunol.* 137: 3614); solid phase direct labeled assay, solid phase direct labeled sandwich assay (see Harlow and Lane, (1988) *Antibodies: A Laboratory Manual*, Cold Spring Harbor Press); solid phase direct label RIA using 1-125 label (see Morel et al., (1988) *Mol. Immunol.* 25(1):7); solid phase direct biotin-avidin EIA (Cheung et al., (1990) *Virology* 176:546); and direct labeled RIA. (Moldenhauer et al., (1990) *Scand. J. Immunol.* 32:77). Typically, such an assay involves the use of purified antigen (e.g., ErbB3) bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

As used herein, the terms "specific binding," "specifically binds," "selective binding," and "selectively binds," mean that an antibody or antigen-binding portion thereof, exhibits appreciable affinity for a particular antigen or epitope and, generally, does not exhibit significant cross-reactivity with other antigens and epitopes. "Appreciable" or preferred binding includes binding with an affinity of at least $10^6$, $10^7$, $10^8$, $10^9$ $M^{-1}$, or $10^{10}$ $M^-$. Affinities greater than $10^7 M^{-1}$, preferably greater than $10^8$ $M^{-1}$ are more preferred. Values intermediate of those set forth herein are also intended to be within the scope of the present invention and a preferred binding affinity can be indicated as a range of affinities, for example, $10^6$ to $10^{10}$ $M^{-1}$, preferably $10^7$ to $10^{10}$ $M^{-1}$, more preferably $10^8$ to $10^{10}$ $M^-$. An antibody that "does not exhibit significant cross-reactivity" is one that will not appreciably bind to an undesirable entity (e.g., an undesirable proteinaceous entity). For example, in one embodiment, an antibody or antigen-binding portion thereof that specifically binds to ErbB3 will appreciably bind that ErbB3 molecule but will not significantly react with other ErbB molecules and non-ErbB proteins or peptides. Specific or selective binding can be determined according to any art-recognized means for determining such binding, including, for example, according to Scatchard analysis and/or competitive binding assays.

The term "$K_D$," as used herein, is intended to refer to the dissociation equilibrium constant of a particular antibody-antigen interaction or the affinity of an antibody for an antigen. In one embodiment, the antibody or antigen binding portion thereof according to the present invention binds an antigen (e.g., ErbB3) with an affinity ($K_D$) of 50 nM or better (i.e., or less) (e.g., 40 nM or 30 nM or 20 nM or 10 nM or less), as measured using a surface plasmon resonance assay or a cell binding assay. In a particular embodiment, an antibody or antigen binding portion thereof according to the present invention binds ErbB3 with an affinity ($K_D$) of 8 nM or better (e.g., 7 nM, 6 nM, 5 nM, 4 nM, 2 nM, 1.5 nM, 1.4 nM, 1.3 nM, 1 nM or less), as measured by a surface plasmon resonance assay or a cell binding assay. In other embodiments, an antibody or antigen binding portion thereof binds an antigen (e.g., ErbB3) with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 3000 instrument using recombinant ErbB3 as the analyte and the antibody as the ligand, and binds to the predetermined antigen with an affinity that is at least two-fold greater than its affinity for binding to a non-specific antigen (e.g., BSA, casein) other than the predetermined antigen or a closely-related antigen.

The term "$K_{off}$" as used herein, is intended to refer to the off rate constant for the dissociation of an antibody from the antibody/antigen complex.

The term "EC50," as used herein, refers to the concentration of an antibody or an antigen-binding portion thereof, which induces a response, either in an in vitro or an in vivo assay, which is 50% of the maximal response, i.e., halfway between the maximal response and the baseline.

As used herein, "glycosylation pattern" is defined as the pattern of carbohydrate units that are covalently attached to a protein, more specifically to an immunoglobulin protein.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody portions (e.g., $V_H$, $V_L$, CDR3) that bind to ErbB3, is intended to refer to a nucleic acid molecule in which the nucleotide sequences encoding the antibody or antibody portion are free of other nucleotide sequences encoding antibodies that bind antigens other than ErbB3, which other sequences may naturally flank the nucleic acid in human genomic DNA.

The term "modifying," or "modification," as used herein, is intended to refer to changing one or more amino acids in the antibodies or antigen-binding portions thereof. The change can be produced by adding, substituting or deleting an amino acid at one or more positions. The change can be produced using known techniques, such as PCR mutagenesis. For example, in some embodiments, an antibody or an antigen-binding portion thereof identified using the methods of the invention can be modified, to thereby modify the binding affinity of the antibody or antigen-binding portion thereof to ErbB3.

The present invention also encompasses "conservative amino acid substitutions" in the sequences of the antibodies of the invention, i.e., nucleotide and amino acid sequence modifications which do not abrogate the binding of the antibody encoded by the nucleotide sequence or containing the amino acid sequence, to the antigen, i.e., ErbB3. Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. Thus, a predicted nonessential amino acid residue in an anti-ErbB3 antibody is preferably replaced with another amino acid residue from the same class. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10): 879-884 (1999); and Burks et al. *Proc. Natl. Acad. Sci. USA* 94:.412-417 (1997)).

The term "non-conservative amino acid substitution" refers to the substitution of an amino acid in one class with an amino acid from another class; for example, substitution of an Ala, a class II residue, with a class III residue such as Asp, Asn, Glu, or Gln.

Alternatively, in another embodiment, mutations (conservative or non-conservative) can be introduced randomly along all or part of an anti-ErbB3 antibody coding sequence, such as by saturation mutagenesis, and the resulting modified anti-ErbB3 antibodies can be screened for binding activity.

A "consensus sequence" is a sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" of an immunoglobulin refers to a framework region in the consensus immunoglobulin sequence.

Similarly, the consensus sequence for the CDRs of can be derived by optimal alignment of the CDR amino acid sequences of ErbB3 antibodies of the present invention.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "operably linked" refers to a nucleic acid sequence placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The terms "treat," "treating," and "treatment," as used herein, refer to therapeutic or preventative measures described herein. The methods of "treatment" employ administration to a subject, an antibody or antigen binding portion of the present invention, for example, a subject having a disease or disorder associated with ErbB3 dependent signaling or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

The term "disease associated with ErbB3 dependent signaling," or "disorder associated with ErbB3 dependent signaling," as used herein, includes disease states and/or symptoms associated with a disease state, where increased levels of ErbB3 and/or activation of cellular cascades involving ErbB3 are found. It is understood that ErbB3 heterodimerizes with other ErbB proteins such as, EGFR and ErbB2, when increased levels of ErbB3 are found. Accordingly, the term "disease associated with ErbB3 dependent signaling," also includes disease states and/or symptoms associated with disease states where increased levels of EGFR/ErbB3 and/or ErbB2/ErbB3 heterodimers are found. In general, the term "disease associated with ErbB3 dependent signaling," refers to any disorder, the onset, progression or the persistence of the symptoms of which requires the participation of ErbB3. Exemplary ErbB3-mediated disorders include, but are not limited to, for example, cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma and various types of head and neck cancer. In a particular embodiment, a cancer treated or diagnosed using the methods of the present invention is selected from melanoma, breast cancer, ovarian cancer, renal carcinoma, gastrointestinal/colon cancer, lung cancer, and prostate cancer.

The term "KRAS mutation", as used herein, refers to mutations found in certain cancers in the human homolog of the v-Ki-ras2 Kirsten rat sarcoma viral oncogene. Non-limiting examples of human KRAS gene mRNA sequences include Genbank Accession Nos. NM_004985 and NM_033360. It has been reported that KRAS mutations are found in 73% of pancreatic tumors, 35% of colorectal tumors, 16% of ovarian tumors and 17% of lung tumors.

The term "PI3K mutation", as used herein, refers to mutations found in certain cancers in the phosphatidyl-inositol-3-kinase gene, typically leading to activation of PI3K in the cancer cells. It has been reported that PI3K mutations are found in 12% of colorectal tumors, 15% of head and neck tumors and 26% of breast tumors.

The term "effective amount," as used herein, refers to that amount of an antibody or an antigen binding portion thereof that binds ErbB3, which is sufficient to effect treatment, prognosis or diagnosis of a disease associated with ErbB3 dependent signaling, as described herein, when administered to a subject. A therapeutically effective amount will vary depending upon the subject and disease condition being treated, the weight and age of the subject, the severity of the disease condition, the manner of administration and the like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an antibody or antigen binding portion thereof, according to the invention. Dosage regimen may be adjusted to provide the optimum therapeutic response. An effective amount is also one in which any toxic or detrimental effects (i.e., side effects) of an antibody or antigen binding portion thereof are minimized and/or outweighed by the beneficial effects. Additional preferred dosages regimens are described further below in the section pertaining to pharmaceutical compositions.

The term "patient" includes human and other mammalian subjects that receive either prophylactic or therapeutic treatment.

As used herein, the term "subject" includes any human or non-human animal. For example, the methods and compositions of the present invention can be used to treat a subject having cancer. In a particular embodiment, the subject is a human. The term "non-human animal" includes all vertebrates, e.g., mammals and non-mammals, such as non-human primates, sheep, dog, cow, chickens, amphibians, reptiles, etc.

The term "sample" refers to tissue, body fluid, or a cell from a patient or a subject. Normally, the tissue or cell will be removed from the patient, but in vivo diagnosis is also contemplated. In the case of a solid tumor, a tissue sample can be taken from a surgically removed tumor and prepared for testing by conventional techniques. In the case of lymphomas and leukemias, lymphocytes, leukemic cells, or lymph tissues can be obtained and appropriately prepared. Other patient samples, including urine, tear drops, serum, cerebrospinal fluid, feces, sputum, cell extracts etc. can also be useful for particular tumors.

The terms "anti-cancer agent" and "antineoplastic agent" refer to drugs used to treat malignancies, such as cancerous growths. Drug therapy may be used alone, or in combination with other treatments such as surgery or radiation therapy. Several classes of drugs may be used in cancer treatment, depending on the nature of the organ involved. For example, breast cancers are commonly stimulated by estrogens, and may be treated with drugs which inactive the sex hormones. Similarly, prostate cancer may be treated with drugs that inactivate androgens, the male sex hormone. Anti-cancer agents of the present invention include, among others, the following agents:

| Anti-Cancer Agent | Comments | Examples |
| --- | --- | --- |
| Antibodies<br>(a) antibodies other than anti-ErbB3 antibodies; and<br>(b) anti-ErbB3 antibodies which bind different epitopes | Antibodies which bind IGF-1R (insulin-like growth factor type 1 receptor), which is expressed on the cell surface of must human cancers | A12 (fully humanized mAb)<br>19D12 (fully humanized mAb)<br>CP751-871 (fully humanized mAb)<br>H7C10 (humanized mAb)<br>alphaIR3 (mouse)<br>scFV/FC (mouse/human chimera)<br>EM/164 (mouse)<br>AMG 479 (fully humanized mAb; Amgen)<br>IMCA 12 (fully humanized mAb; Imclone)<br>NSC-742460 (Dyax)<br>MR-0646, F50035 (Pierre Fabre Medicament, Merck) |
| | Antibodies which bind EGFR (epidermal growth factor receptor); Mutations affecting EGFR expression or activity could result in cancer | Matuzumab (EMD72000)<br>Erbitux ®/Cetuximab (Imclone)<br>Vectibix ®/Panitumumab (Amgen)<br>mAb 806<br>Nimotuzumab (TheraCIM)<br>INCB7839 (Incyte)<br>Matuzumab (EMD72000)<br>Panitumumab (Vectibix ®; Amgen) |
| | Antibodies which bind cMET (Mesenchymal epithelial transition factor); a member of the MET family of receptor tyrosine kinases) | AVEO (AV299) (AVEO)<br>AMG102 (Amgen)<br>5D5 (OA-5D5) (Genentech) |
| | Anti-ErbB3 antibodies which bind different epitopes | Ab #14 (MM 121-14) described herein<br>1B4C3; 2D1D12 (U3 Pharma AG)<br>U3-1287/AMG888 (U3 Pharma/Amgen) |
| | Anti-ErbB2 (HER2) antibodies | Herceptin ® (trastuzumab; Genentech/Roche);<br>Omnitarg ® (pertuzumab; 2C4, R1273; Genentech/Roche) |
| Small Molecules Targeting IGF1R | IGF-1R (insulin-like growth factor type 1 receptor), which is expressed on the cell surface of must human cancers | NVP-AEW541-A<br>BMS-536,924 (1H-benzoimidazol-2-yl)-1H-pyridin-2-one)<br>BMS-554,417<br>Cycloligan<br>TAE226<br>PQ401 |
| Small Molecules Targeting EGFR | EGFR (epidermal growth factor receptor); Mutations affecting EGFR expression or activity could result in cancer | Iressa ®/Gefitinib (AstraZeneca)<br>CI-1033 (PD 183805) (Pfizer)<br>Lapatinib (GW-572016) (GlaxoSmithKline)<br>Tykerb ®/Lapatinib Ditosylate (SmithKline Beecham)<br>Tarceva ®/Erlotinib HCL (OSI-774) (OSI Pharma)<br>PKI-166 (Novartis)<br>PD-158780<br>EKB-569<br>Tyrphostin AG 1478(4-(3-Chloroanillino)-6,7-dimethoxyquinazoline) |
| Small Molecules Targeting ErbB2 | ErbB2, also known as HER2, a member of the ErbB family of receptors, which is expressed on certain cancer cells | HKI-272 (neratinib; Wyeth)<br>KOS-953 (tanespimycin; Kosan Biosciences) |
| Small Molecules Targeting cMET | cMET (Mesenchymal epithelial transition factor); a member of the MET family of receptor tyrosine kinases) | PHA665752<br>ARQ 197 (ArQule)<br>ARQ-650RP (ArQule) |
| Antimetabolites | An antimetabolite is a chemical with a similar structure to a substance (a metabolite) required for normal biochemical reactions, yet different enough to interfere with the normal functions of cells, including cell division. | Flourouracil (5-FU)<br>Capecitabine/XELODA ® (HLR Roche)<br>5-Trifluoromethyl-2'-deoxyuridine<br>Methotrexate sodium (Trexall) (Barr)<br>Raltitrexed/Tomudex ® (AstraZaneca)<br>Pemetrexed/Alimta ® (Lilly)<br>Tegafur<br>Cytosine Arabinoside (Cytarabine, Ara-C)/<br>Thioguanine ® (GlaxoSmithKline)<br>5-azacytidine<br>6-mercaptopurine (Mercaptopurine, 6-MP)<br>Azathioprine/Azasan ® (AAIPHARMA LLC)<br>6-thioguanine (6-TG)/Purinethol ® (TEVA)<br>Pentostatin/Nipent ® (Hospira Inc.)<br>Fludarabine phosphate/Fludara ® (Bayer Health Care) |

-continued

| Anti-Cancer Agent | Comments | Examples |
|---|---|---|
| | | Cladribine (2-CdA, 2-chlorodeoxyadenosine)/Leustatin ® (Ortho Biotech)<br>Floxuridine (5-fluoro-2)/FUDR ® (Hospira, Inc.) |
| Alkylating agents | An alkylating antineoplastic agent is an alkylating agent that attaches an alkyl group to DNA. Since cancer cells generally proliferate unrestrictively more than do healthy cells they are more sensitive to DNA damage, and alkylating agents are used clinically to treat a variety of tumours. | Ribonucleotide Reductase Inhibitor (RNR)<br>Cyclophosphamide/Cytoxan (BMS)<br>Neosar (TEVA)<br>Ifosfamide/Mitoxana ® (ASTA Medica)<br>Thiotepa (Bedford, Abraxis, Teva)<br>BCNU→ 1,3-bis(2-chloroethyl)-1-nitosourea<br>CCNU→ 1,-(2-chloroethyl)-3-cyclohexyl-1-nitrosourea (methyl CCNU)<br>Hexamethylmelamine (Altretamine, HMM)/Hexalen ® (MGI Pharma Inc.)<br>Busulfan/Myleran (GlaxoSmithKline)<br>Procarbazine HCL/<br>Matulane (Sigma Tau Pharmaceuticals, Inc.)<br>Dacarbazine (DTIC)<br>Chlorambucil/Leukaran ® (SmithKline Beecham)<br>Melphalan/Alkeran ® (GlaxoSmithKline)<br>Cisplatin (Cisplatinum, CDDP)/Platinol (Bristol Myers)<br>Carboplatin/Paraplatin (BMS)<br>Oxaliplatin/Eloxitan ® (Sanofi-Aventis US)<br>Bendamustine<br>Carboquone<br>Carmustine<br>Chloromethine<br>Dacarbazine (DTIC)<br>Fotemustine<br>Lomustine<br>Mannosulfan<br>Nedaplatin<br>Nimustine<br>Prednimustine<br>Ranimustine<br>Satraplatin<br>Semustine<br>Streptozocin<br>Temozolomide<br>Treosulfan<br>Triaziquone<br>Triethylene melamine<br>ThioTEPA (Bedford, Abraxis, Teva)<br>Triplatin tetranitrate<br>Trofosfamide<br>Uramustine |
| Topoisomerase inhibitors | Topoisomerase inhibitors are chemotherapy agents designed to interfere with the action of topoisomerase enzymes (topoisomerase I and II), which are enzymes that control the changes in DNA structure by catalyzing the breaking and rejoining of the phosphodiester backbone of DNA strands during the normal cell cycle. | Doxorubicin HCL/Doxil ® (Alza)<br>Daunorubicin citrate/Daunoxome ® (Gilead)<br>Mitoxantrone HCL/Novantrone (EMD Serono)<br>Actinomycin D<br>Etoposide/Vepesid ® (BMS)/Etopophos ® (Hospira, Bedford, Teva Parenteral, Etc.)<br>Topotecan HCL/Hycamtin ® (GlaxoSmithKline)<br>Teniposide (VM-26)/Vumon ® (BMS)<br>Irinotecan HCL(CPT-11)/<br>Camptosar ® (Pharmacia & Upjohn)<br>Camptothecin (CPT)<br>Belotecan<br>Rubitecan |
| Microtubule targeting agents | Microtubules are one of the components of the cytoskeleton. They have diameter of ~24 nm and length varying from several micrometers to possibly millimeters in axons of nerve cells. | Vincristine/Oncovin ® (Lilly)<br>Vinblastine sulfate/Velban ®(discontinued) (Lilly)<br>Vinorelbine tartrate/Navelbine ® (PierreFabre)<br>Vindesine sulphate/Eldisine ® (Lilly)<br>Paclitaxel/Taxol ® (BMS)<br>Docetaxel/Taxotere ® (Sanofi Aventis US) |

| Anti-Cancer Agent | Comments | Examples |
|---|---|---|
| | Microtubules serve as structural components within cells and are involved in many cellular processes including mitosis, cytokinesis, and vesicular transport. | Nanoparticle paclitaxel (ABI-007)/Abraxane ® (Abraxis BioScience, Inc.)<br>Ixabepilone/IXEMPRA ™ (BMS)<br>Larotaxel<br>Ortataxel<br>Tesetaxel<br>Vinflunine |
| Kinase inhibitors | Tyrosine kinases are enzymes within the cell that function to attach phosphate groups to the amino acid tyrosine. By blocking the ability of protein tyrosine kinases to function, these compounds provide a tool for controlling cancerous cell growth. | Imatinib mesylate/Gleevec (Novartis)<br>Sunitinib malate/Sutent ® (Pfizer)<br>Sorafenib tosylate/Nexavar ® (Bayer)<br>Nilotinib hydrochloride monohydrate/Tasigna ® (Novartis)<br>AMG 386 (Amgen)<br>Axitinib (AG-013736; Pfizer, Inc.)<br>Bosutinib (SKI-606; Wyeth)<br>Brivanib alalinate (BMS-582664; BMS)<br>Cediranib (AZD2171; Recentin, AstraZeneca)<br>Dasatinib (BMS-354825: Sprycel ®; BMS)<br>Lestaurtinib (CEP-701; Cephalon)<br>Motesanib diphosphage (AMG-706; Amgen/Takeda)<br>Pazopanib HCL (GW786034; Armala, GSK)<br>Semaxanib (SU5416; Pharmacia)<br>Vandetanib (AZD647; Zactima; AstraZeneca)<br>Vatalanib (PTK-787; Novartis, Bayer Schering Pharma)<br>XL184 (NSC718781; Exelixis, GSK) |
| Protein synthesis inhibitors | Induces cell apoptosis | L-asparaginase/Elspar ® (Merck & Co.) |
| Somatostatin analogue | | Octreotide acetate (Sandostatin ®; Novartis) |
| Immunotherapeutic agents | Induces cancer patients to exhibit immune responsiveness | Alpha interferon<br>Angiogenesis Inhibitor/Avastin ® (Genentech)<br>IL-2→ Interleukin 2 (Aldesleukin)/Proleukin ® (Chiron)<br>IL-12→ Interleukin 12 |
| Hormones | Hormone therapies associated with menopause and aging seek to increase the amount of certain hormones in your body to compensate for age- or disease-related hormonal declines. Hormone therapy as a cancer treatment either reduces the level of specific hormones or alters the cancer's ability to use these hormones to grow and spread. | Toremifene citrate/Fareston ® (GTX, Inc.)<br>Fulvestrant/Faslodex ® (AstraZeneca)<br>Raloxifene HCL/Evista ® (Lilly)<br>Anastrazole/Arimidex ® (AstraZeneca)<br>Letrozole/Femara ® (Novartis)<br>Fadrozole (CGS 16949A)<br>Exemestane/Aromasin ® (Pharmacia & Upjohn)<br>Leuprolide acetate/Eligard ® (QTL USA)<br>Lupron ® (TAP Pharm.)<br>Goserelin acetate/Zoladex ® (AstraZeneca)<br>Triptorelin pamoate/Trelstar ® (Watson Labs)<br>Buserelin/Suprefact ® (Sanofi Aventis)<br>Nafarelin<br>Cetrorelix/Cetrotide ® (EMD Serono)<br>Bicalutamide/Casodex ® (AstraZeneca)<br>Nilutamide/Nilandron ® (Aventis Pharm.)<br>Megestrol acetate/Megace ® (BMS)<br>Somatostatin Analogs (Octreotide acetate/Sandostatin ® (Novartis))<br>Abarelix (Plenaxis ™; Amgen)<br>Abiraterone acetate (CB7630; BTG plc)<br>Afimoxifene (TamoGel; Ascend Therapeutics, Inc.)<br>Aromatase inhibitor (Atamestane plus toremifene; Intarcia Therapeutics, Inc.)<br>Arzoxifene (Eli Lilly & Co)<br>Asentar; DN-101 (Novartis; Oregon Health & Science U)<br>Flutamide (Eulexin ®, Schering; Prostacur, Laboratories Almirall, S.A)<br>Letrozole (CGS20267) (Femara, Chugai; Estrochek, Jagsonpal Pharmaceuticals Ltd;)<br>Magestrol acetate (Estradiol Valerate (Delestrogen) Jagsonpal Pharmaceuticals Ltd)<br>Medroxyprogesterone acetate (Veraplex; Combiphar) |

-continued

| Anti-Cancer Agent | Comments | Examples |
|---|---|---|
| | | MT206 (Medisyn Technologies, Inc.)<br>Nandrolone decanoate (Zestabolin; Mankind Pharma Ltd)<br>Tamoxifen (Taxifen, Yung Shin Pharmaceutical; Tomifen, Alkem Laboratories Ltd.)<br>Tamoxifen citrate (Nolvadex, AstraZeneca; Soltamox, EUSA Pharma Inc; Tamoxifen citrate SOPHARMA, Sopharma JSCo.) |
| Glucocorticoids | Anti-inflammatory drugs used to reduce swelling that causes cancer pain. | Predinsolone<br>Dexamethasone/Decadron ® (Wyeth)<br>Prednisone (Deltasone, Orasone, Liquid Pred, Sterapred ®) |
| Aromatose inhibitors | Includes imidazoles | Ketoconazole |
| mTOR inhibitors | The mTOR signaling pathway was originally discovered during studies of the immunosuppressive agent rapamycin. This highly conserved pathway regulates cell proliferation and metabolism in response to environmental factors, linking cell growth factor receptor signaling via phosphoinositide-3-kinase (PI-3K) to cell growth, proliferation, and angiogenesis. | Sirolimus (Rapamycin)/<br>Rapamune ® (Wyeth)<br>Temsirolimus (CCI-779)/Torisel ® (Wyeth)<br>Deforolimus (AP23573) (Ariad Pharm.)<br>Everolimus (RAD001)/Certican ® (Novartis) |
| Chemotherapeutic agents | | Adriamycin, 5-Fluorouracil, Cytoxin, Bleomycin, Mitomycin C, Daunomycin, Carminomycin, Aminopterin, Dactinomycin, Mitomycins, Esperamicins, Clofarabine, Mercaptopurine, Pentostatin, Thioguanine, Cytarabine, Decitabine, Floxuridine, Gemcitabine (Gemzar), Enocitabine, Sapacitabine |
| Protein Kinase B (PKB) Inhibitors | | Akt Inhibitor ASTEX (Astex Therapeutics)<br>Akt Inhibitors NERVIANO (Nerviano Medical Sciences)<br>AKT Kinase Inhibitor TELIK (Telik Inc)<br>AKT DECIPHERA (Deciphera Pharmaceuticals, LLC)<br>Perifosine (KRX0401, D-21266; Keryx Biopharmaceuticals Inc, AEterna Zentaris Inc)<br>Perifosine with Docetaxel (Keryx Biopharmaceuticals Inc, AEterna Zentaris Inc)<br>Perifosine with Gemcitabine (AEterna Zentaris Inc)<br>Perifosine with Paclitaxel (AEterna Zentaris Inc)<br>Protein Kinase-B inhibitor DEVELOGEN (DeveloGen AG)<br>PX316 (Oncothyreon, Inc.)<br>RX0183 (Rexahn Pharmaceuticals Inc)<br>RX0201 (Rexahn Pharmaceuticals Inc)<br>VQD002 (VioQuest Pharmaceuticals Inc)<br>XL418 (Exelixis Inc)<br>ZEN027 (AEterna Zentaris Inc) |
| Phosphatidylinositol 3-Kinase (PI3K) Inhibitors | | BEZ235 (Novartis AG)<br>BGT226 (Novartis AG)<br>CAL101 (Calistoga Pharmaceuticals, Inc.)<br>CHR4432 (Chroma Therapeutics Ltd)<br>Erk/PI3K Inhibitors ETERNA (AEterna Zentaris Inc)<br>GDC0941 (Genentech Inc/Piramed Limited/Roche Holdings Ltd)<br>Enzastaurin HCL (LY317615; Enzastaurin; Eli Lilly)<br>LY294002/Wortmannin<br>PI3K Inhibitors SEMAFORE (Semafore Pharmaceuticals)<br>PX866 (Oncothyreon, Inc.) |

| Anti-Cancer Agent | Comments | Examples |
| --- | --- | --- |
| | | SF1126 (Semafore Pharmaceuticals) |
| | | VMD-8000 (VM Discovery, Inc.) |
| | | XL147 (Exelixis Inc) |
| | | XL147 with XL647 (Exelixis Inc) |
| | | XL765 (Exelixis Inc) |
| | | PI-103 (Roche/Piramed) |
| Cyclin Dependent Kinase Inhibitors | | CYC200, r-roscovitine (Seliciclib; Cyclacel Pharma) |
| | | NSC-649890, L86-8275, HMR-1275 (Alvocidib; NCI) |
| TLr9, CD289 | | IMOxine (Merck KGaA) |
| | | HYB2055 (Idera) |
| | | IMO-2055 (Isis Pharma) |
| | | 1018 ISS (Dynavax Technologies/UCSF) |
| | | PF-3512676 (Pfizer) |
| Enzyme Inhibitor | | Lonafarnib(SCH66336; Sarasar; SuperGen, U Arizona) |
| Anti-TRAIL | | AMG-655 (Aeterna Zentaris, Keryx Biopharma) |
| | | Apo2L/TRAIL, AMG951 (Genentech, Amgen) |
| | | Apomab (fully humanized mAb; Genentech) |
| MEK Inhibitors | [Mitogen-Activated Protein Kinase Kinase 1 (MAP2K1); Mitogen-Activated Protein Kinase Kinase 2 (MAP2K2)] | ARRY162 (Array BioPharma Inc) |
| | | ARRY704 (Array BioPharma Inc) |
| | | ARRY886 (Array BioPharma Inc) |
| | | AS703026 (Merck Serono S.A) |
| | | AZD6244 (AstraZeneca Plc) |
| | | AZD8330 (AstraZeneca Plc) |
| | | RDEA119 (Ardea Biosciences, Inc.) |
| | | RDEA436 (Ardea Biosciences, Inc.) |
| | | XL518 (Exelixis Inc; Genentech Inc) |
| Miscellaneous Inhibitors | | Imprime PGG (Biothera) |
| | | CHR-2797 (AminopeptidaseM1 inhibitor; Chroma Therapeutics) |
| | | E7820, NSC 719239 (Integrin-alpha2 inhibitor, Eisai) |
| | | INCB007839 (ADAM 17, TACE Inhibitor; Incyte) |
| | | CNF2024,BIIB021 (Hsp90 Inhibitor; Biogen Idec) |
| | | MP470, HPK-56 (Kit/Mel/Ret Inhibitor; Shering-Plough) |
| | | SNDX-275/MS-275 (HDAC Inhibitor; Syndax) |
| | | Zarnestra,Tipifarnib, R115777 (Ras Inhibitor; Janssen Pharma) |
| | | Volociximab; Eos 200-4,M200 (alpha581 integrin inhibitor; Biogen Idec; Eli Lilly/UCSF/PDL BioPharma) |
| | | Apricoxib (TP2001; COX-2 Inhibitor, Daiichi Sankyo; Tragara Pharma) |

One or more anti-cancer agents may be administered either simultaneously or before or after administration of an antibody or antigen binding portion thereof of the present invention.

Various aspects of the invention are described in further detail in the following subsections.

II. Methods for Producing Antibodies of the Invention (i) Monoclonal Antibodies Monoclonal antibodies of the invention can be produced using a variety of known techniques, such as the standard somatic cell hybridization technique described by Kohler and Milstein (1975) *Nature* 256: 495, viral or oncogenic transformation of B lymphocytes or phage display technique using libraries of human antibody genes. In particular embodiments, the antibodies are fully human monoclonal antibodies.

Accordingly, in one embodiment, a hybridoma method is used for producing an antibody that binds ErbB3. In this method, a mouse or other appropriate host animal can be immunized with a suitable antigen in order to elicit lymphocytes that produce or are capable of producing antibodies that will specifically bind to the antigen used for immunization. Alternatively, lymphocytes may be immunized in vitro. Lymphocytes can then be fused with myeloma cells using a suitable fusing agent, such as polyethylene glycol, to form a hybridoma cell (Goding, Monoclonal Antibodies: Principles and Practice, pp. 59-103 (Academic Press, 1986)). Culture medium in which hybridoma cells are growing is assayed for production of monoclonal antibodies directed against the antigen. After hybridoma cells are identified that produce antibodies of the desired specificity, affinity, and/or activity, the clones may be subcloned by limiting dilution procedures and grown by standard methods (Goding, Monoclonal Antibodies:Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography.

In another embodiment, antibodies and antibody portions that bind ErbB3 can be isolated from antibody phage libraries generated using the techniques described in, for example, McCafferty et al., *Nature,* 348:552-554 (1990). Clackson et al., Nature, 352:624-628 (1991), Marks et al., *J. Mol. Biol.,* 222:581-597 (1991) and Hoet et al (2005) *Nature Biotechnology* 23, 344-348; U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al. Additionally, production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.,* 21:2265-2266 (1993)) may also be used.

In a particular embodiment, the monoclonal antibody or antigen binding portion thereof that binds ErbB3 is produced using the phage display technique described by Hoet et al., supra. This technique involves the generation of a human Fab library having a unique combination of immunoglobulin sequences isolated from human donors and having synthetic diversity in the heavy-chain CDRs is generated. The library is then screened for Fabs that bind to ErbB3.

In yet another embodiment, human monoclonal antibodies directed against ErbB3 can be generated using transgenic or transchromosomic mice carrying parts of the human immune system rather than the mouse system (see e.g., Lonberg, et al. (1994) Nature 368(6474): 856-859; Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.).

In another embodiment, human antibodies of the invention can be raised using a mouse that carries human immunoglobulin sequences on transgenes and transchomosomes, such as a mouse that carries a human heavy chain transgene and a human light chain transchromosome (see e.g., PCT Publication WO 02/43478 to Ishida et al.).

Still further, alternative transgenic animal systems expressing human immunoglobulin genes are available in the art and can be used to raise anti-ErbB3 antibodies of the invention. For example, an alternative transgenic system referred to as the Xenomouse (Abgenix, Inc.) can be used; such mice are described in, for example, U.S. Pat. Nos. 5,939,598; 6,075, 181; 6,114,598; 6,150,584 and 6,162,963 to Kucherlapati et al.

Moreover, alternative transchromosomic animal systems expressing human immunoglobulin genes are available in the art and can be used to raise anti-ErbB3 antibodies of the invention. For example, mice carrying both a human heavy chain transchromosome and a human light chain tranchromosome can be used; as described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-ErbB3 antibodies of the invention.

In yet another embodiment, antibodies of the present invention can be prepared using a transgenic plant and/or cultured plant cells (such as, for example, tobacco, maize and duckweed) that produce such antibodies. For example, transgenic tobacco leaves expressing antibodies or antigen binding portions thereof can be used to produce such antibodies by, for example, using an inducible promoter (see, e.g., Cramer et al., *Curr. Top. Microbol. Immunol.* 240:95 118 (1999)). Also, transgenic maize can be used to express such antibodies and antigen binding portions thereof (see, e.g., Hood et al., *Adv. Exp. Med. Biol.* 464:127 147 (1999)). Antibodies can also be produced in large amounts from transgenic plant seeds including antibody portions, such as single chain antibodies (scFv's), for example, using tobacco seeds and potato tubers (see, e.g., Conrad et al., *Plant Mol. Biol.* 38:101 109 (1998)). Methods of producing antibodies or antigen binding portions in plants can also be found in, e.g., Fischer et al., *Biotechnol. Appl. Biochem.* 30:99 108 (1999), Ma et al., *Trends Biotechnol.* 13:522 7 (1995); Ma et al., *Plant Physiol.* 109:341 6 (1995); Whitelam et al., *Biochem. Soc. Trans.* 22:940 944 (1994) and U.S. Pat. Nos. 6,040,498 and 6,815,184.

The binding specificity of monoclonal antibodies or portions thereof that bind ErbB3 prepared using any technique including those disclosed here, can be determined by immunoprecipitation or by an in vitro binding assay, such as radioimmunoas say (RIA) or enzyme-linked immunoabsorbent assay (ELISA). The binding affinity of a monoclonal antibody or portion thereof also can be determined by the Scatchard analysis of Munson et al., *Anal. Biochem.,* 107:220 (1980).

In certain embodiments, an ErbB3 antibody or portion thereof produced using any of the methods discussed above may be further altered or optimized to achieve a desired binding specificity and/or affinity using art recognized techniques, such as those described herein.

In one embodiment, partial antibody sequences derived from an ErbB3 antibody may be used to produce structurally and functionally related antibodies. For example, antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, *Nature* 332:323-327; Jones, P. et al., 1986, *Nature* 321:522-525; and Queen, C. et al., 1989, *Proc. Natl. Acad. See. U.S.A.* 86:10029-10033). Such framework sequences can be obtained from public DNA databases that include germline antibody gene sequences.

Thus, one or more structural features of an anti-ErbB3 antibody of the invention, such as the CDRs, can be used to create structurally related anti-ErbB3 antibodies that retain at least one functional property of the antibodies of the invention, e.g., inhibiting EGF-like ligand mediated phosphorylation of ErbB3; inhibiting one or more of heregulin, epiregulin, epigen or biregulin-mediated signaling through ErbB3;

inhibiting proliferation or cells expressing ErbB3; and/or decreasing levels of ErbB3 on cell surfaces.

In a particular embodiment, one or more CDR regions selected from SEQ ID NOs:7-12, SEQ ID NOs:13-18, SEQ ID NOs:19-24, SEQ ID NOs:39-44, and SEQ ID NOs:45-50 is combined recombinantly with known human framework regions and CDRs to create additional, recombinantly-engineered, anti-ErbB3 antibodies of the invention. The heavy and light chain variable framework regions can be derived from the same or different antibody sequences.

It is well known in the art that antibody heavy and light chain CDR3 domains play a particularly important role in the binding specificity/affinity of an antibody for an antigen (see, Hall et al., *J. Imunol.*, 149:1605-1612 (1992); Polymenis et al., *J. Immunol.*, 152:5318-5329 (1994); Jahn et al., *Immunobiol.*, 193:400-419 (1995); Klimka et al., *Brit. J. Cancer,* 83:252-260 (2000); Beiboer et al., *J. Mol. Biol,* 296:833-849 (2000); Rader et al., *Proc. Natl. Acad. Sci. USA,* 95:8910-8915 (1998); Barbas et al., *J. Am. Chem. Soc.,* 116:2161-2162 (1994); Ditzel et al., *J. Immunol.,* 157:739-749 (1996)). Accordingly, in certain embodiments, antibodies are generated that include the heavy and/or light chain CDR3s of the particular antibodies described herein (e.g., SEQ ID NOs:9, 15, 21, 41, 47 and/or SEQ ID NOs:12, 18, 24, 44, 50). The antibodies can further include the heavy and/or light chain CDR1 and/or CDR2s of the antibodies of the present invention (e.g., SEQ ID NOs:7-8 and/or SEQ ID NOs:10-11; SEQ ID NOs:13-14 and/or SEQ ID NOs:16-17; SEQ ID NOs:20-21 and/or SEQ ID NOs:22-23; SEQ ID NOs:39-40 and/or SEQ ID NOs:42-43; or SEQ ID NOs:45-46 and/or SEQ ID NOs:48-49).

The CDR1, 2, and/or 3 regions of the engineered antibodies described above can comprise the exact amino acid sequence(s) as those disclosed herein (e.g., CDRs of Ab #6, Ab #3, Ab #14, Ab #17, or Ab #19, set forth in SEQ ID NOs:7-12, 13-18, 19-24, 39-44, and 45-50, respectively). However, the ordinarily skilled artisan will appreciate that some deviation from the exact CDR sequences may be possible while still retaining the ability of the antibody to bind ErbB3 effectively (e.g., conservative amino acid substitutions). Accordingly, in another embodiment, the engineered antibody may be composed of one or more CDRs that are, for example, 90%, 95%, 98%, 99% or 99.5% identical to one or more CDRs of Ab #6, Ab #3 or Ab #14.

In another embodiment, one or more residues of a CDR may be altered to modify binding to achieve a more favored on-rate of binding. Using this strategy, an antibody having ultra high binding affinity of, for example, $10^{10}$ $M^{-1}$ or more, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

In addition to, or instead of, modifications within the CDRs, modifications can also be made within one or more of the framework regions, FR1, FR2, FR3 and FR4, of the heavy and/or the light chain variable regions of an antibody, so long as these modifications do not eliminate the binding affinity of the antibody.

In another embodiment, the antibody is further modified with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

Also encompassed by the present invention are bispecific antibodies and immunoconjugates, as discussed below.

(ii) Bispecific Antibodies

Bispecific antibodies of the present invention include at least one binding specificity for ErbB3 and at least one binding specificity for another antigen, such as the product of an oncogene. Bispecific antibodies can be prepared as full length antibodies or antibody fragments (e.g. F(ab')$_2$ bispecific antibodies).

Methods for making bispecific antibodies are well known in the art (see, e.g., WO 05117973 and WO 06091209). For example, production of full length bispecific antibodies can be based on the coexpression of two immunoglobulin heavy chain-light chain pairs, where the two chains have different specificities (see, e.g., Millstein et al., *Nature,* 305:537-539 (1983)). Further details of generating bispecific antibodies can be found, for example, in Suresh et al., *Methods in Enzymology,* 121:210 (1986) and in Brennan et al., *Science,* 229: 81 (1985), which describes a chemical linkage process for making bispecific antibodies. Various techniques for making and isolating bispecific antibody fragments directly from recombinant cell culture have also been described. For example, bispecific antibodies have been produced using leucine zippers (see, e.g., Kostelny et al., *J. Immunol.,* 148(5): 1547-1553 (1992)). Another strategy for making bispecific antibody fragments by the use of single-chain Fv (sFv) dimers has also been reported (see, e.g., Gruber et al., *J. Immunol.,* 152:5368 (1994)).

In a particular embodiment, the bispecific antibody comprises a first antibody or binding portion thereof which binds to ErbB3 and a second antibody or binding portion thereof which binds to ErbB2, ERbB3, ErbB4, EGFR, IGF1-R, C-MET, Lewis Y, MUC-1, EpCAM, CA125, prostate specific membrane antigen, PDGFR-α, PDGFR-β, C-KIT, or any of the FGF receptors.

(iii) Immunoconjugates

Immunoconjugates of the present invention can be formed by conjugating the antibodies or antigen binding portions thereof described herein to another therapeutic agent. Suitable agents include, for example, a cytotoxic agent (e.g., a chemotherapeutic agent), a toxin (e.g. an enzymatically active toxin of bacterial, fungal, plant or animal origin, or fragments thereof), and/or a radioactive isotope (i.e., a radioconjugate). Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugated anti-ErbB3 antibodies. Examples include $^{212}$Bi, $^{131}$I, $^{131}$In, $^{90}$Y and $^{186}$Re.

Immunoconjugates of the invention can be made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody (see, e.g., WO94/11026).

III. Methods for Screening Antibodies of the Invention

Subsequent to producing antibodies or antigen binding portions that bind ErbB3, such antibodies, or portions thereof, can be screened for various properties, such as those described herein, using a variety of assays that are well known in the art.

In one embodiment, the antibodies or antigen binding portions thereof are screened for the ability to inhibit EGF-like ligand mediated phosphorylation of ErbB3. This can be done by treating cells expressing ErbB3 with an EGF-like ligand in the presence and absence of the antibody or antigen binding portion thereof. The cells can then be lysed and the crude lysates can be centrifuged to remove insoluble material. ErbB3 phosphorylation can be measured, for example, by Western blotting followed by probing with an anti-phosphotyrosine antibody as described in Kim et al., supra and the Examples below.

In other embodiments, the antibodies and antigen binding portions are further screened for one or more of the following properties: (1) inhibition of ErbB3-ligand (e.g., heregulin, epiregulin, epigen or biregulin) mediated signaling through ErbB3; (2) inhibition of proliferation of cells expressing ErbB3; (3) the ability to decrease levels of ErbB3 on cell surface (e.g., by inducing internalization of ErbB3), (4) inhibition of VEGF secretion of cells expressing ErbB3; (5) inhibition of the migration of cells expressing ErbB3; (6) inhibition of spheroid growth of cells expressing ErbB3; and/or (7) binding to an epitope located on domain I of ErbB3, each of which can be readily measured using art recognized techniques and those discussed herein.

Inhibition of one or more of heregulin, epiregulin, epigen or biregulin-mediated signaling through ErbB3 can be readily measured using routine assays, such as, described in Horst et al. supra. For example, the ability of an antibody or antigen binding portion thereof to inhibit heregulin, epiregulin, epigen or biregulin-mediated signaling through ErbB3 can be measured by kinase assays for known substrates of ErbB3 such as, for example, SHC and PI3K, as described in, for example, Horst et al. supra, Sudo et al., (2000) *Methods Enzymol*, 322:388-92; and Morgan et al. (1990) *Eur. J. Biochem.*, 191:761-767, following stimulation by one or more of heregulin, epiregulin, epigen or biregulin. Accordingly, cells expressing ErbB3 can be stimulated with one or more of heregulin, epiregulin, epigen or biregulin, and incubated with a candidate antibody or antigen-binding portion thereof. Cell lysates subsequently prepared from such cells can be immunoprecipitated with an antibody for a substrate of ErbB3 (or a protein in a cellular pathway involving ErbB3) such as, for example, an anti-JNK-1 antibody, and assayed for kinase activity (e.g., JNK kinase activity or PI3-kinase activity) using art recognized techniques. A decrease in or complete disappearance in level or activity (e.g., kinase activity) of a ErbB3 substrate or protein in a pathway involving ErbB3 in the presence of the antibody or antigen binding portion thereof, relative to the level or activity in the absence of the antibody or antigen binding portion thereof, is indicative of an antibody or antigen binding portion which inhibits one or more of heregulin, epiregulin, epigen or biregulin-mediated signaling.

In certain embodiments, the antibody or antigen binding portion thereof inhibits ErbB3-ligand (e.g., heregulin, epiregulin, epigen or biregulin) mediated signaling by decreasing the binding of one or more of heregulin, epiregulin, epigen or biregulin to ERbB3.

In order to select for those antibodies or antigen binding portions thereof which inhibit the binding of one or more of heregulin, epiregulin, epigen or biregulin to ErbB3, cells which express ErbB3 (e.g. MALME-3M cells, as described in the Examples infra), can be contacted with a labeled ErbB3-ligand (e.g., radiolabeled heregulin, epiregulin, epigen or biregulin) in the absence (control) or presence of the anti-ErbB3 antibody or antigen binding portion thereof. If the antibody or antigen binding portion thereof inhibits heregulin, epiregulin, epigen or biregulin binding to ErbB3, then a statistically significantly decrease in the amount of label recovered (e.g., radiolabeled heregulin, epiregulin, epigen or biregulin), relative to the amount in the absence of the antibody or antigen binding portion thereof, will be observed.

The antibody or antigen binding portion thereof may inhibit the binding of the ErbB3-ligand (e.g., heregulin, epiregulin, epigen or biregulin) by any mechanism. For example, the antibody or antigen binding portion thereof may inhibit binding of the ErbB3 ligand (e.g., one or more of heregulin, epiregulin, epigen or biregulin) to ErbB3 by binding to the same site or an overlapping site on ErbB3 as the ErbB3 ligand. Alternatively, the antibody or antigen binding portion thereof may inhibit binding of an ErbB3 ligand by altering or distorting the conformation of ErbB3, such that it is unable to bind to the ErbB3 ligand.

Antibodies and antigen binding portions thereof that decrease levels of ErbB3 on cell surfaces can be identified by their ability to downregulate ErbB3 on tumor cells. In certain embodiments, the antibodies or antigen binding portions thereof decrease ErbB3 cell surface expression by inducing internalization (or increasing endocytosis) of Erbb3. To test this, ErbB3 can be biotinylated and the number of ErbB3 molecules on the cell surface can be readily determined, for example, by measuring the amount of biotin on a monolayer of cells in culture in the presence or absence of an antibody or antigen binding portion thereof, for example, as described in, e.g., Waterman et al., J. Biol. Chem. (1998), 273:13819-27, followed by immunoprecipitation of ErbB3 and probing with streptavidin. A decrease in detection of biotinylated ErbB3 over time in the presence of an antibody or antigen binding portion is indicative of an antibody which decreases ErbB3 levels on cell surfaces.

Antibodies or antigen binding portions thereof of the present invention can also be tested for their ability to inhibit proliferation of cells expressing ErbB3, for example, tumor cells, using art recognized techniques, such as the Cell Titer Glow Assay described in the Examples below (also see, e.g., Macallan et al., *Proc. Natl. Acad. Sci.* (1998) 20; 95(2):708-13; Perez et al. (1995) *Cancer Research* 55, 392-398).

In another embodiment, the antibodies or antigen binding portions thereof are screened for the ability to inhibit VEGF secretion of cells expressing ErbB3. This can be done by using well-known assays, such as the VEGF ELISA kit available from R&D Systems (Minneapolis, Minn., Cat. #DY293B). Similarly, the antibodies or portions can be screened for the ability to inhibit the migration of cells expressing ErbB3 (e.g., MCF-7 cells) using a trans-well assay (Millipore Corp., Billerica, Mass., Cat #ECM552) as described herein.

In another embodiment, the antibodies or antigen binding portions thereof are screened for the ability to inhibit spheroid growth of cells expressing ErbB3. This can be done by using an assay which approximates conditions of a developing tumor growth (see, e.g., Herman et al. (2007) Journal of Biomolecular Screening Electronic publication) as described herein.

Antibodies or antigen binding portions thereof that bind to the same or overlapping epitopes as one or more antibodies of the present invention can also be identified using standard techniques known in the art and described herein. For example, in order to screen for antibodies which bind to the same or an overlapping epitope on ErbB3 bound by an antibody of interest, a cross-blocking assay, such as that described in *Antibodies*, A Laboratory Manual, Cold Spring Harbor Laboratory, Ed Harlow and David Lane (1988), can be performed.

IV. Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. In one embodiment, the compositions include a combination of multiple (e.g., two or more) isolated antibodies of the invention, which bind different epitopes on ErbB3.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Pharmaceutical compositions of the invention can be administered alone or in combination therapy, i.e., combined with other agents. For example, the combination therapy can include a composition of the present invention with at least one or more additional therapeutic agents, such as the anti-cancer agents described infra. The pharmaceutical compositions of the invention can also be administered in conjunction with radiation therapy and/or surgery.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the human antibodies of the invention may be administered once or twice weekly by subcutaneous injection or once or twice monthly by subcutaneous injection.

Non-limiting examples of suitable dosage ranges and regiments include 2-50 mg/kg (body weight of the subject) administered once a week, or twice a week or once every three days, or once every two weeks, and 1-100 mg/kg administered once a week, or twice a week or once every three days, or once every two weeks. In various embodiments, an antibody is administered at a dosage of 3.2 mg/kg, 6 mg/kg, 10 mg/kg, 15 mg/kg, 20 mg/kg, 25 mg/kg, 30 mg/kg, 35 mg/kg or 40 mg/kg at a timing of once a week, or twice a week or once every three days, or once every two weeks. Additional dosage ranges include: 1-1000 mg/kg, 1-500 mg/kg, 1-400 mg/kg, 1-300 mg/kg and 1-200 mg/kg. Suitable dosage schedules include once every three days, once every five days, once every seven days (i.e., once a week), once every 10 days, once every 14 days (i.e., once every two weeks), once every 21 days (i.e., once every three weeks), once every 28 days (i.e., once every four weeks) and once a month.

As demonstrated in the Examples, use of an antibody of the invention in combination with an additional therapeutic agent can lead to an additive effect for anti-tumor activity. Accordingly, for combination therapy, suboptimal dosages of the antibody or the second therapeutic agent, or both, can be used to achieve a desired therapeutic outcome due to the additive effects of the agents. For example, when use d in combination with another therapeutic agent, in various embodiments an antibody of the invention may be administered at a dosage that is 90%, or 80%, or 70% or 60% or 50% of the dosage used when the antibody is administered alone.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred per cent, this amount will range from about 0.001 per cent to about ninety percent of active ingredient, preferably from about 0.005 per cent to about 70 per cent, most preferably from about 0.01 per cent to about 30 per cent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Particular examples of adjuvants which are well-known in the art include, for example, inorganic adjuvants (such as aluminum salts, e.g., aluminum phosphate and aluminumhydroxide), organic adjuvants (e.g., squalene), oil-based adjuvants, virosomes (e.g., virosomes which contain a membrane-bound heagglutinin and neuraminidase derived from the influenza virus).

Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medications through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) Am. J. Physiol. 1233:134), different species of which may comprise the formulations of the inventions, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

V. Methods of Using Antibodies of the Invention

The present invention also provides methods of using antibodies and antigen-binding portions thereof that bind ErbB3 in a variety of ex vivo and in vivo diagnostic and therapeutic applications. For example, antibodies of the invention can be used for treating a disease associated with ErbB3 dependent signaling, including a variety of cancers.

In one embodiment, the present invention provides a method for treating a disease associated with ErbB3 dependent signaling by administering to a subject an antibody or antigen binding portion thereof of the invention in an amount effective to treat the disease. Suitable diseases include, for example, a variety of cancers including, but not limited to, melanoma, breast cancer, ovarian cancer, renal carcinoma, gastrointestinal cancer, colon cancer, lung cancer, and prostate cancer.

In one embodiment, the cancer comprises a KRAS mutation. As demonstrated in Example 17, antibodies of the invention (e.g., Ab #6) are capable of inhibiting the growth of tumor cells that comprise a KRAS mutation, either when used as a single agent (monotherapy) or in combination with another therapeutic agent. In another embodiment, the cancer comprises a PI3K mutation. As demonstrated in Example 19, antibodies of the invention (e.g., Ab #6) are capable of inhibiting the growth of tumor cells that comprise a PI3K mutation, either when used as a single agent (monotherapy) or in combination with another therapeutic agent.

The antibody can be administered alone or with another therapeutic agent which acts in conjunction with or synergistically with the antibody to treat the disease associated with ErbB3 mediated signaling. Such therapeutic agents include, for example, the anticancer agents described infra (e.g., cytotoxins, chemotherapeutic agents, small molecules and radiation). As demonstrated in Examples 16, 17 and 19, antibodies of the invention (e.g., Ab #6) when used in combination with another therapeutic agent can exhibit increased tumor growth inhibition as compared to when used in monotherapy. Preferred therapeutic agents for combination therapy include erlotinib (Tarceva®), paclitaxel (Taxol®) and cisplatin (CDDP).

In another embodiment, the present invention provides a method for diagnosing a disease (e.g., a cancer) associated with ErbB3 upregulation in a subject, by contacting antibodies or antigen binding portions of the invention (e.g., ex vivo or in vivo) with cells from the subject, and measuring the level of binding to ErbB3 on the cells. Abnormally high levels of binding to ErbB3 indicate that the subject has a disease associated with ErbB3 upregulation.

Also within the scope of the present invention are kits comprising antibodies and antigen binding portions thereof of the invention which optionally include instructions for use in treating or diagnosing a disease associated with ErbB3 upregulation and/or ErbB3 dependent signaling. The kits may include a label indicating the intended use of the contents of the kit. The term label includes any writing, marketing materials or recorded material supplied on or with the kit, or which otherwise accompanies the kit.

Other embodiments of the present invention are described in the following Examples.

The present invention is further illustrated by the following examples which should not be construed as further limiting. The contents of Sequence Listing, figures and all references, patents and published patent applications cited throughout this application are expressly incorporated herein by reference.

EXAMPLES

Materials and Methods

Throughout the examples, the following materials and methods were used unless otherwise stated.

In general, the practice of the present invention employs, unless otherwise indicated, conventional techniques of chemistry, molecular biology, recombinant DNA technology, immunology (especially, e.g., antibody technology), and standard techniques in polypeptide preparation. See, e.g., Sambrook, Fritsch and Maniatis, *Molecular Cloning: Cold Spring Harbor Laboratory Press* (1989); *Antibody Engineering Protocols* (Methods in Molecular Biology), 510, Paul, S., Humana Pr (1996); *Antibody Engineering: A Practical Approach* (Practical Approach Series, 169), McCafferty, Ed., Irl Pr (1996); *Antibodies: A Laboratory Manual*, Harlow et al., C.S.H.L. Press, Pub. (1999); and *Current Protocols in Molecular Biology*, eds. Ausubel et al., John Wiley & Sons (1992). In vitro and in vivo model systems for assaying HCV biology are described, for example, in *Cell culture models and animal models of viral hepatitis. Part II: hepatitis C, Lab. Anim.* (NY).; 34(2):39-47 (2005) and in *The chimpanzee model of hepatitis C virus infections, ILAR J.*; 42(2):117-26 (2001).

Cell Lines

All the cell lines used in the experiments described below were obtained from the National Cancer Institute or provided by investigators, as indicated.

Cell Lines:
MCF7—ATCC cat. No. HTB-22
T47D—ATCC cat. No. HTB-133
Colo357—These cells were obtained from an academic investigator and are described by Kolb et al. (2006) Int. J. Cancer, 120:514-523.
Du145—ATCC cat. No. HTB-81
OVCAR8—source already described in provisional application.
H1975 ATCC cat. No. CRL-5908

Pulverization of Tumor Cells

A cryopulverizer (Covaris Inc) was used for the pulverization of tumors. Tumors were stored in special bags (pre-weighed before the addition of the tumor) and placed in liquid nitrogen while handling them. For small tumors, 200 uL of Lysis buffer was first added to the bag containing the tumor, frozen in liquid nitrogen and then pulverized to improve the recovery of the tumor from the bag. Pulverized tumors were transferred to 2 mL Eppendorf tubes and placed in liquid nitrogen until ready for further processing Lysis of Tumor Cells Tumors were lysed in Lysis buffer supplemented with protease and phosphatase inhibitors. Lysis Buffer was added to the tumor aliquots in a final concentration of about 62.5 mg/mL. Tumor samples were homogenized by vortexing for 30 sec and incubating on ice for about 30 min. The lysates were spun for about 10 min in Qiagen Qiashredder columns for further homogenization of the samples. Cleared lysates were aliquoted into fresh tubes for further processing.

BCA Assay

BCA assay (Pierce) was performed following the manufacturer's protocol on all tumor samples. The total protein concentration (in mg/mL) of each tumor sample was later used in the normalization of the ELISA results ELISA Assay All ELISA reagents for the total and phospho-ErbB3 ELISAs were purchased from R&D Systems as Duoset kits. 96-well Nunc Maxisorb plates were coated with 50 uL of an antibody and incubated overnight at room temperature. Next morning, plates were washed 3 times with 1000 µl/well in the BioTek plate washer with PBST (0.05% Tween-20). Plates were subsequently blocked for about an 1 hr at room temperature with 2% BSA in PBS. The plates were washed 3 times with 1000 µl/well in the BioTek plate washer with PBST (0.05% Tween-20). 50 µL of cell lysates and standards diluted in 50% Lysis buffer and 1% BSA were used in duplicates for further processing. Samples were incubated for 2 hrs at 4° C. on a plate shaker and washed 3 times with 1000 µl/well in the BioTek plate washer with PBST (0.05% Tween-20). About 50 µl of a detection antibody diluted in 2% BSA, PBST was added and incubated for about 1 hr at room temperature. For phosphor-ErbB3, the detection antibody was directly conjugated to horse radish peroxidase (HRP) and incubated for 2 hrs at room temperature. The plate was washed 3 times with 1000 µl/well in the BioTek plate washer with PBST (0.05% Tween-20). About 50 µl of Streptavidin-HRP was added and incubate for 30 min at room temperature (except for pErbB3). The plates were washed 3 times with 1000 µl/well in the BioTek plate washer with PBST (0.05% Tween-20). About 50 µL of Supersignal Pico ELISA substrate was added and the plate was read using a Fusion plate reader. The data was analysed using EXCEL. Duplicate samples were averaged and the error bars were used to represent the standard deviation between the two replicates.

Example 1

Production of Antibodies Using Phage Display

In order to obtain human anti-ErbB3 antibodies referred to herein as Ab #6, Ab #3, Ab #14, Ab #17, and Ab #19, a human Fab-phage library including a unique combination of immunoglobulin sequences obtained from human donors (Hoet et al. supra, incorporated by reference in its entirety herein) was initially screened for ErbB3 binders.

Using purified ErbB3 and a Chinese hamster ovary cell line expressing cell surface ErbB3, 73 unique Fab sequences from the library were identified. These 73 clones were then reformatted as Fab only without the phage. Using high throughput methods, these Fabs were expressed on a small scale and tested for binding using ELISA and the Flexchip method which is a high-throughput surface plasmon resonance (SPR) technology. The 73 Fabs without the phage were spotted on a chip surface and the binding kinetics and epitope blocking to a ErbB3-his fusion target protein or a ErbB3-Fcprotein (R & D Systems) were measured. The equilibrium binding constant and on/off rates for the Fabs were calculated from the data obtained.

Figure 1B:
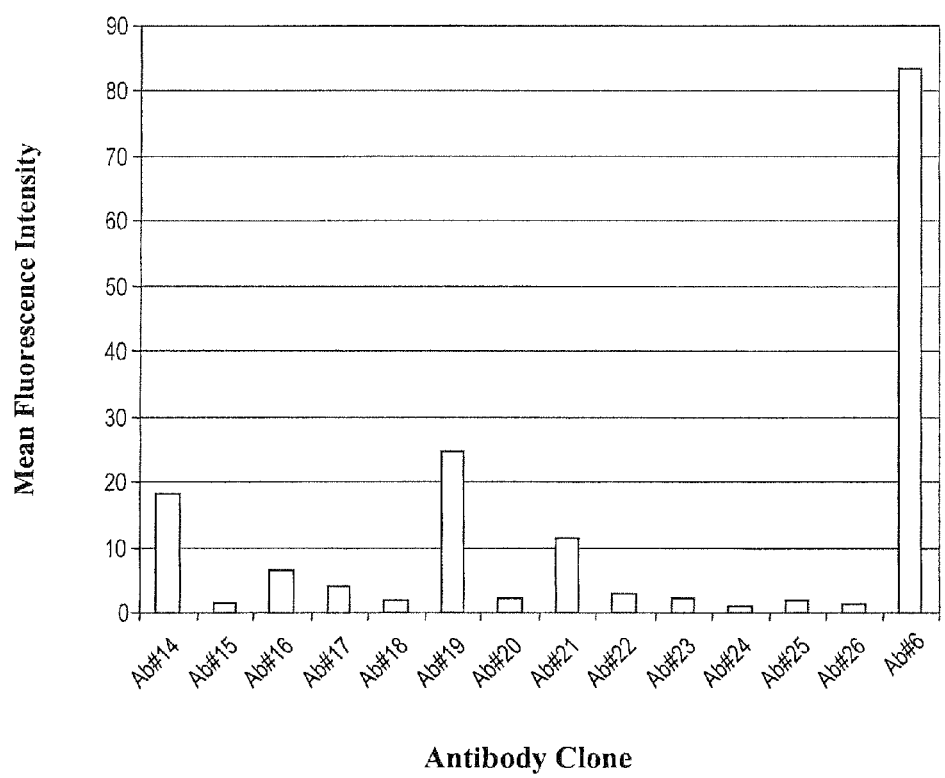

Binding of the various Fabs to MALME-3M cells was next examined using about 500 nM of the Fabs and a 1:750 dilution of a goat anti-human Alexa 647 secondary antibody. As shown in FIGS. 1A and 1B, several candidate Fabs exhibited appreciable staining of MALME-3M cells.

Example 2

Optimization of Anti-ErbB3 Fabs

Subsequent to the identification of Fabs which blocked the binding of ErbB3 ligand, heregulin, to ErbB3, the VH and VL sequences of the Fabs were codon-optimized as follows.

Specifically, the VH and VL regions were reformatted using expression constructs for expression as an IgG1 or IgG2 isotype. The constructs included a Selexis backbone which has a cassette designed for substitution of the appropriate heavy and light chain sequences. The Selexis vectors included a CMV promoter and a matching poly-A signal.

The nucleic acid sequences for the codon-optimized VH and VL of Ab #6 are set forth in SEQ ID NOs:25 and 26, respectively, and those for Ab #3 are set forth in SEQ ID NOs:27 and 28, respectively, as shown in FIG. 22.

Example 3

Binding Affinity for ErbB3

The dissociation constants of the anti-ErbB3 antibodies were measured using two independent techniques, i.e., a Surface Plasmon Resonance Assay and a cell binding assay using MALME-3M cells.

Surface Plasmon Resonance Assay

The Surface Plasmon Resonance Assay (also referred to as the Flexchip assay) was performed as described in Wassaf et al. (2006) *Analytical Biochem.*, 351:241-253. The $K_D$ value was calculated based on the formula $K_D=K_d/K_a$.

Figure 2A:
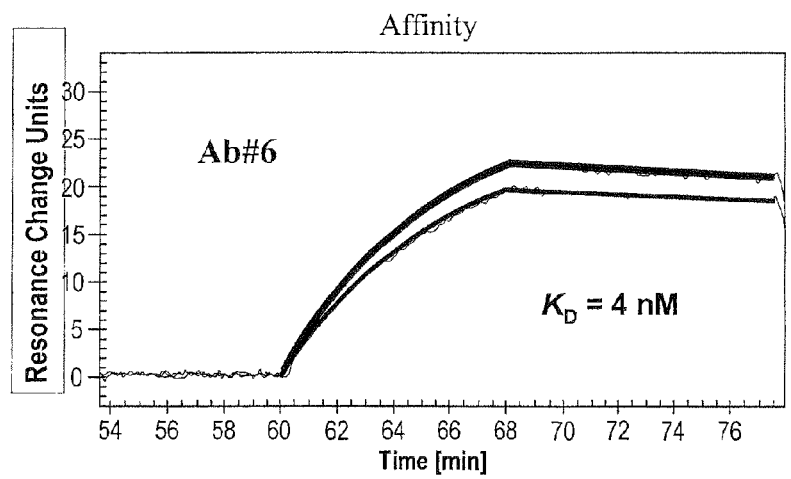
FIGS. 2A-2D are graphs depicting the $K_D$ values of various anti-ErbB3 antibody candidates.
Figure 2B:
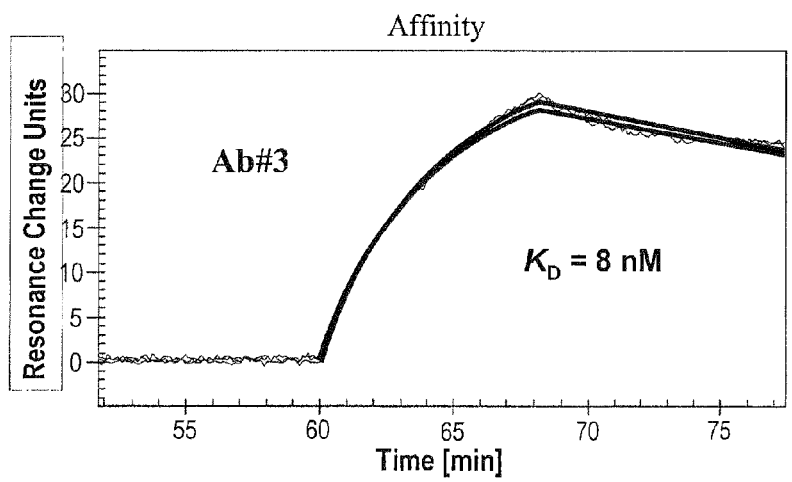

The $K_D$ values of Ab #6 and Ab #3, respectively, as measured using the Surface Plasmon Resonance Assay, are depicted in FIGS. 2A and 2B. Ab #6 had a $K_D$ value of about 4 nM and Ab #3 had a $K_D$ value of about 8 nM, as depicted in FIGS. 2A and 2B, respectively.

In additional experiments to study the binding kinetics of Ab #6, a Kinetic Exclusion Assay (KinExA) was used to determine the association and dissociation rates for the antibody. An association rate of $1.43\times10^5$ $M^{-1}$ $s^{-2}$ and a dissociation rate of $1.10\times10^{-4}$ $s^{-1}$ was measured by KinExA, with the dissociation constant ($K_d$) determined to be 769 pM. Furthermore, surface plasmon resonance demonstrated that Ab #6 competes with HRG-1-beta for binding to ErbB3.

Cell Binding Assay

The cell binding assay for determining the $K_D$ values of Ab #6 and Ab #3 was performed as follows.

MALME-3M cells were detached with 2 mls trypsin-EDTA+2 mls RMPI+5 mM EDTA at room temperature for 5 minutes. Complete RPMI (10 mls) was added immediately to the trypsinized cells, resuspended gently and spun down in a Beckman tabletop centrifuge at 1100 rpm for 5 minutes. Cells were resuspended in BD stain buffer (PBS+2% fetal bovine serum+0.1% sodium azide, Becton Dickinson) at a concentration of $2\times10^6$ cells per ml and 50 µl ($1\times10^5$ cells) aliquots were plated in a 96-well titer plate.

A 150 µl solution of 200 nM anti-ErbB3 antibody (Ab #6 or Ab #3) in BD stain buffer was prepared in an eppendorf tube and serially diluted 2-fold into 75 µl BD stain buffer. The concentrations of the diluted antibody ranged from 200 nM to 0.4 nM. 50 µl aliquots of the different protein dilutions were then added directly to the 50 ul cell suspension giving the final concentrations of 100 nM, 50 nM, 25 nM, 12 nM, 6 nM, 3 nM, 1.5 nM, 0.8 nM, 0.4 nM and 0.2 nM of the antibody.

Aliquoted cells in the 96-well plate were incubated with the protein dilutions for 30 minutes at room temperature on a platform shaker and washed 3 times with 300 µl BD stain buffer. Cells were then incubated with 100 µl of a 1:750 dilution of Alexa 647-labeled goat anti-human IgG in BD stain buffer for 45 minutes on a platform shaker in the cold room. Finally, cells were washed twice, pelleted and resuspended in 250 µl BD stain buffer+0.5 µg/ml propidium iodide. Analysis of 10,000 cells was done in a FACScalibur flow cytometer using the FL4 channel. MFI values and the corresponding concentrations of the anti-ErbB3-antibodies were plotted on the y-axis and x-axis, respectively. The $K_D$ of the molecule was determined by GraphPad Prism using the one-site binding model for a non-linear regression curve.

Figure 2C:
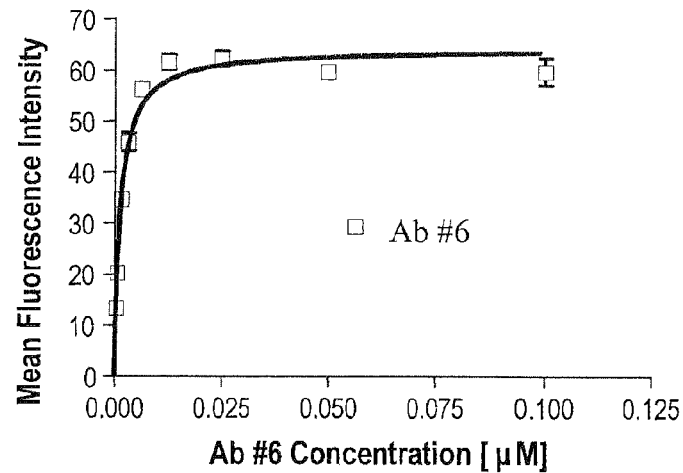
Figure 2D:
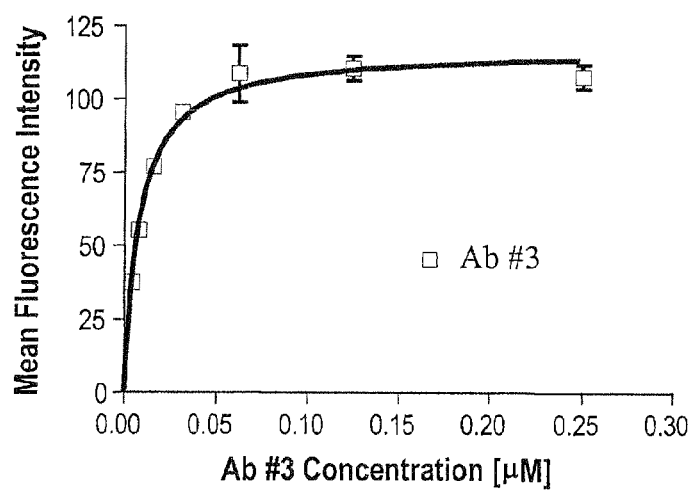

The $K_D$ value was calculated based on the formula $Y=Bmax*X/K_D+X$ (Bmax=fluorescence at saturation. X=antibody concentration. Y=degree of binding). As shown in FIGS. 2C and 2D, Ab #6 and Ab #3 had $K_D$ values of about 4 nM and 1.3 nM, respectively, in a cell binding assay using MALME-3M cells.

Example 4

Binding Specificity/Epitope Binding for ErbB3

The binding specificity of an IgG2 isotype of Ab #6 to ErbB3 was assayed using ELISA as follows. Identification of the epitope bound by Ab #6 was also analyzed.

Specifically, 96-well Nunc Maxisorb plates were coated with 50 µl of 5 µg/ml protein (recombinant human ErbB3, recombinant human EGFR or unrelated protein (BSA)) and incubated overnight at room temperature. The next morning, plates were washed 3 times with 1000 µl/well of PBST (0.05% Tween-20) in the BioTek plate washer. The wells were blocked for 1 hr at room temperature with 2% BSA in PBS. The plates were washed 3 times with 1000 µl/well of PBST (0.05% Tween-20) in the BioTek plate washer. About 50 µL of the Ab #6 was added at several dilutions (1 µM and serial 2 fold dilutions) in 2% BSA, PBST. All samples were run in duplicate and incubated for 2 hrs at 4° C. on a plate shaker. The plates were washed plates 3 times with 1000 µl/well of PBST (0.05% Tween-20) in the BioTek plate washer. 50 µl of human IgG detection antibody (HRP conjugated (Bethyl Inc; 1:75000 dilution in 2% BSA, PBST)) was added and the plates were incubated for 1 hr at room temperature. The plates were washed plate 3 times with 1000 µl/well of PBST (0.05% Tween-20) in the BioTek plate washer. 50 µL of Supersignal Pico ELISA substrate was added and the plate was read on the Fusion plate reader. The data was analyzed using the EXCEL program. Duplicate samples were averaged and the error bars represent the standard deviation between the two replicates.

Figure 3:
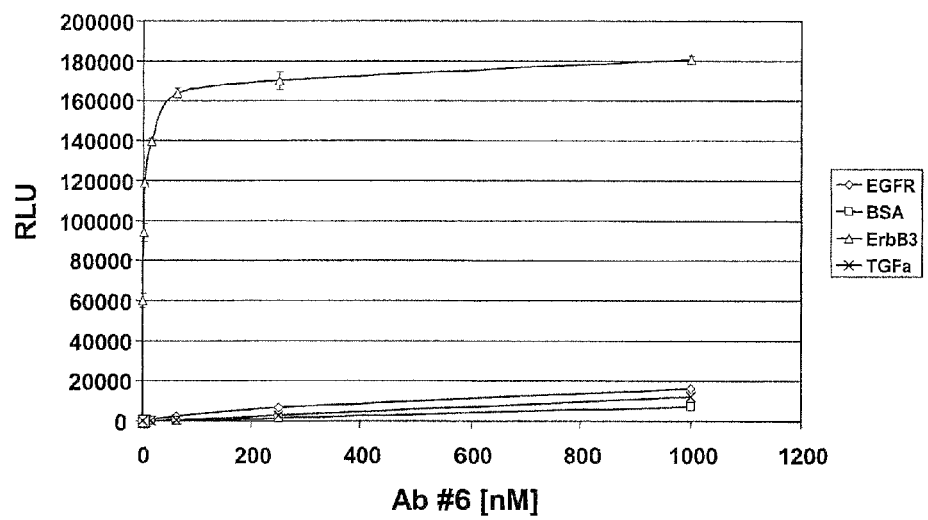
FIG. 3 is a graph depicting the binding specificity of an anti-ErbB3 antibody (Ab #6) to ErbB3 using ELISA. EGFR, BSA and TGF-α were used as controls.

As shown in FIG. 3, Ab #6 bound recombinant ErbB3 in an ELISA, but did not show any appreciable binding to EGFR, BSA or TGF-α.

A fragment (truncation mutant) corresponding to amino acid residues 20-202 of ErbB3 was cloned into the yeast display vector pYD2 (a modified version of pYD1 (Invitrogen) with a stop codon engineered in front of the His tag) between the Nhe and BsiWI restriction sites. The plasmid was transformed into the yeast strain EBY100 (Invitrogen) and clones containing the plasmid selected on Trp-selective medium. The clone was grown in glucose containing medium overnight at 30° C. and expression of the ErbB3 truncation mutant was induced by transfer to a galactose-containing medium for 2 days at 18° C. Yeast displaying the ErbB3 truncation mutant were stained with 50 nM of Ab #6, followed by a goat anti-human antibody labeled with Alexa dye-647. A separate sample was stained with the goat anti-human antibody only to show that there is no non-specific binding to yeast of the secondary antibody. Analysis was performed by flow cytometry on the FACS Calibur cell sorter (BD Biosciences).

Figure 30:
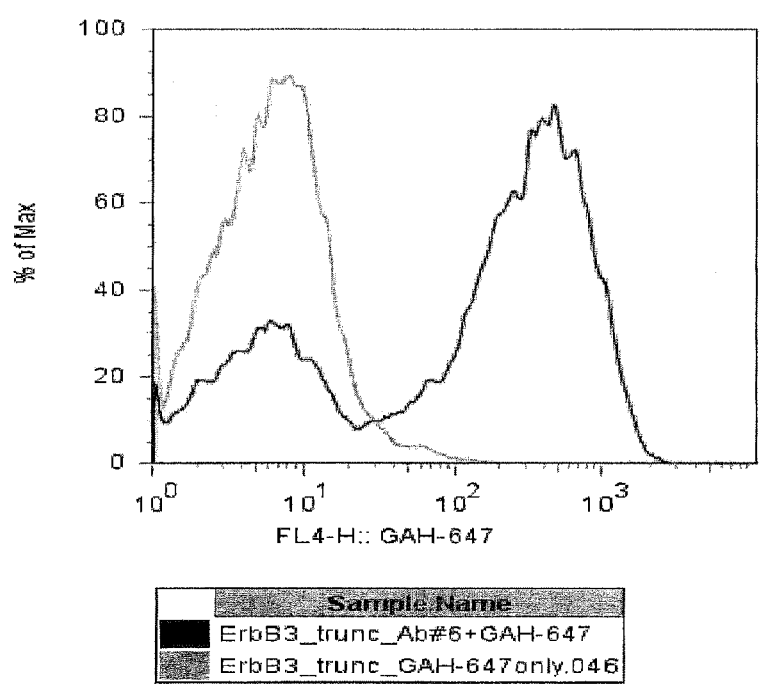
FIG. 30 is a graph showing Ab #6 binds amino acid residues 20-202 of ErbB3.

As shown in FIG. 30, Ab #6 bound to the truncation mutant, i.e., amino acid residues 20-202 of ErbB3.

Example 5

Downregulation of Total ErbB3 on Tumor Cells

The ability of Ab #6 to downregulate ErbB3 expression both in vitro and in vivo in tumor cells was tested as follows.

MALME-3M cells were seeded in 96 well tissue culture plates and grown in RPMI-1640 media supplemented with antibiotics, 2 mM L-glutamine and 10% fetal bovine serum (FBS) for 24 hours at 37° C. and 5% carbon dioxide. Media was then switched to RPMI-1640 MEDIA with antibiotics, 2 mM L-glutamine with and without the antibody at concentrations of 1 uM, 250 nM, 63 nM, 16 nM, 4.0 nM, 1.0 nM, 240 pM, 61 pM and 15 pM. Cells were grown for 24 hours at 37° C. and 5% carbon dioxide, washed with cold PBS, then harvested with mammalian protein extract (MPER) lysis (Pierce, 78505) buffer containing 150 mM NaCl, 5 mM sodium pyrophosphate, 10 uM bpV (phen), 50 uM phenalarsine, 1 mM sodium orthovanadate, and protease inhibitor cocktail (Sigma, P714). Cell lysates were diluted two-fold with 4% bovine serum albumin in phosphate buffered saline with 0.1% tween-20, then analyzed by ELISA with mouse anti-human ErbB3 capture antibody and biotinylated mouse anti-human ErbB3 secondary detection antibody. Signal was generated with streptavidin conjugated to horseradish-peroxidase reacted with chemiluminescent substrate (Pierce, 37070). ELISAS were visualized using a luminometer.

Figure 4:
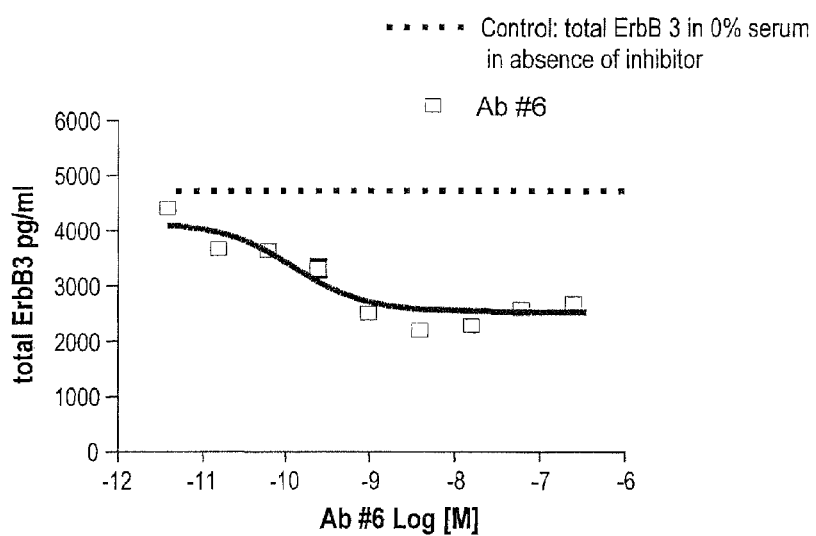
FIG. 4 is a graph depicting the ability of an anti-ErbB3 antibody (Ab #6) to decrease total ErbB3 levels in MALME-3M melanoma cells in vitro, as measured using ELISA.

As shown in FIG. 4, Ab #6 decreased total ErbB3 levels by about 46.9% in MALME-3M cells in vitro, as measured by ELISA. Media containing no serum and antibody was used as control.

In a further experiment, the downregulation of ErbB3 receptors on MALME-3M cells using IgG1 and IgG2 isotypes of Ab #6 was examined using FACS analysis. MALME-3M cells were trypsinized from a 15 cm dish and washed once with RPMI+10% fetal bovine serum. Cell pellets were resuspended at a density of $1 \times 10^6$ cells per ml. Two aliquots of $2 \times 10^5$ cells were added to a 12-well tissue culture plate and resuspended in a final volume of 800 ul RPMI+10% fetal bovine serum. To one well, Ab #6 IgG1 or Ab #6IgG2 isotype was added to a final concentration of 100 nM (treated sample) and to the other well, an equivalent volume of PBS was (untreated sample) was added.

The following day, treated and untreated cells were trypsinized, washed and incubated with 100 nM of Ab #6 in BD stain buffer for 30 minutes on ice. Cells were washed twice with 1 ml BD stain buffer and incubated with 100 ul of a 1:500 dilution of Alexa 647-labeled goat anti-human Alexa 647 for 45 minutes on ice. Cells were then washed and resuspended in 300 ul BD stain buffer+0.5 ug/ml propidium iodide. Analysis of 10,000 cells was done in a FACScalibur flow cytometer using the FL4 channel.

As shown in FIGS. 5A and 5B, both IgG1 and IgG2 isotypes of Ab #6 downregulated ErbB3 on MALME-3M cells by about 62% and about 66%, respectively.

In order to determine whether this decrease was due to internalization of the ErbB3 receptor on the surface of MALME-3M cells, the expression of ErbB3 in the presence of the antibody over time was measured. Specifically, MALME-3M cells were trypsinized from a 15 cm dish and washed once with RPMI+10% fetal bovine serum. Cell pellets were resuspended at a density of $1 \times 10^6$ cells per ml. Two aliquots of $2 \times 10^5$ cells were added to a 12-well tissue culture plate and resuspended in a final volume of 800 µl RPMI+10% fetal bovine serum. To one well, the anti-ErbB3 antibody was added to a final concentration of 100 nM (treated sample) and to the other well, an equivalent volume of PBS was (untreated sample) was added. The following day, treated and untreated cells were trypsinized, washed and incubated with 100 nM anti-ErbB3 antibody in BD stain buffer for 30 minutes on ice. Cells were washed twice with 1 ml BD stain buffer and incubated with 100 µl of a 1:500 dilution of Alexa 647-labeled goat anti-human Alexa 647 for 45 minutes on ice. Cells were then washed and resuspended in 300 µl BD stain buffer+0.5 µg/ml propidium iodide. Analysis of 10,000 cells was done in a FACScalibur flow cytometer using the FL4 channel.

As shown in FIG. 6, downregulation of ErbB3 in the presence of Ab #6 was measured at 0 hour (FIG. 6A), 0.5 hour (FIG. 6B), 2 hour (FIG. 6C) and 24 hours (FIG. 6D). As shown in FIG. 6A-6D, about 50% of the cell surface ErbB3 receptors were downregulated after about 30 minutes and at about 24 hours, about 93% of the cell surface receptors were downregulation.

The ability of Ab #6 to cause ErbB3 downregulation in vivo in melanoma cells was also examined as follows.

Briefly, T-cell deficient nu/nu mice (3-4 week old female mice originated at NIH; outbred; albino background) were purchased from Charles River Labs (Wilmington, Mass.). MALME-3M cells for implantation were grown in culture (RPMI media, 10% FBS, L-glutamine and antibiotics, 37° C., 5% CO2) to about 80% confluency before harvesting. Cells were kept on ice until implantation. Mice were implanted via subcutaneous injection with 100 ul MALME-3M cells on the right flank and allowed to recover while being monitored for initial tumor growth.

The tumors were measured (length by width) by digital caliper and the mice were dosed with IgG2a (Sigma, M7769-5MG) by intravenous injection. Mice were dosed intra-peritoneally every other day with either 15 µg or 100 µg of antibody number 6 and tumors were measured three times per week and recorded in a Microsoft EXCEL spreadsheet.

Final tumor measurements (L×W) were taken, the mice were euthanized by $CO_2$ asphyxiation and tumors were excised, snap frozen in liquid nitrogen, and were stored at −80° C. (for biochemical analysis). Final tumor measurements were analyzed and graphed by tumor area and tumor volume as described, for example, in Burtrum at al., (2003) *Cancer Res.*, 63:8912-8921. The data was also analyzed by "normalized' and "non-normalized" means for both tumor volume and tumor area. For the "normalization" of the data, at each time point of measurement, each tumor in each group was divided by the initial tumor size determined by caliper measurement.

Figure 7:
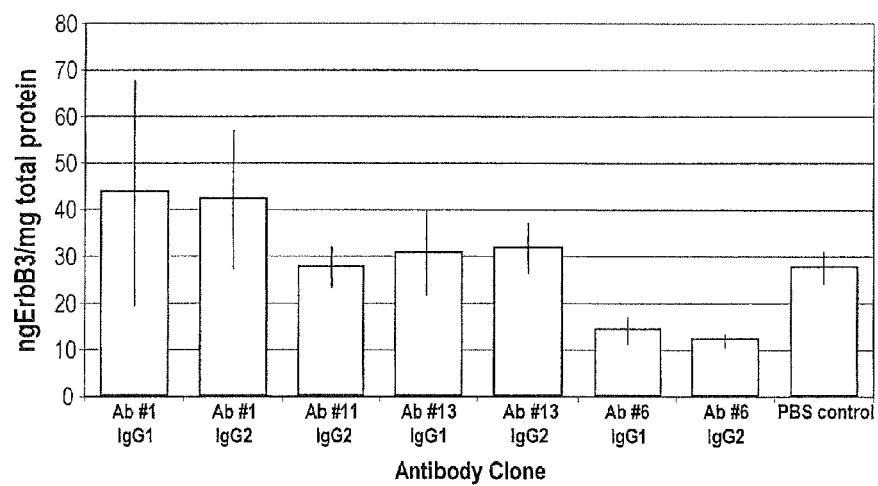
FIG. 7 is a bar graph depicting the ability of various anti-ErbB3 antibodies to downregulate ErbB3 in melanoma cells in vivo.

As shown in FIG. 7, among the various antibodies tested in this assay, Ab #6 caused downregulation of total ErbB3 as soon as 24 hours post-injection in tumors treated with either IgG1 or IgG2 isotype of Ab #6). PBS was used as a control In a further experiment, the ability of Ab #6 to downregulate ErbB3 in ADRr xenografts in vivo was examined.

Briefly, the samples were pulverized in a cryopulverizer (Covaris Inc). Tumors were stored in special bags (preweighed before the addition of the tumor) and placed in liquid nitrogen while handling them. For small tumors, 200 µL of Lysis buffer was first added to the bag with the tumor, frozen in liquid nitrogen and then pulverized to improve the recovery of the tumor from the bag. Pulverized tumors were transferred to 2 ml Eppendorf tubes and placed in liquid nitrogen until lysed. Tumors were lysed in Lysis buffer supplemented with protease and phosphotase inhibitors. Lysis Buffer was added to the tumor aliquots in a final concentration of 62.5 mg/ml. Tumor samples were homogenized by vortexing for 30 seconds and letting them sit on ice for 30 min. The lysates were spun for 10 minutes in Qiagen Qiashredder columns for further homogenization of the samples. Cleared lysates were aliquoted into fresh tubes.

The BCA assay was performed as set forth in the materials and methods section supra.

The total levels of ErbB3 were determined by ELISA. The ELISA reagents were purchased from R&D Systems as Duoset kits. 96-well Nunc Maxisorb plates were coated with 50 µl of respective capture antibody and incubated overnight at room temperature. The next morning, the plates were washed 3 times with 1000 µl/well in a BioTek plate washer with PBST (0.05% Tween-20) and then blocked for 1 hour at room temperature with 2% BSA in PBS. The plates were then washed three times with 1000 µl/well in the BioTek plate washer with PBST (0.05% Tween-20). Lysates (50 µl) and standards were diluted in 50% Lysis buffer and 1% BSA; all samples were run in duplicate. Plates were incubated for 2 hours at 4° C. on a plate shaker and then washed three times with 1000 µl/well in a BioTek plate washer with PBST (0.05% Tween-20). Fifty microliters of detection antibody diluted in 2% BSA, PBST was added and the plates were incubated for 1 hour at room temperature. Plates were washed three times with 1000 µl/well in the BioTek plate washer with PBST (0.05% Tween-20). Fifty microliters of Streptavidin-HRP was added and the plates were incubated for 30 minutes at room temperature. Plates were washed again three times with 1000 µl/well in a BioTek plate washer with PBST (0.05% Tween-20). Fifty microliters of Supersignal Pico ELISA substrate was added and readout was performed on a Fusion plate reader. Data was analyzed using EXCEL. Duplicate samples were averaged and the error bars represent the standard deviation between the two replicates.

Figure 8:
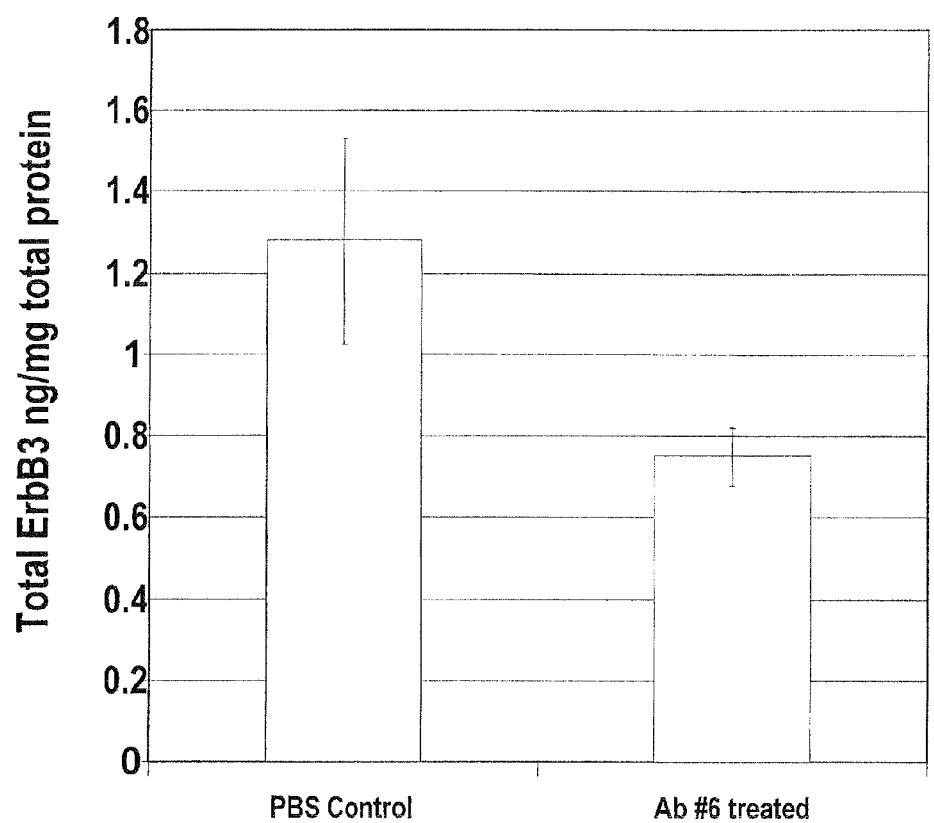
FIG. 8 is a bar graph depicting the ability of an anti-ErbB3 antibody (Ab #6) to downregulate ErbB3 in ADRr xenografts in vivo.

The results of this experiment are shown in FIG. 8. As shown in FIG. 8, Ab #6 downregulated ErbB3 in ADRr xenografts in vivo.

Example 6

Inhibition of Tumor Cell Proliferation

The ability of Ab #6 to inhibit cellular proliferation of cells expressing ErbB3 (e.g., cancer cells) was examined as follows.

MALME3M, ACHN and NCI/ADRr cells were seeded in 96 well tissue culture plates and grown in RPMI-1640 media supplemented with antibiotics, 2 mM L-glutamine and 10% fetal bovine serum (FBS) for 24 hours at 37 degrees Celsius and 5% carbon dioxide. Media was then switched to RPMI-1640 media with antibiotics, 2 mM L-glutamine and with and without the antibody at 1 uM, 250 nM, 63 nM, 16 nM, 4.0 nM, 1.0 nM, 240 pM, 61 pM and 15 pM concentrations. Cells were grown for 96 hours at 37° C. and 5% carbon dioxide, then harvested with CellTiter-Glo® Luminescent Cell Viability Assay (Promega, G7573) and analyzed on a luminometer. Media containing no serum and antibody was used as control.

Figure 9:
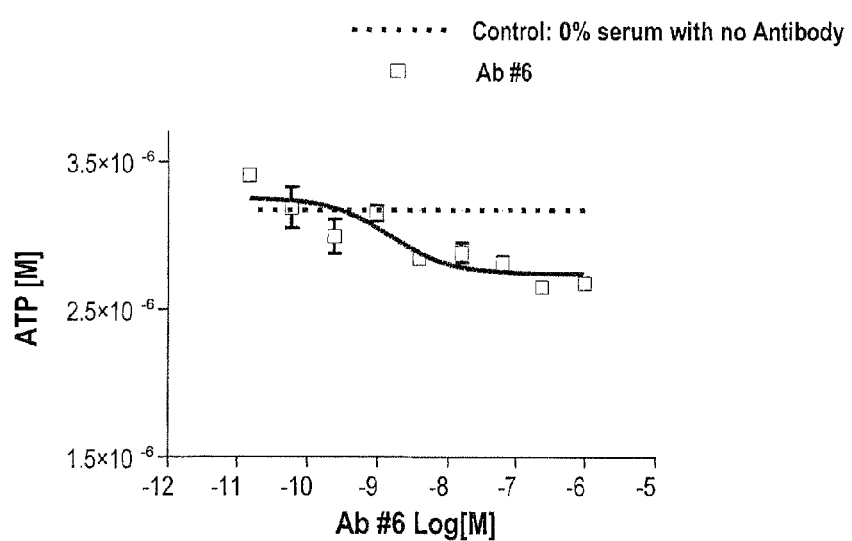
FIG. 9 is a graph depicting the ability of an anti-ErbB3 antibody (Ab #6) to inhibit proliferation of MALME-3M cells in a Cell Titer Glow Assay.
Figure 10:
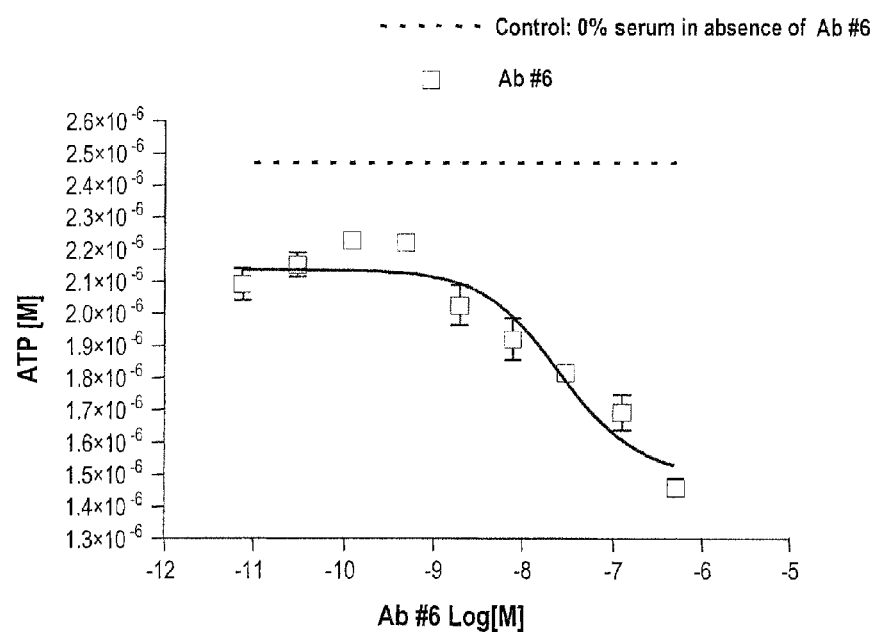
FIG. 10 is a graph depicting the ability of an anti-ErbB3 antibody (Ab #6) to inhibit cell proliferation in an ovarian cell line, ADRr.
Figure 11:
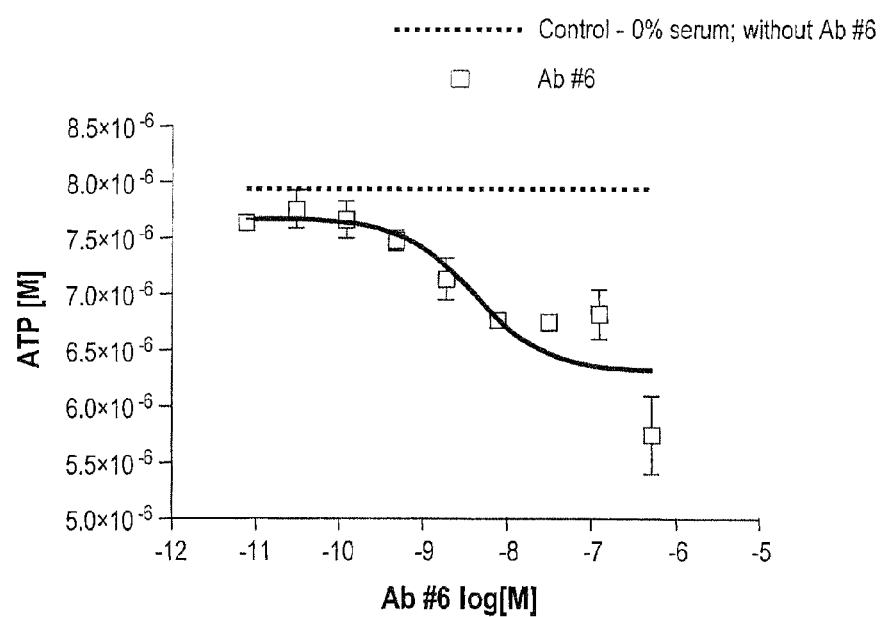
FIG. 11 is a graph depicting the ability of an anti-ErbB3 antibody (Ab #6) to inhibit proliferation of ACHN cells.

As shown in FIGS. 9, 10 and 11, Ab #6 inhibited proliferation of MALME-3M cells (FIG. 9), ADRr ovarian cancer cells (FIG. 10) and ACHN cells (FIG. 11) which express ErbB3. Specifically, Ab #6 inhibited proliferation of MALME-3M cells by about 19.6%, as measured using the Cell Titer Glow assay, and inhibited proliferation of ADRr ovarian cancer cells by about 30.5%. Also, as shown in FIG. 11, Ab #6 inhibited proliferation of ACHN cells by about 25.4%.

Example 7

Inhibition of ErbB3 Phosphorylation in Tumor Cells

The ability of Ab #6 to inhibit ErbB3 phosphorylation in vivo was examined as follows.

The samples were pulverized using the technique described in Example 5 supra, with respect to FIG. 8. The BCA assay was performed as set forth in the Materials and Methods section supra, and the ELISA assay was performed as described in Example 5 supra with respect to FIG. 8.

Figure 12:
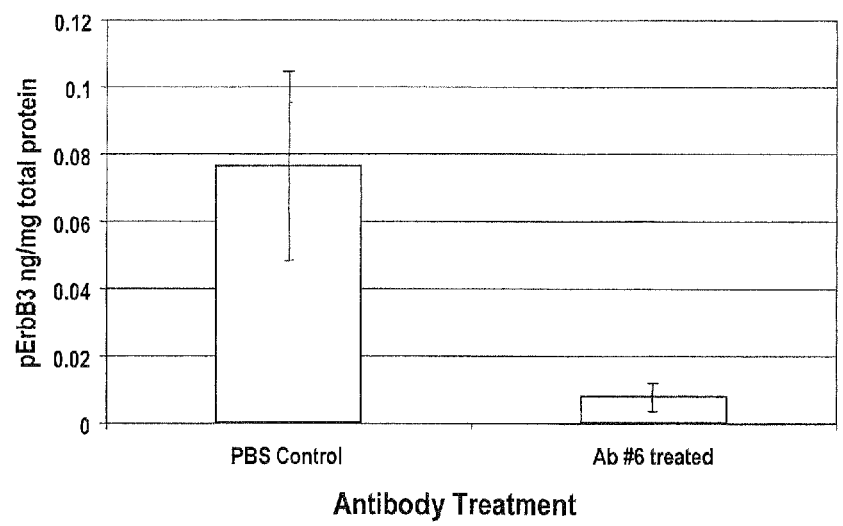
FIG. 12 is a bar graph depicting the ability of an anti-ErbB3 antibody (Ab #6) to inhibit ErbB3 phosphorylation in ADRr xenografts in vivo.

The results of this experiment are shown in FIG. 12. As shown in FIG. 12, Ab #6 significantly inhibited ErbB3 phosphorylation in ADRr ovarian xenografts in vivo, as measured by the amount of phosphorylated ErbB3 (pErbB3) in ng/mg of total protein.

The ability of Ab #6 to inhibit betacellulin (BTC) or heregulin (HRG) induced ErbB3 phosphorylation was also examined, as follows.

Ovarian ADRr cells were preincubated with Ab #6 for 30 minutes prior to stimulation with 50 mM BTC, 10 mM HRG or 333 nM TGF-α. Following pre incubation, the media was removed and the cells were stimulated for 5 minutes at 37° C., 5% CO2 with 50 nM BTC or 333 nM TGF-α (for PE498). HRG controls (5 minutes, 5 nM), 10% serum and 0% serum controls were also used. Cells were washed with 1× cold PBS and lysed in 300 cold lysis buffer (M-PER buffer plus sodium vanadate (NaVO4, Sigma), 2-glycerophosphate, phenylarsine oxide, BpV and protease inhibitors) by incubating on ice for 30 minutes. Lysates were stored overnight at −80° C.

Figure 13A:
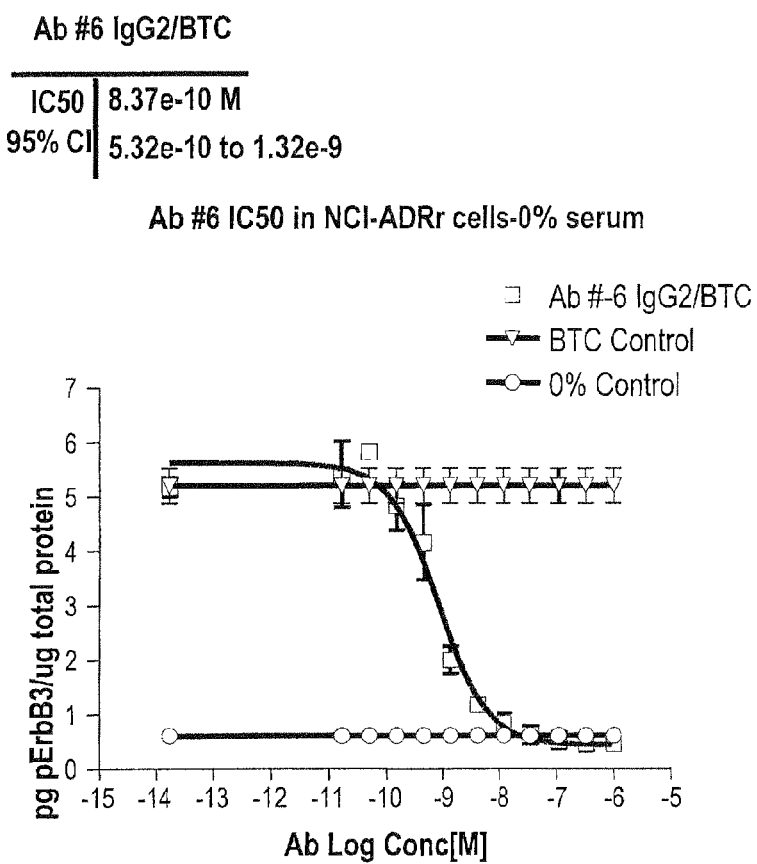
FIGS. 13A-13C are graphs depicting the ability of an anti-ErbB3 antibody (Ab #6) to inhibit betacellulin and heregulin-mediated phosphorylation of ErbB3 in ADRr cells.
Figure 13B:
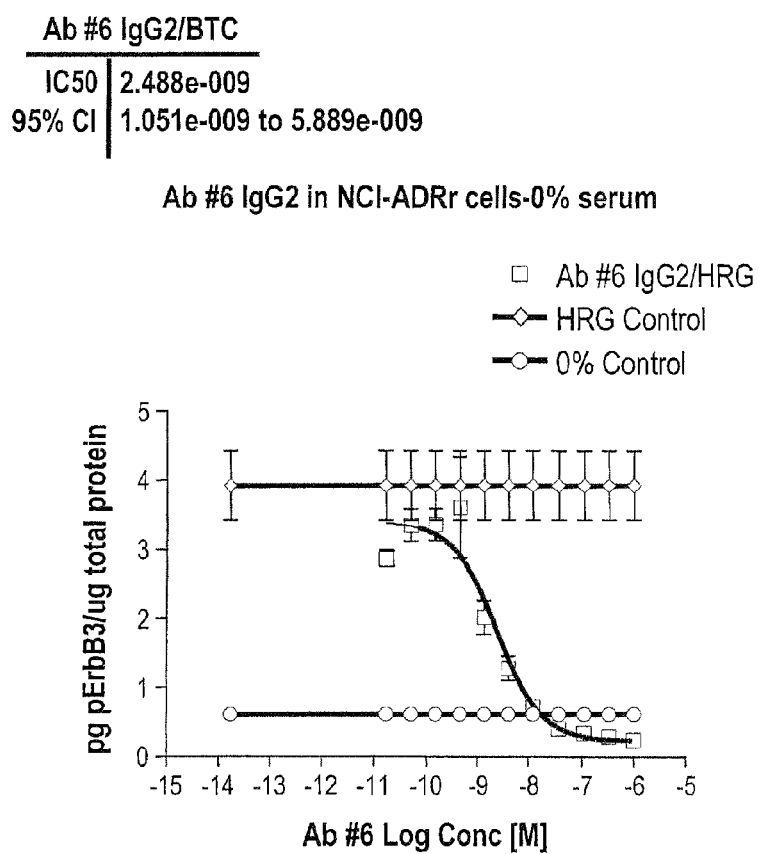
Figure 13C:
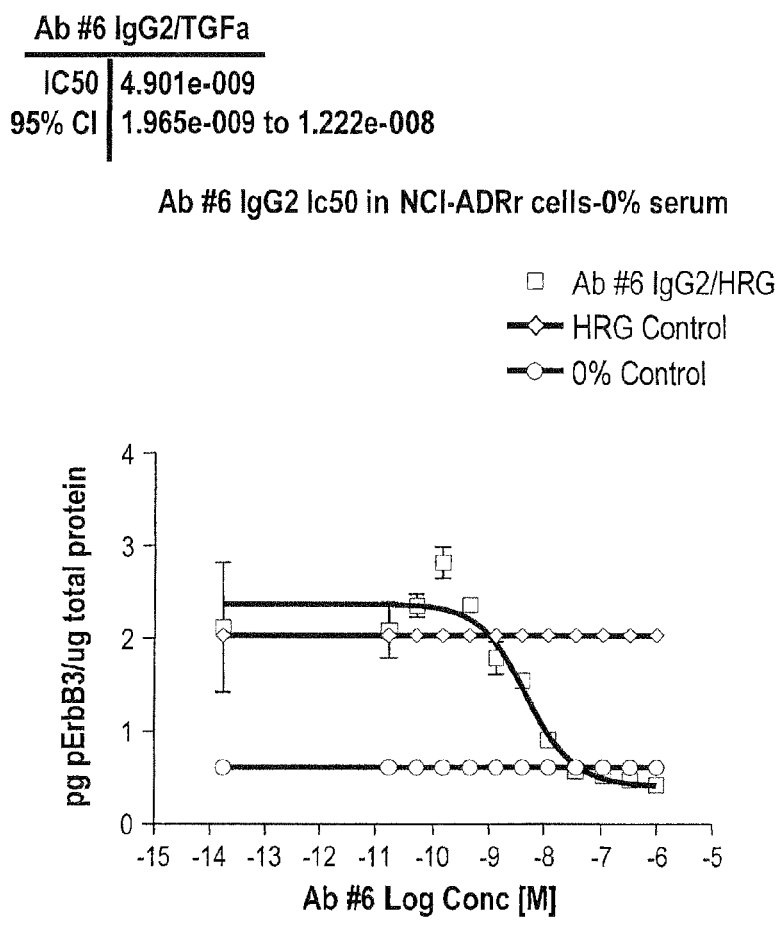

As shown in FIGS. 13A-13C, Ab #6 significantly inhibited both betacellulin and heregulin-mediated phosphorylation of ErbB3.

In a further experiment, the ability of Ab #6 to inhibit ErbB3 phosphorylation in ovarian tumor cell lines OVCAR 5 and OVCAR 8 was examined as follows.

The OVCAR 5 and OVCAR 8 cell lines were obtained from the National Cancer Institute, Division of Cancer Treatment and Diagnostics ("DCTD"). The ELISA was performed as described in the Materials and Methods section supra.

Figure 14A:
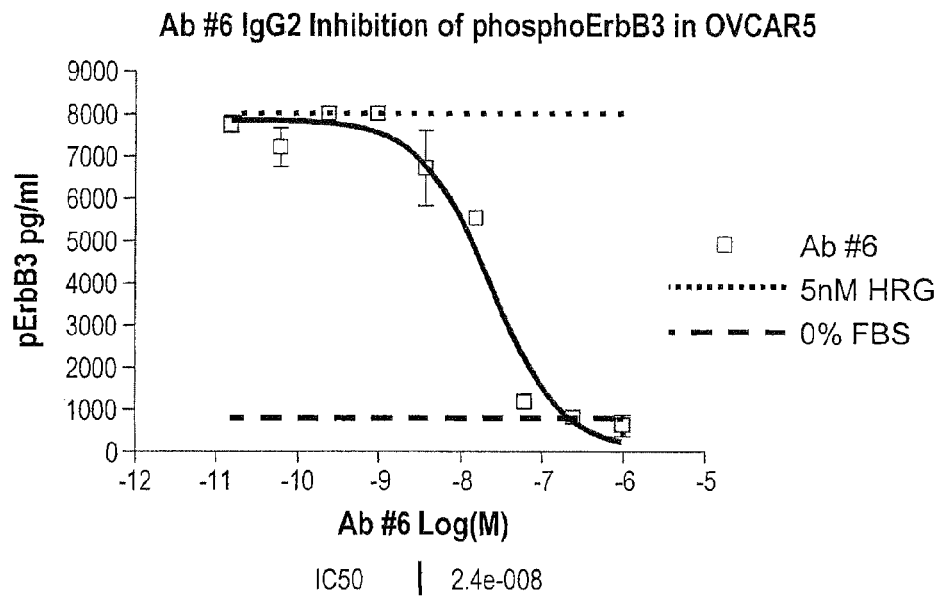
FIGS. 14A-14B are graphs depicting the ability of an anti-ErbB3 antibody (Ab #6 IgG2 isotype) to inhibit ErbB3 phosphorylation in ovarian tumor cell lines OVCAR 5 and OVCAR 8.
Figure 14B:
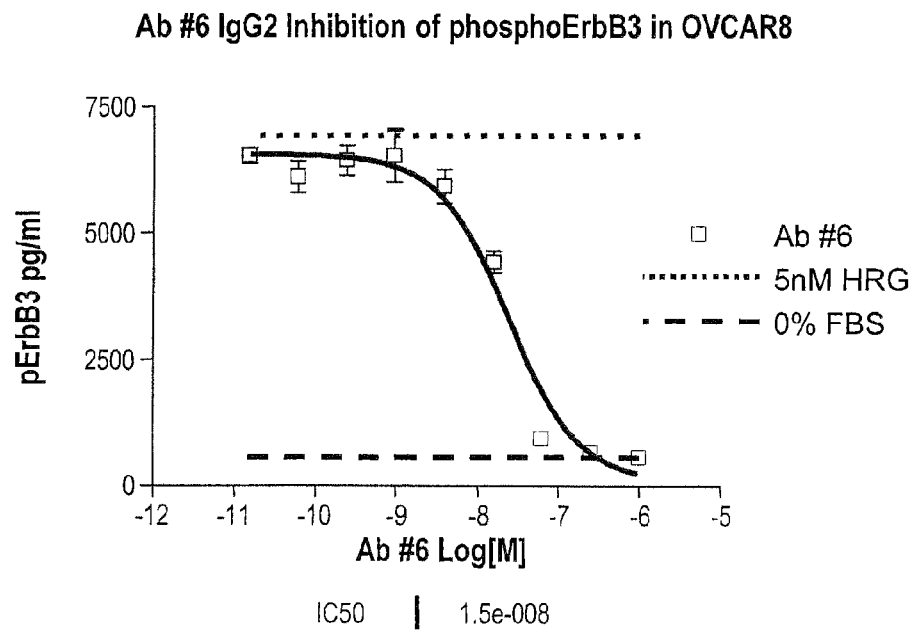

The results of this experiment are depicted in FIGS. 14A and 14B. As depicted in FIGS. 14A and 14B, Ab #6 inhibited ErbB3 phosphorylation in both OVCAR 5 and OVCAR 8 ovarian cancer cell lines.

As discussed above, Ab #6 inhibits betacellulin-mediated phosphorylation of ErbB3. In order to investigate whether betacellulin-mediated phosphorylation of ErbB3 occurs through ErbB1 or ErbB3, the following experiment was performed.

ADRr cells or MALME-3M cells ($1 \times 10^5$) were pre-incubated with 25 µM of anti-ErbB3 Ab #6 or 25 µM of Erbitux (as control) in 50 µl BD stain buffer for 30 minutes on ice. After 30 minutes, 50 µl of 400 nM biotinylated BTC was added to the cells and incubated for another 30 minutes on ice. This gave a final concentration of 12.5 µM antibodies and 200 nM BTC. Cells were then washed twice with 500 µl BD stain buffer and incubated with 100 µl of a 1:200 dilution of streptavidin-PE (PE=phycoerythrin) (Invitrogen) in BD stain buffer for 45 minutes. Finally, cells were washed twice, resuspended in 300 µl of BD stain buffer and analyzed in a FACScalibur flow cytometer. As a positive control, $1 \times 10^5$ ADRr or MALME-3M cells were incubated with 200 nM BTC for 30 minutes on ice, washed twice and incubated with a 1:200 dilution of streptavidin-PE for 45 minutes. To assess background staining from the streptavidin-PE conjugate, cells were incubated with 100 µl of a 1:200 dilution of streptavidin-PE only for 45 minutes.

Figure 15A:
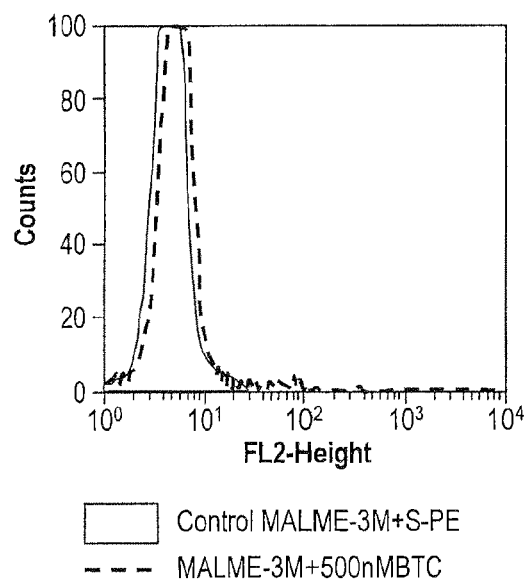
FIGS. 15A-15C are graphs depicting the ability of betacellulin (BTC) to bind ErbB1 as shown by a lack of binding to ErbB1 negative MALME-3M cells (FIG. 17A); binding to ErbB1 positive ADRr cells at concentrations of 10 nM (FIG. 17B) and 200 nM (FIG. 17B), respectively, and the inhibition of such binding by Erbitux.
Figure 15B:
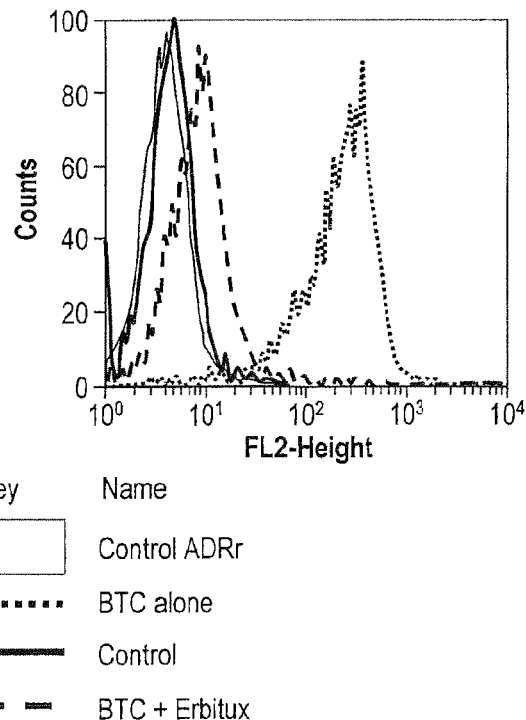
Figure 15C:
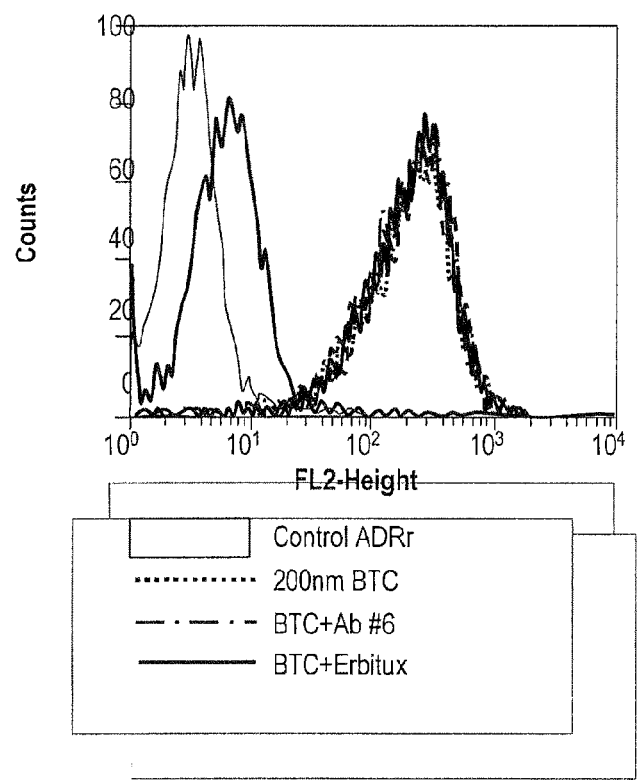

The results of this experiment are depicted in FIGS. 15A-15C. As shown in FIG. 15A, betacellulin (BTC) does not show any appreciable binding to ErbB1 negative MALME-3M cells. However, as depicted in FIGS. 15B and 15C, BTC does show binding to ErbB1 positive ADRr cells.

Also, as shown in FIGS. 15B and 15C, this binding was blocked by Erbitux, which is an anti-EGFR antibody which specifically binds EGFR and was included as a control to demonstrate that EGF-like ligands bind to EGFR, and which is described in e.g., Adams et al. (2005), *Nature Biotechnology* 23, 1147-1157.

Example 8

Inhibition of Heregulin-Mediated Signaling in Tumor Cells

The ability of Ab #6 to inhibit heregulin-mediated tumor cell signaling was investigated as follows.

MALME-3M cells were seeded in 96 well tissue culture plates and grown in RPMI-1640 media supplemented with antibiotics, 2 mM L-glutamine and 10% fetal bovine serum (FBS) for 24 hours at 37° C. and 5% carbon dioxide. Cells were serum starved in RPMI-1640 media with antibiotics and 2 mM L-glutamine for 24 hours at 37° C. and 5% carbon dioxide. Cells were pre-treated with and without the anti-ErbB3 antibody (IgG2 isotype of Ab #6) at 1 µM, 250 nM, 63 nM, 16 nM, 4.0 nM, 1.0 nM, 240 pM and 61 pM concentrations for 30 minutes then stimulated with HRG1-beta1-ECD for 10 minutes at 37° C. and 5% carbon dioxide. Cells were washed with cold PBS then harvested with mammalian protein extract (MPER) lysis (Pierce, 78505) buffer containing 150 mM NaCl 5 mM sodium pyrophosphate, 10 uM bpV (phen), 50 µM phenalarsine, 1 mM sodium orthovanadate, and protease inhibitor cocktail (Sigma, P714). Cell lysates were diluted two-fold with 4% bovine serum albumin in phosphate buffered saline with 0.1% tween-20, then analyzed by ELISA for AKT (a downstream effector of ErbB3) and ErbB3 phosphorylation.

In order to test for AKT phosphorylation, lysates were run on an ELISA plate with a capture antibody specific for AKT and biotinylated detection antibody specific to the phosphorylation site on serine 473 of AKT. Signal was generated with streptavidin conjugated to horseradish-peroxidase reacted with chemiluminescent substrate (Pierce, 37070). In order to assay for ErbB3 phosphorylation, lysates were run on an ELISA plate with a capture antibody specific for ErbB3 and an anti-phosphotyrosine detection antibody conjugated to horseradish-peroxidase. This was then reacted with chemiluminescent substrate (Pierce, 37070). ELISAs were visualized using a luminometer.

Figures 16A, 16B:
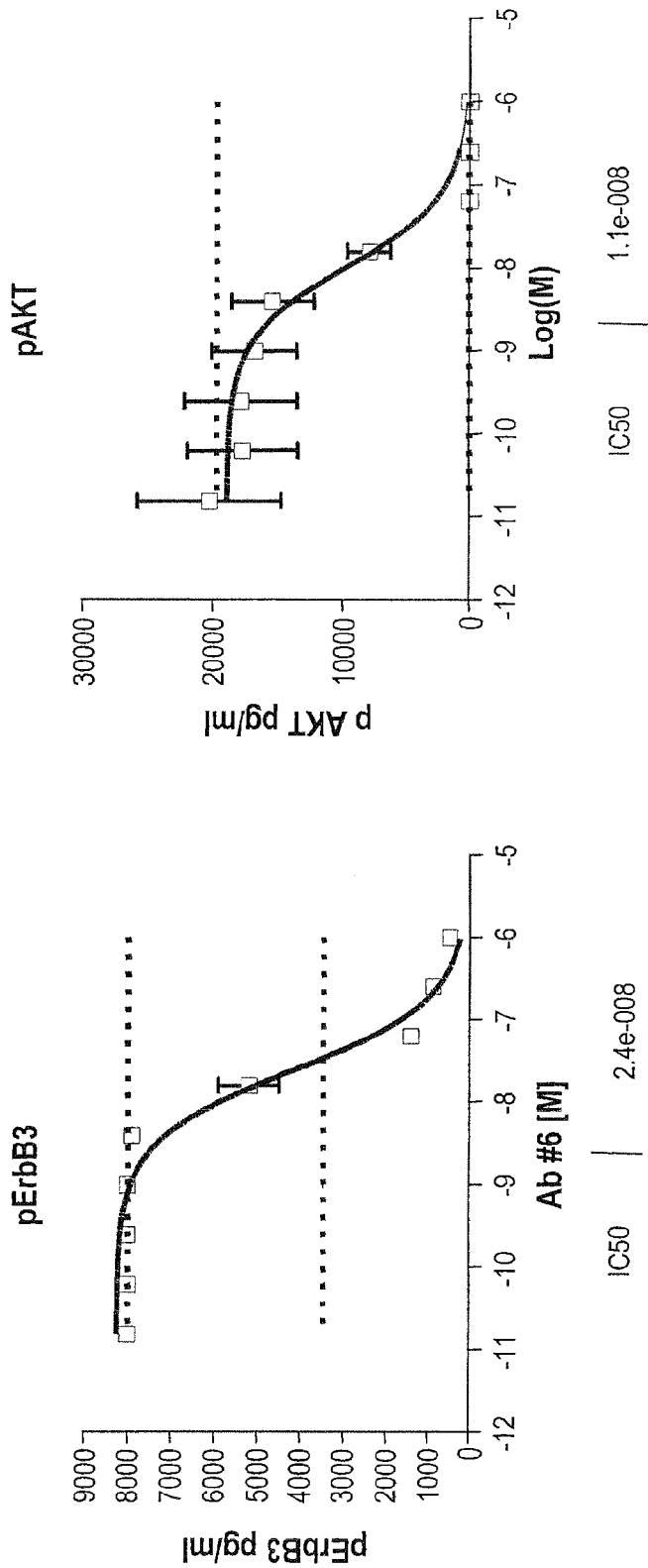
FIGS. 16A-16B are graphs depicting the ability of an anti-ErbB3 antibody (Ab #6 IgG2 isotype) to inhibit heregulin-mediated signaling in MALME-3M cells.

As shown in FIGS. 16A and 16B, Ab #6 was a potent inhibitor of heregulin-mediated signaling in MALME-3M cells, as measured by decreased phosphorylation of ErbB3 (FIG. 16A) and AKT (FIG. 16B). Notably, Ab #6 inhibited the phosphorylation of AKT by almost 100%.

Example 9

Inhibition of Ovarian, Prostate, and Pancreatic Tumor Growth

To assess the efficacy of Ab #6 in vivo, several xenograft models of human cancer were established in nude mice and the inhibition of tumor growth was assessed at multiple doses. For example, T-cell deficient nu/nu mice (3-4 week old female mice originated at NIH; outbred; albino background) were purchased from Charles River Labs (Wilmington, Mass.) for xenograft studies. ADRr cells for implantation were grown in culture (RPMI media, 10% FBS, L-glutamine and antibiotics, 37° C., 5% CO2) to about 85% confluency before harvesting. Cells were kept on ice until implantation. Mice were implanted via subcutaneous injection with 100 µl ADRr cells on the right flank and allowed to recover while being monitored for initial tumor growth.

Tumors were measured (length by width) by digital caliper and the mice were dosed with IgG2a (Sigma, M7769-5MG) by intravenous injection. Mice were dosed intra-peritoneally every third day with either 30 µg or 300 µg of Ab #6 and tumors were measured three times per week and recorded in a Microsoft Excel spreadsheet.

Final tumor measurements (L×W) were taken, the mice were euthanized by CO2 asphyxiation and tumors were excised, snap frozen in liquid nitrogen, and were stored at −80° C. (for biochemical analysis). Final tumor measurements were analyzed and graphed by tumor area and tumor volume, as described in Burtrum et al., supra. The data was also analyzed by "normalized' and "non-normalized" means for both tumor volume and tumor area. For the "normalization" of the data, at each time point of measurement, each tumor in each group was divided by the initial tumor size determined by caliper measurement.

Figure 17A:
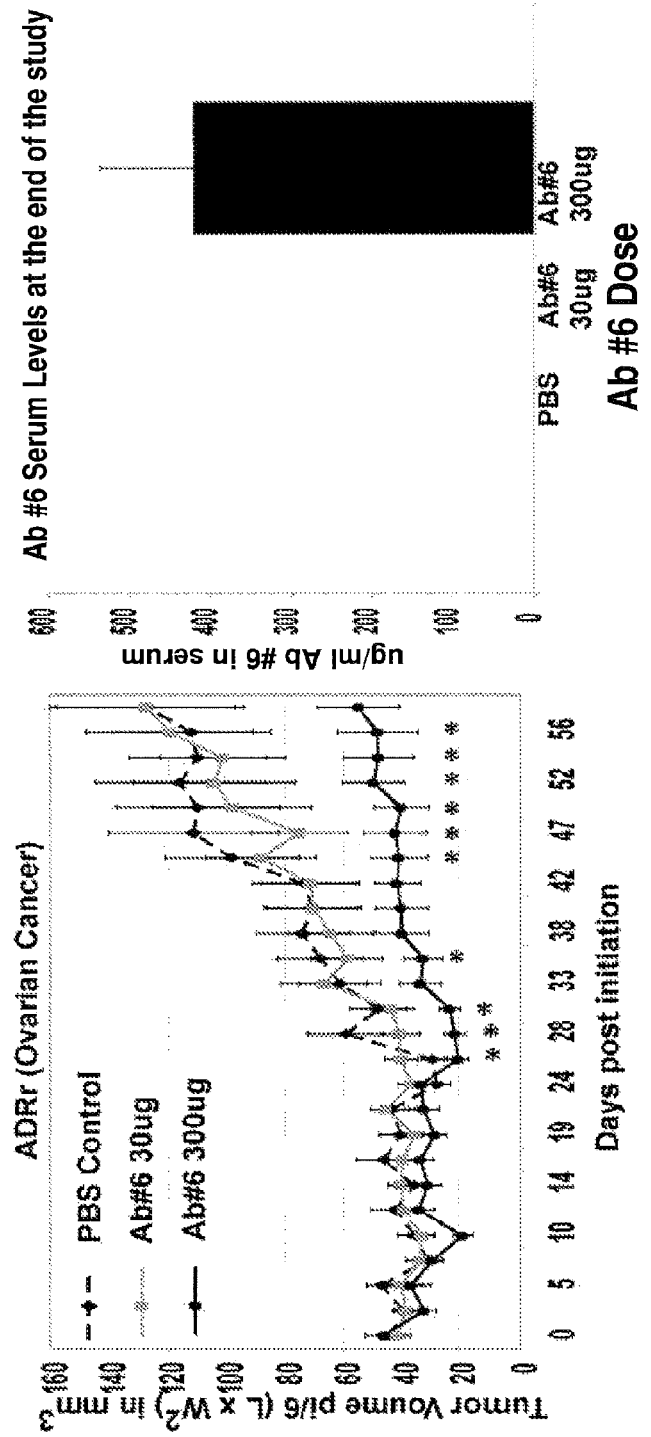
FIGS. 17A-D are graphs depicting the ability of an anti-ErbB3 antibody (Ab #6) to inhibit (A) ovarian (ADRr cells), (B) prostate Du145 cells), (C) ovarian (OvCAR8 cells), and (D) pancreatic (Colo357 cells) tumor growth via xenograft studies.
Figure 17B:
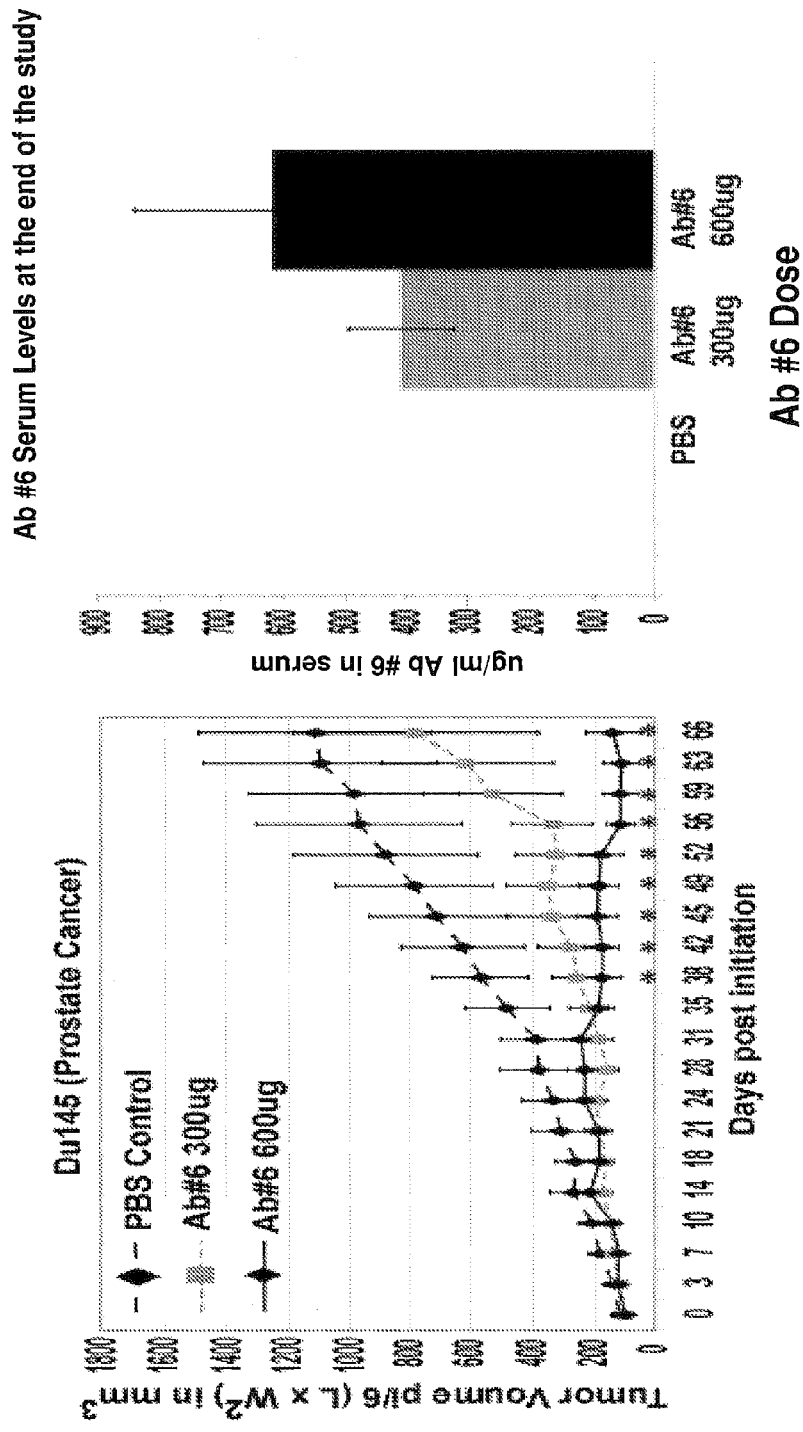
Figure 17C:
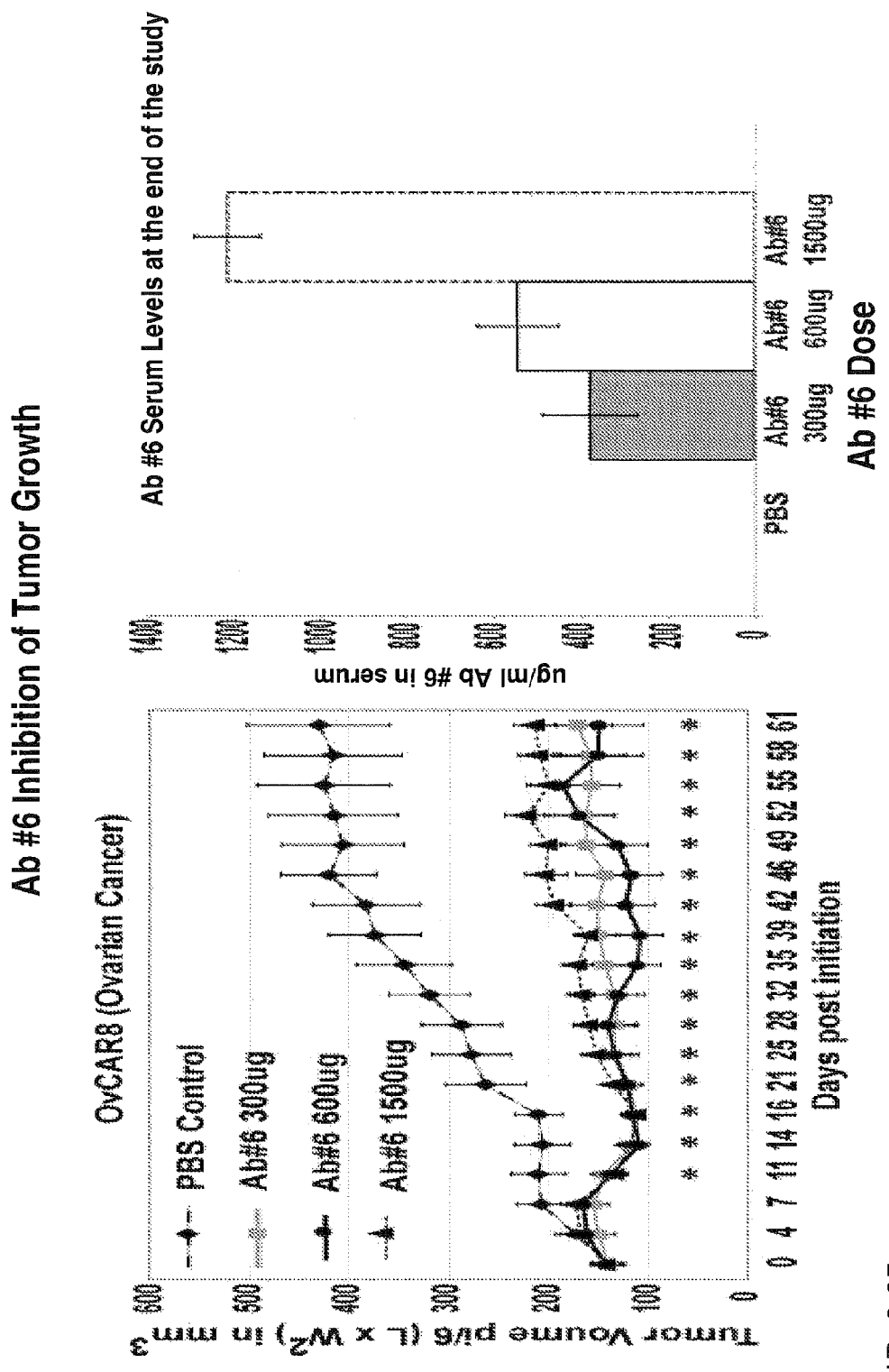
Figure 17D:
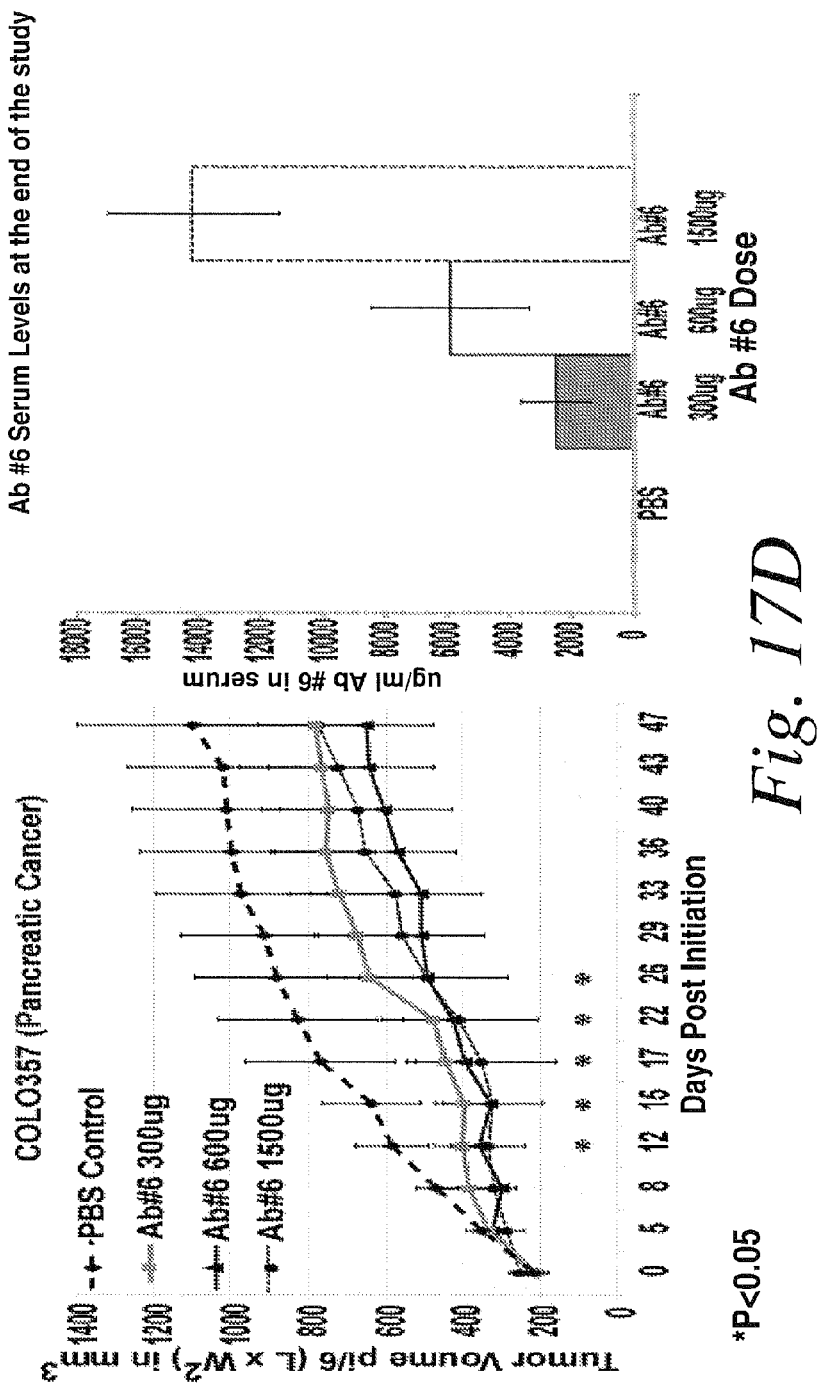

The data from three different models derived from human tumor cell lines, ADRr (ovarian), Du145 (prostate) and OvCAR8 (ovarian) are shown in FIGS. 17A-C and Colo357 xenograft study is shown in FIG. 17D. The data from these studies demonstrated that a 300 ug dose of Ab #6 every three days (Q3d) results in significant inhibition of tumor growth ($p<0.05$ for multiple time points during the studies). Moreover, this inhibitory effect of Ab #6 was further elevated when the dose was increased to 600 ug, Q3d, in the Du145 prostate cancer model as well as a renal and a pancreatic carcinoma xenograft model (ACHN and COL0357). However, further elevating the dose to 1500 ug Q3d did not result in increased efficacy (OvCAR8-FIG. 17; COLO357) suggesting that the 600 ug is saturating in regards to tumor growth inhibition. Pharmacokinetic (PK) analyses of the serum from the animals from these studies demonstrate a dose-dependent increase in the serum retention of Ab #6. Similarly, biochemical analysis of the intra-tumoral levels of Ab #6 from these different studies showed a dose-dependent range of 0 to ~6 pg MM121/ug of total tumor lysate (data not shown).

Example 10

Inhibition of Binding of ErbB3 Ligands to ErbB3 on Tumor Cells

In a further experiment, the specificity of the antibodies of the invention to inhibit the binding of ErbB3 ligands to ErbB3, and not EGF-like ligands to EGFR, was investigated as follows.

In one experiment, the specificity of Ab #6 and a Fab version of Ab #3 (Ab/Fab #3) to inhibit the binding of ErbB3 ligands (e.g., heregulin and epiregulin) to ErbB3 was investigated.

In order to investigate the ability of Ab #6 and Ab/Fab #3 to inhibit the binding of heregulin to ErbB3, the following experiment was performed.

ADRr cells ($1 \times 10^5$) were incubated with 10 µM of an anti-ErbB3 antibody (e.g., Ab #6 or Ab/Fab #3) in 50 µl BD stain buffer for 30 minutes on ice. After 30 minutes, 50 µl of 40 nM biotinylated heregulin EGF was added to the cells and incubated for another 10 minutes on ice. This gave a final concentration of 5 µM antibody and 20 nM heregulin EGF. Cells were then washed twice with 500 µl BD stain buffer and incubated with 100 µl of a 1:200 dilution of streptavidin-PE (PE=phycoerythrin) (Invitrogen) in BD stain buffer for 45 minutes. Finally, cells were washed twice, resuspended in 300 µl of BD stain buffer and analyzed in a FACScalibur flow cytometer. As a positive control, $1 \times 10^5$ ADRr cells were incubated with 20 nM heregulin EGF for 10 minutes on ice, washed twice and incubated with a 1:200 dilution of streptavidin-PE for 45 minutes. In order to assess background staining from the streptavidin-PE conjugate, $1 \times 10^5$ ADRr cells were incubated with 100 µl of a 1:200 dilution of streptavidin-PE only for 45 minutes.

The results of this experiment are shown in FIGS. 18A and 18B. As depicted in FIGS. 18A and 18B, both Ab #6 and Ab/Fab #3 were able to inhibit heregulin binding to ErbB3.

Similarly, the ability of Ab #6 to inhibit the binding of another ErbB3-ligand, epiregulin, to ErbB3, was examined as follows.

ADRr cells ($1 \times 10^5$) were pre-incubated with 25 µM of Ab #6 or 25 µM of Erbitux (as control) in 50 µl BD stain buffer for 30 minutes on ice. After 30 minutes, 50 µl of 2 µM biotinylated Epi was added to the cells and incubated for another 30 minutes on ice. This gave a final concentration of 12.5 µM antibodies and 1 µM Epi. Cells were then washed twice with 500 µl BD stain buffer and incubated with 100 µl of a 1:200 dilution of streptavidin-PE (PE=phycoerythrin) (Invitrogen) in BD stain buffer for 45 minutes. Finally, cells were washed twice, resuspended in 300 µl of BD stain buffer and analyzed in a FACScalibur flow cytometer. As a positive control, $1 \times 10^5$ ADRr cells were incubated with 1 µM Epi for 30 minutes on ice, washed twice and incubated with a 1:200 dilution of streptavidin-PE for 45 minutes. To assess background staining from the streptavidin-PE conjugate, cells were incubated with 100 µl of a 1:200 dilution of streptavidin-PE only for 45 minutes.

Figures 19A, 19B:
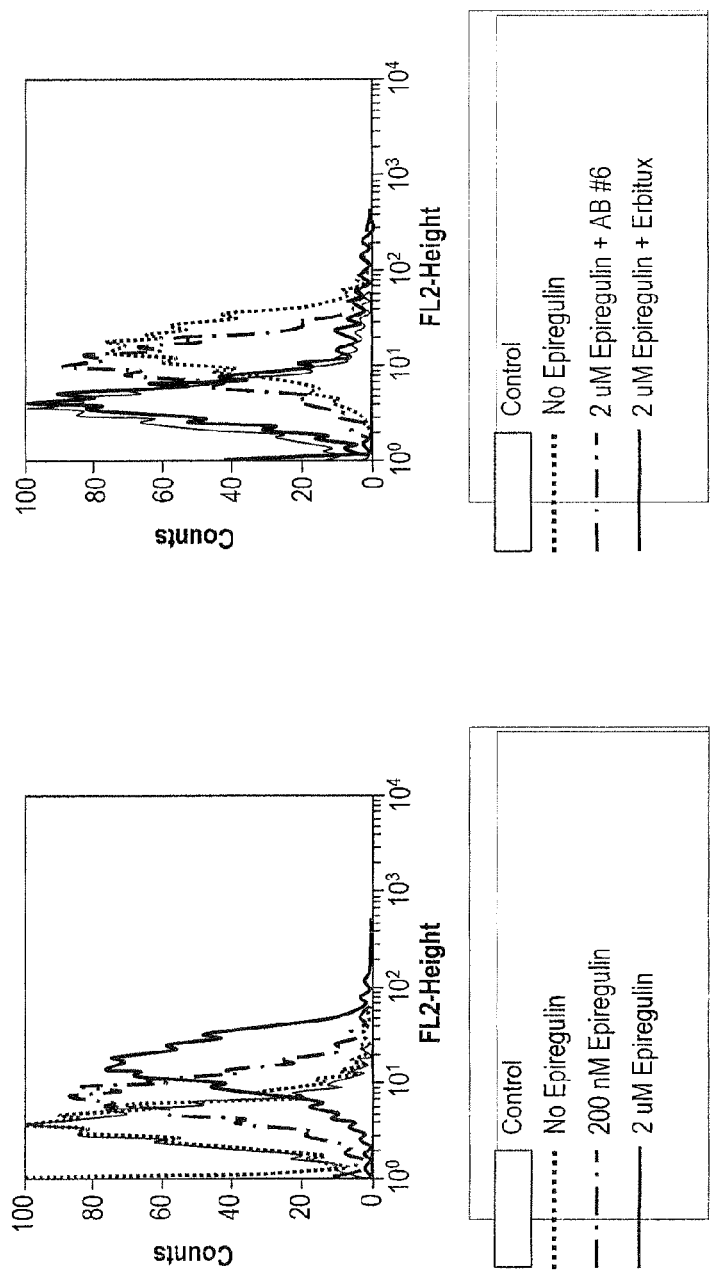
FIGS. 19A and 19B are graphs depicting the ability of Ab #6 to inhibit the binding of epiregulin to ErbB3 on ADRr cells.

The results of this experiment are depicted in FIGS. 19A and 19B. As shown in FIG. 19A, epiregulin binds to ErbB3 positive ADRr cells. Further, as shown in FIG. 19B, this binding is inhibited by both Erbitux and Ab #6, suggesting that epiregulin may bind to both EGFR and ErbB3.

A further experiment was performed to investigate whether Ab #6 is able to inhibit the binding of an EGF-like ligand (e.g., HB-EGF) to tumor cells.

ADRr cells ($1 \times 10^5$) were pre-incubated with 25 µM of Ab #6 or 25 µM of Erbitux (as control) in 50 µl BD stain buffer for 30 minutes on ice. After 30 minutes, 50 µl of 400 nM biotinylated HB-EGF was added to the cells and incubated for another 30 minutes on ice. This gave a final concentration of 12.5 µM antibodies and 200 nM HB-EGF. Cells were then washed twice with 500 µl BD stain buffer and incubated with 100 µl of a 1:200 dilution of streptavidin-PE (PE=phycoerythrin) (Invitrogen) in BD stain buffer for 45 minutes. Finally, cells were washed twice, resuspended in 300 µl of BD stain buffer and analyzed in a FACScalibur flow cytometer. As a positive control, $1 \times 10^5$ ADRr cells were incubated with 200 nM HB-EGF for 30 minutes on ice, washed twice and incubated with a 1:200 dilution of streptavidin-PE for 45 minutes. To assess background staining from the streptavidin-PE conjugate, cells were incubated with 100 µl of a 1:200 dilution of streptavidin-PE only for 45 minutes.

Figure 20B:
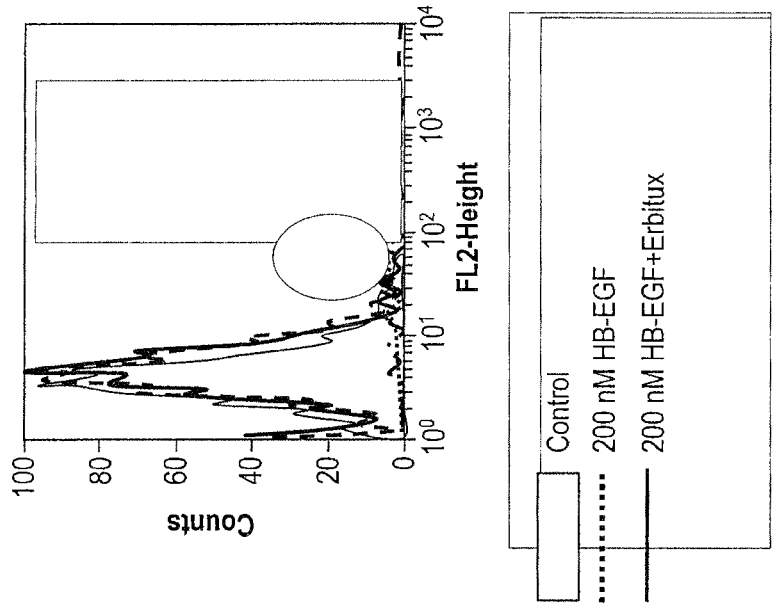
FIGS. 20A and 20B are graphs depicting the ability of heparin binding epidermal growth factor (HB-EGF) to bind ErbB on ADRr cells (FIG. 20A) and the inability of an anti-ErbB3 antibody (Ab #6) to inhibit such binding (FIG. 20B).
Figure 20A:
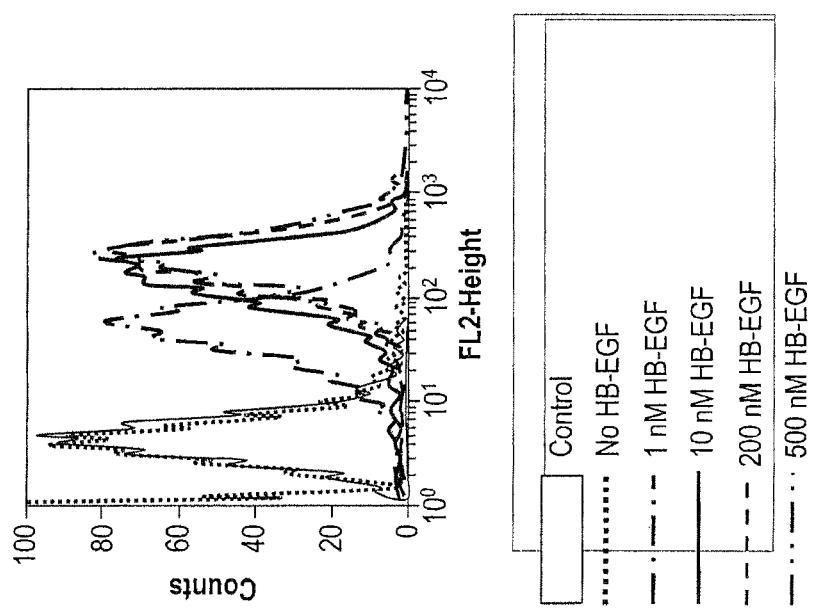

As shown in FIGS. 20A and 20B, HB-EGF binds to ErbB on ADRr cells and Ab #6 does not inhibit this binding, evidencing that Ab #6 is specific for inhibiting the binding of ErbB3 ligands (e.g., heregulin and epiregulin) to ErbB3.

Example 11

Inhibition of VEGF Secretion in Tumor Cells

Figure 24A:
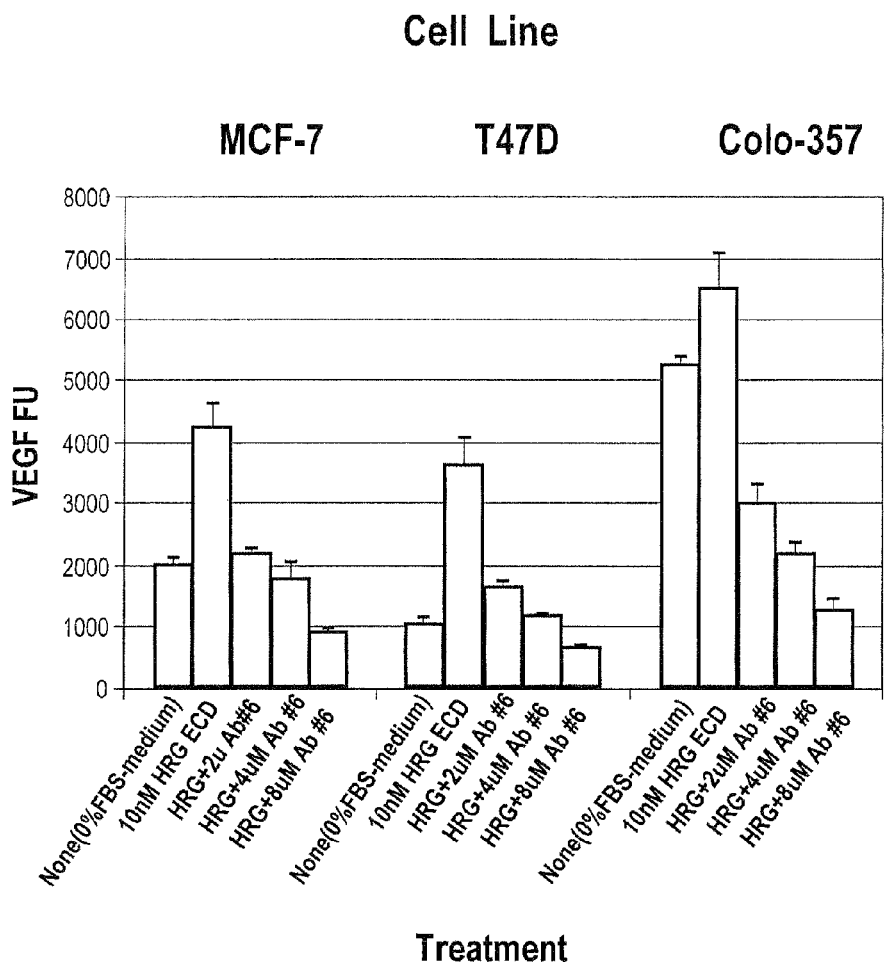
FIGS. 24A-24C are graphs showing the ability of Ab #6 to inhibit VEGF secretion of tumor cells.

The ability of Ab #6 to inhibit VEGF secretion of cells expressing ErbB3 (e.g., cancer cells) was examined using VEGF secretion assay (VEGF ELISA kit available from R&D Systems, Minneapolis, Minn., Cat. #DY293B). First, the ability of Ab #6 to inhibit VEGF secretion in the untreated and HRG—beta1 treated MCF-7, T47D, and COLO-357 cells was analyzed. These studies revealed that COLO-357 secreted the highest amount of VEGF into the media. As these cells also had very high HRG levels (data not shown), addition of HRG to the media was not able to further induce VEGF secretion (FIG. 24A). In contrast, HRG was able to induce VEGF secretion in MCF-7 and T47D cells.

Figure 24B:
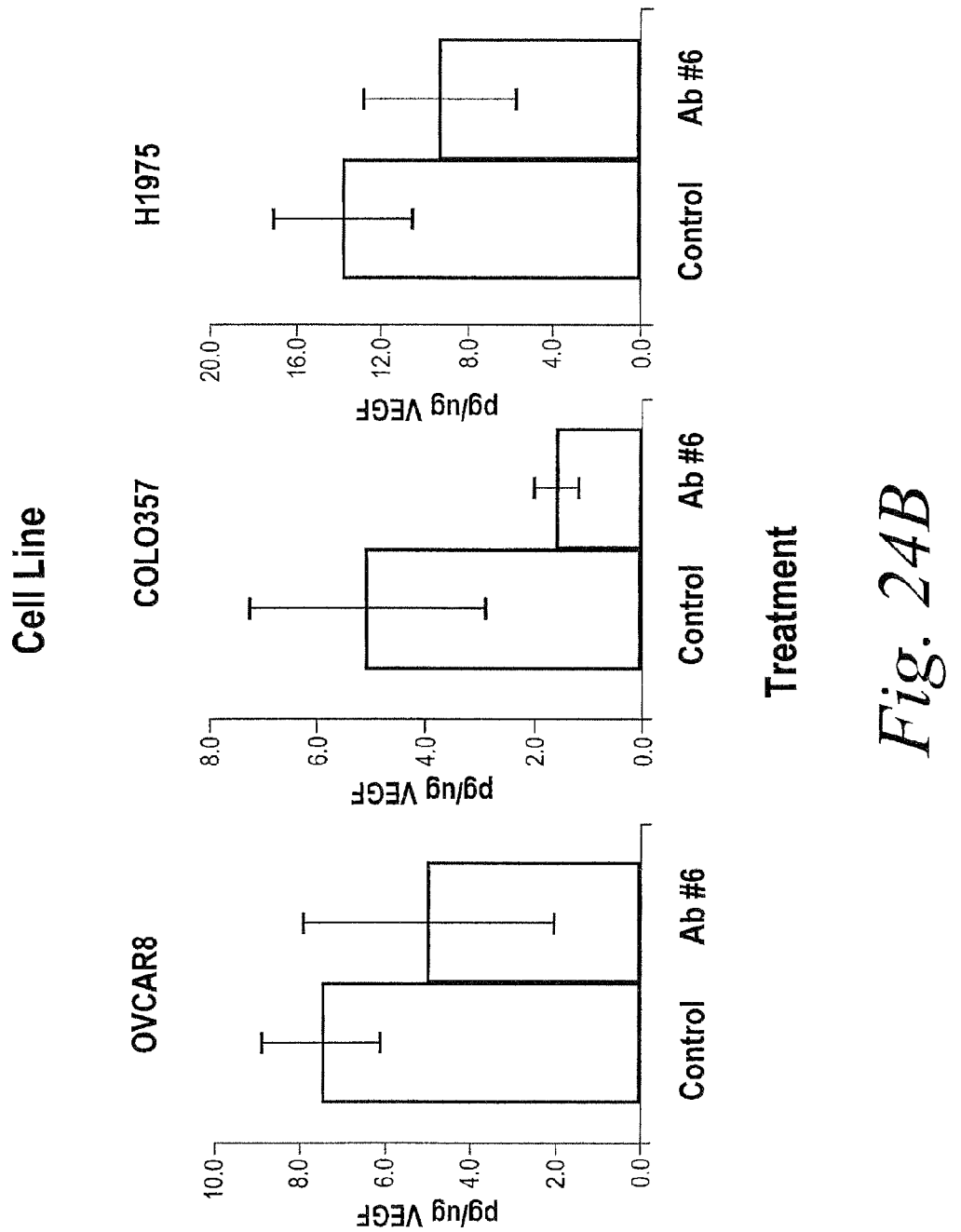
Figure 24C:
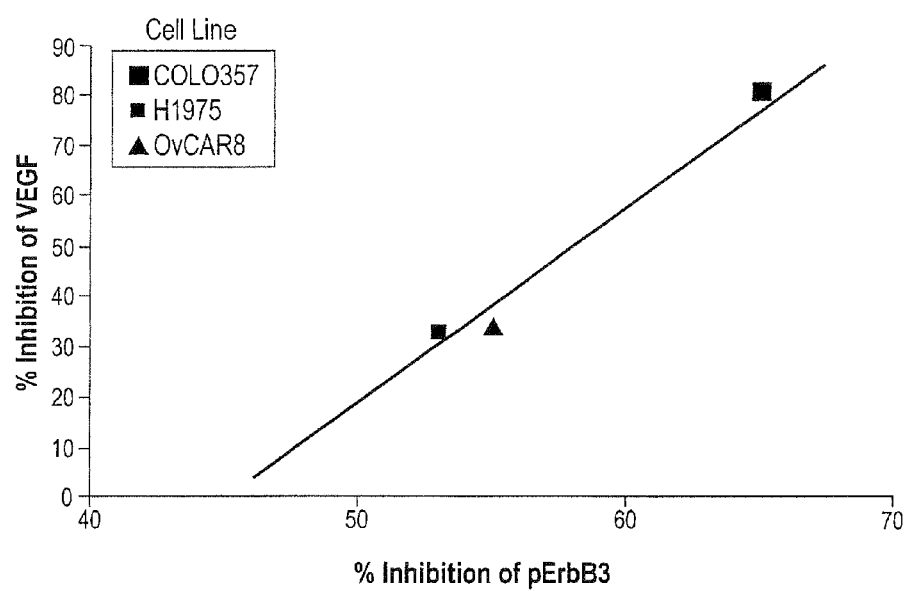

Ab #6 shows a potent inhibitory effect at high levels in all three cell lines with the highest being in COLO-357 (FIG. 24A). Ab #6 also shows a similar effect in vivo by inhibiting VEGF secretion in three different xenografts, the highest being in COLO-357 xenograft (FIG. 24B). Inhibition of VEGF correlates with inhibition of ErbB3 phosphorylation (FIG. 24C). Inhibition of VEGF secretion also correlates with inhibition of angiogenesis of the tumor cells. In particular, it has been identified that myeloma cell-secreted factors, such as VEGF and bFGF, trigger angiogenesis (see, e.g., Leung et al. (1989) Science 246(4935):1306-9; Yen et al. (2000) Oncogene 19(31):3460-9).

Example 12

Inhibition of Cell Migration

The ability of Ab #6 to inhibit the migration of cells expressing ErbB3 (e.g., MCF-7 cells) was examined using a trans-well assay (Millipore Corp., Billerica, Mass., Cat #ECM552). First, MCF-7 cells were serum-starved overnight and then incubated in the presence or absence of Ab #6 (8 uM final concentration) for 15 minutes at room temperature. The cells were then transferred to an upper chamber that is separated from a lower chamber by a collagen type I-coated membrane through which the cells can migrate. 10% FBS was added to media in the lower chamber to act as a chemoattractant in the presence of absence of Ab #6. The chambers were incubated at 37° C. for 16 hours and then the cells that migrated through the membrane were removed using a detachment buffer and incubated with a cell-binding fluorescent dye. Fluorescence was quantitated using a fluorescent plate reader. The average fluorescence±SEM (n=2) is shown in FIG. 25.

Figure 25:
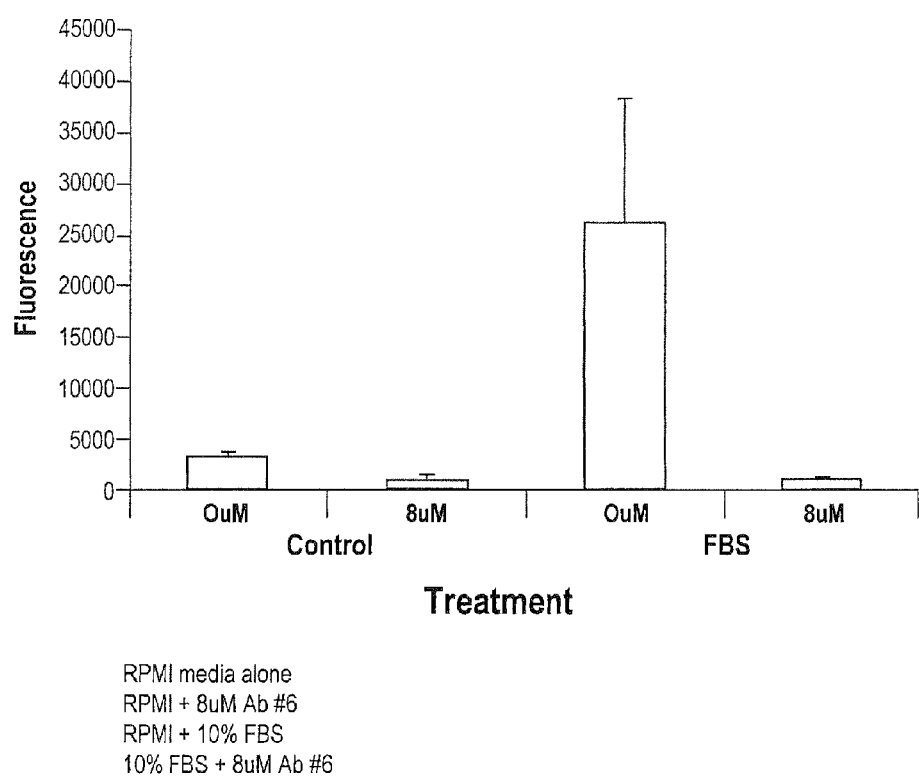
FIG. 25 is a graph showing the effect of Ab #6 on cell migration.

As shown in FIG. 25, 10% FBS stimulates cell migration (lane 3) as compared to untreated control (lane 1) and 8 uM Ab #6 inhibits the FBS induced cell migration (lane 4).

Example 13

Inhibition of Spheroid Growth

The ability of Ab #6 to inhibit the spheroid growth of cells expressing ErbB3 was examined using an assay which approximates conditions of a developing tumor growth (Herman et al. (2007) Journal of Biomolecular Screening Electronic publication). AdrR (an ovarian cancer cell line) and DU145 (a prostate cancer cell line) spheroids were initiated at a frequency of 1 spheroid per well of a 96 well plate using the hanging drop method (Herrman et al., 2008). Individual spheroids were then treated with either Ab #6 (8 uM final concentration), Heregulin-β1 EGF domain (R&D Systems, Minneapolis, Minn., Cat #396-HB, 3.4 nM final concentration), or a combination of both, as indicated. The diameters of the spheroids were measured using light microscopy (10× objective) at day 1 and day 13.

Figure 26A:
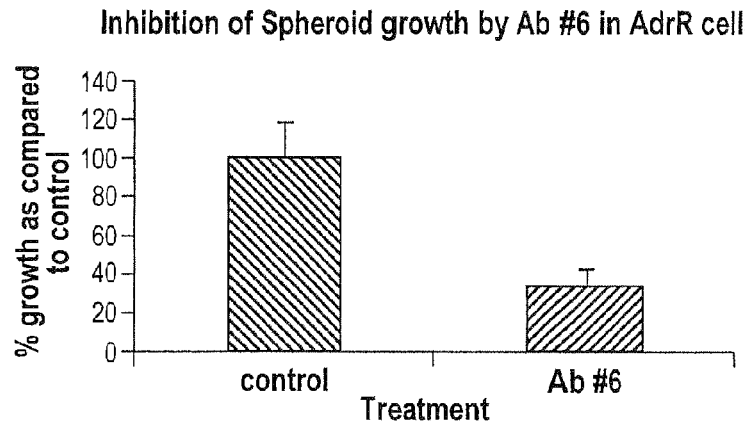
FIGS. 26A-C are graphs showing (A) inhibition of spheroid growth in AdrR cells, (B) inhibition of HRG induced spheroid growth in AdrR, and (C) inhibition of HRG induced spheroid growth in Du145 cells.
Figure 26B:
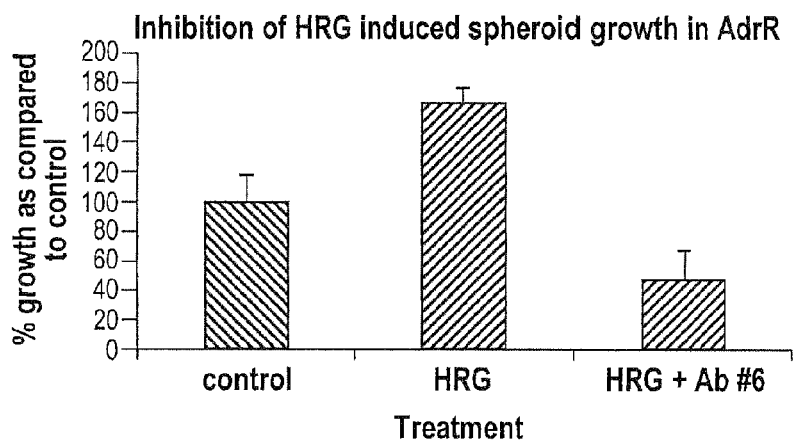
Figure 26C:
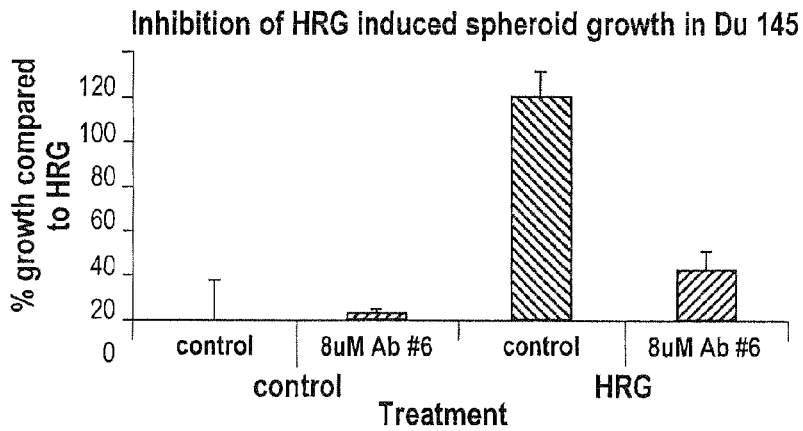

Ab #6 inhibits spheroid growth in AdrR cells (FIG. 26A). In addition, 3.4 nM HRG stimulates spheroid growth and Ab #6 inhibits the HRG effect (FIG. 26B). Spheroids derived from DU145 did not increase in size during 13 days of the experiment; however, growth was significantly stimulated by HRG1-beta 1. In these cells, 8 uM Ab #6 inhibits HRG induced spheroid growth (FIG. 26C).

In additional experiments, the ability of Ab #6 to inhibit spheroid growth of OVCAR8 cells, another human ovarian cancer cell line, was examined. Again, multicellular tumor spheroids were generated by the hanging drop method (Kelm, J. M. et al. (2003) *Biotechnol. Bioeng.* 83:173-180). Briefly, subconfluent cells were trypsinized, counted, and resuspended in filtered medium. The cell concentration was adjusted to 50,000 cells/ml, and one 20 µl drop (containing 1000 cells) was added to each ring on the underside of the lid of a 48-well plate. The lids with these hanging droplets were then placed back on the original 48-well plate, which contained 300 µl of PBS in each well to maintain moisture. Four days after initial plating, the hanging droplets containing the spheroids were replated into new 48-well plates. This replating involved transferring the lid containing the hanging droplets to a fresh 1% agarose/RPMI-coated 48-well plate that contained 300 µl of media per well. The plate and lid were then centrifuged together at 500 rpm for 1 minute to transfer the spheroid-containing drops from the lids to the wells. Plates were then further incubated at 37° C. in a humidified $CO_2$ incubator. Spheroids were photographed in an inverted phase contrast microscope. A micrometer scale was also photographed at the same magnification to determine spheroid size. To test the effect of Ab #6 on spheroid growth, the antibody was added to a final concentration of 25 µg/ml on days 1 and 4 of spheroid formation. Addition of Ab #6 to the cells resulted in a consistent decrease in OVCAR8 spheroid growth.

Example 14

Inhibition of Signaling

Figure 27A:
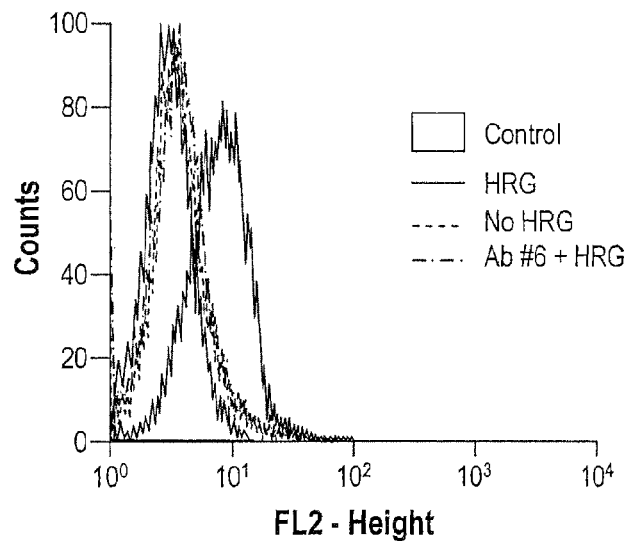
FIGS. 27A and B are graphs showing the effect of Ab #6 on (A) HRG and (B) BTC binding to AdrR cells.
Figure 27B:
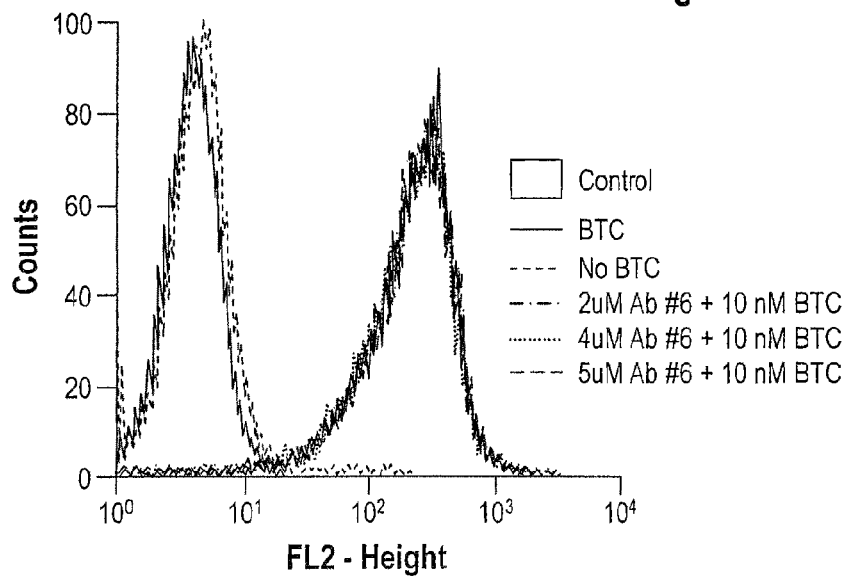

The ability of Ab #6 to inhibit the signaling induced by different ligands was examined. For example, the effect of Ab #6 on HRG and BTC binding to AdrR cells expressing ErbB3 receptor was tested. As shown in FIGS. 27A and B, using FACS analysis, Ab #6 competes with HRG and not BTC for binding to AdrR cells. Accordingly, blocking by Ab #6 of HRG binding to ErbB3 would prevent signaling induced by HRG.

Figure 28:
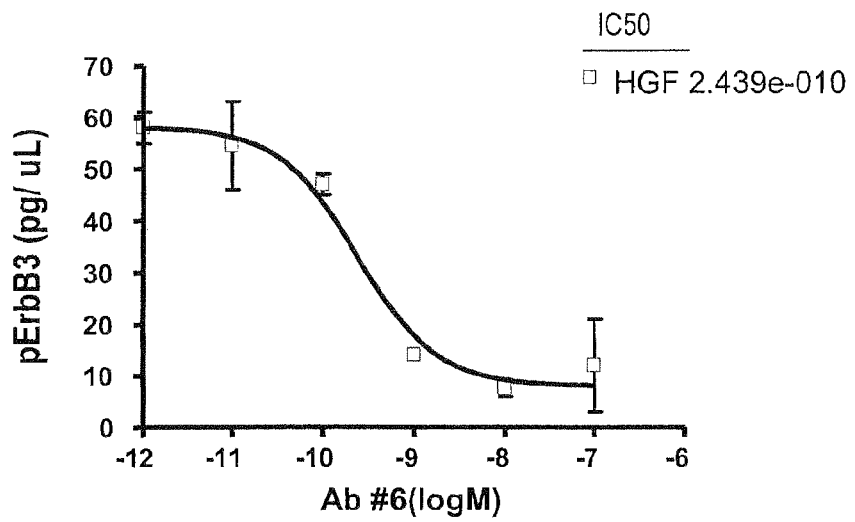
FIG. 28 is a graph showing the effect of Ab #6 on HGF induced ErbB3 phosphorylation.

Additionally, various ligands were tested for inducement of ErBb3 phosphorylation. Three ligands, HRG, BTC, and HGF, were able to stimulate ErbB3 induced phosphorylation in AdrR cells, while EGF could not. As shown in FIG. 28, Ab #6 inhibits HGF induced pErbB3 phosphorylation in AdrR cells (FIG. 28). Further, as known in the art (see, e.g., Wallenius et al. (2000) Am J Pathol. 156 (3):821-9 10702398), enhanced HGF signaling has been found in various epithelial and non-epithelial tumors.

ErbB3/cMET Interaction and the Role of Ab #6 in Modulating this Interaction

It has been shown that non-small-cell lung cancers carrying activating mutations in the epidermal growth factor receptor (EGFR) develop resistance to tyrosine kinase inhibitors by recruiting MET and HER3 and thus activating the PI3K-AKT cell survival pathway (Engelmann et al. (2007) Science 316: 1039-1043; Gou (2007) PNAS: 105(2): 692-697). The association between EGFR and c-MET in cell lines that carry activating EGFR mutations has been well established by co-immunoprecipitation (Engelmann et al. 2007; Gou 2007). Guo et al. recently demonstrated that c-MET and ErbB3 also exist in a complex in a gastric cell line MKN45 known to be dependent on amplified c-MET, using co-immunoprecipitation.

This c-MET-erbB3 interaction occurs also in AdrR cells carrying the wild type EGFR and is not dependent on amplified c-MET. HGF (Hepatocyte Growth Factor) induces ErbB3 phosphorylation in AdrR cells in a dose dependent manner as shown in FIG. 28. In addition, Ab #6 inhibits HGF induced erbB3 phosphorylation.

Figure 29A:
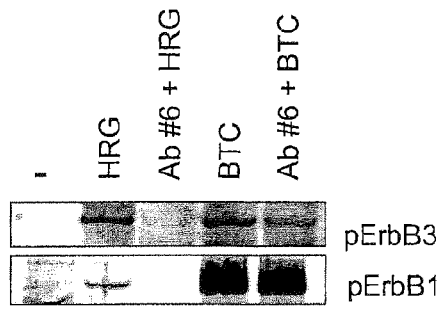
FIGS. 29A and B show the effect of Ab #6 on phosphorylation of (A) pErbB1 and pErbB3 and (B) HRG induced ErbB2/3 complex formation.

The effect of HRG and BTC on both ErbB1 and ErbB3 phosphorylation has also been investigated, and HRG and BTC were found to induce phosphorylation of both ErbB1 and ErbB3. HRG was found to be a more potent inducer of ErbB3 phosphorylation while BTC was a potent inducer of ErbB1 phosphorylation (FIG. 29). This phosphorylation is likely to be driven by the complex between ErbB1 and ErbB3. Briefly, HRG binding to ErbB3 induces complex formation between ErbB1 and ErbB3, leading to the activation of both receptors. The same phenomenon appears likely for BTC, where BTC binding to ErbB 1 stimulates complex formation between ErbB 1 and ErbB3, leading to the phosphorylation of both ErbB1 and ErbB3.

Antibody Inhibition of Ligand (HRG, BTC, EGF, and HGF) Stimulated ErbB3 Phosphorylation.

The ability of Ab #6 to inhibit ligand (HRG, BTC, EGF, and HGF) induced ErbB3 phosphorylation was examined based on the following method:
1. AdrR cells were plated into 96 well plate at a density of 30,000 cells/well/100 uL in RPMI medium containing 10% FBS and allowed to grow overnight;
2. The next day, cells were serum-starved by changing medium to FBS-free medium and allowed to grow overnight;

3. Cells were pre-treated with different concentrations of Ab #6 (from 0.01 nM to 100 nM), or buffer (control), for 2 hours;
4. The cells were then stimulated with 10 nM HRG and HGF for 10 minutes, or 10 nM BTC and EGF for 5 minutes;
5. The reaction was stopped by removing the culture medium and washing the cells once with ice cold PBS;
6. The cells were then lysed in 25 mM Tris, pH+7.5, 150 mM NaCl, 1 mM EDTA, 1.0% Triton X-100, 1.0% CHAPS, 10% v/v glycerol, containing 1× protease inhibitor and 1× phosphatase inhibitor; and
7. ErbB3 phosphorylation was measured in cell lysates using Human Phospho-ErbB3 ELISA kit (R&D Systems, Minneapolis, Minn., Cat. No. DYC1769) according to manufacturer's instructions.

Antibody Inhibition of ErbB2-ErbB3 Protein Complex Formation.

AdrR cells were pre-incubated with buffer (control), or 250 nM Ab #6 for 60 minutes at room temperature, then treated with 10 nM HRG or 10 nM BTC or control buffer for 10 minutes. The cells were lysed in 25 mM Tris, pH+7.5, 150 mM NaCl, 1 mM EDTA, 1.0% Triton X-100, 1.0% CHAPS, 10% v/v glycerol, containing 0.2 mM PMSF, 50 mTU/mL aprotinin, and 100 uM leupeptin, and the crude lysate were centrifuged briefly to remove insoluble material. Supernatant was transferred to a new eppendorf tube, and anti-ErbB3 antibody (Santa Cruz sc-285) was added at 1:500 dilution. Supernatants were incubated overnight with gentle shaking at 4 C. 60 ul of Immobilized Protein A/G agarose beads (Pierce, Rockford, Ill., Cat #20421) was first washed with 1×PBS. The cell lysate-antibody mixture was added to the PBS washed beads, and incubated for 2 hours with gentle shaking at 4° C. The immunoprecipitates were then washed with ice-cold lysis buffer 3 times, resuspended in 30 ul of 2×SDS sample buffer, heat denatured at 95° C. for 7 minutes and run on 4-12% Bis-Tris Gels. SDS-PAGE and electro-transferred to PVDF membrane in Tri-Glycine buffer with 10% MeOH. The membrane was blocked for 1 hour in 10 ml of blocking buffer (Li-Cor Biosciences, Lincoln, Nebr., Cat #927-40000) and then incubated with the anti-ErbB2 antibody at 1:1000 (Cell Signaling Technology, Danvers, Mass., Cat #29D8) in 10 ml of blocking buffer (Li-Cor Biosciences, Cat #927-40000). The signal was detected using goat anti-rabbit IRDye800 at 1:5000 (2 ul) in 10 ml of blocking buffer (Li-Cor Biosciences, Cat #927-40000).

Figure 29B:
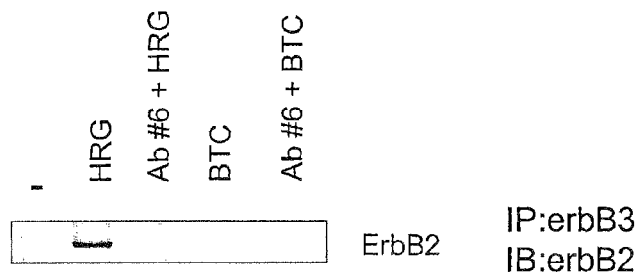

Ab #6 was also shown to completely inhibit HRG stimulated ErbB2/3 complex formation (FIG. 29B).

Example 15

Inhibition Profile of Ab #6 is Distinct from Cetuximab, Lapatinib and Pertuzumab In this example, inhibitor dose response studies were performed with ADRr cells stimulated with either HRG1-beta or betacellulin (BTC) in the presence of either Ab #6, cetuximab, lapatinib or pertuzumab. Serum starved ADRr cells were pre-incubated for 30 minutes with 4-fold serial dilutions of Ab #6, lapatinib or cetuximab from 2 mM to 7.6 pM or of pertuzumab from 100 nM to 1.5 pM and then stimulated for 10 minutes with 25 nM of HRG1-beta or BTC. Phosphorylation of ErbB3 was measured by ELISA and $IC_{50}$ values were determined.

Ab #6 was able to inhibit both HRG1-beta-induced ErbB3 phosphorylation and BTC-induced ErbB3 phosphoryation, with $IC_{50}$s of 2.4 nM and 5.9 nM, respectively (with 95% confidence intervals of 1.5-3.8 nM and 2.5-13.6 nM, respectively). Lapatinib (a reversible tyrosine kinase inhibitor of ErbB1 and ErbB2) was able to inhibit HRG1-beta and BTC-induced ErbB3 phosphorylation with $IC_{50}$s of 150 nM and 360 nM, respectively (with 95% confidence intervals of 46-504 nM and 119-1069 nM, respectively). Cetuximab (an anti-ErbB1 antibody) was able to inhibit only BTC-induced ErbB3 phosphorylation, with an $IC_{50}$ of 1.8 nM (with a 95% confidence interval of 0.9-3.8 nM), confirming earlier observations that HRG1-beta signaling is mediated primarily by ErbB2/ErbB3 and not ErbB1/ErbB3 heterodimers. Pertuzumab (a monoclonal antibody that sterically hinders ErbB2's recruitment into ErbB ligand complexes) was able to inhibit HRG1-beta-induced ErbB3 phosphorylation, with an $IC_{50}$ of 3.6 nM (with a 95% confidence interval of 1.0-13.5 nM), but did not inhibit BTC-induced ErbB3 phosphorylation. Thus, Ab #6 was the only inhibitor tested that was capable of potently inhibiting ErbB3 phosphorylation with low nanomolar $IC_{50}$ values for both HRG1-beta and BTC stimulation.

Example 16

Combination Therapy with Ab #6 and Other Therapeutic Agents

In this example, the efficacy of Ab #6 in inhibiting tumor growth in xenograft tumor models was assessed in combination with other therapeutic agents, namely erlotinib or taxol.

Figure 31A:
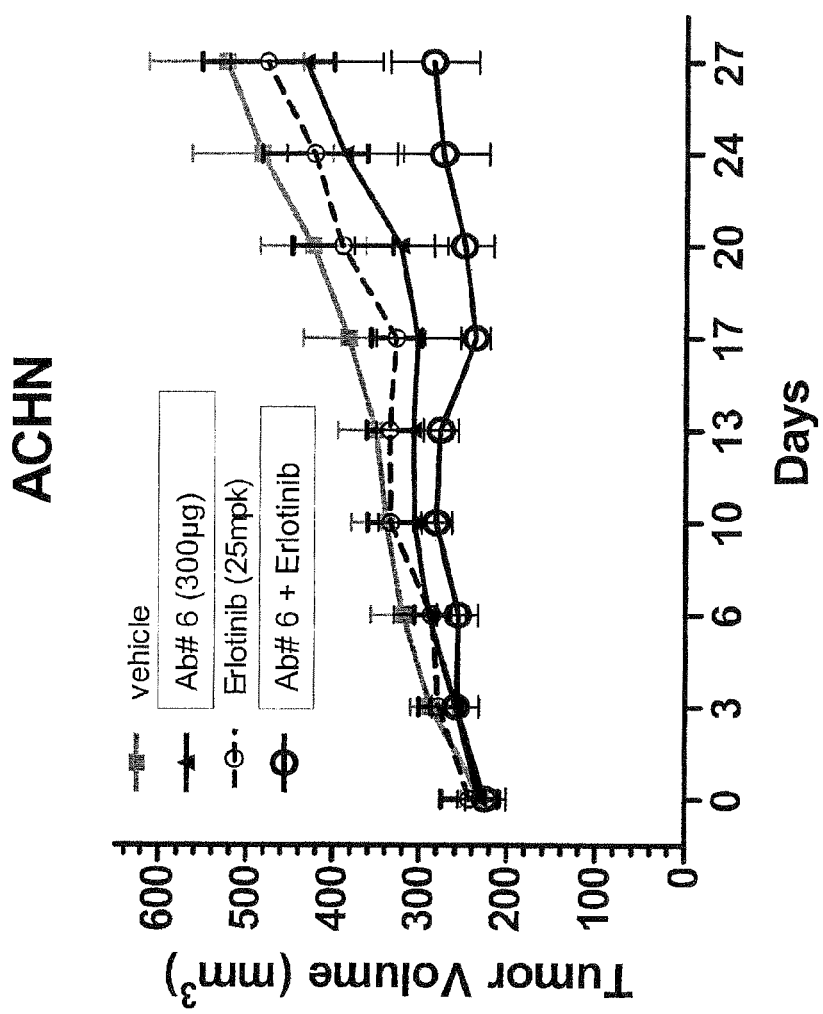
FIG. 31A is a graph showing the effect of Ab #6 alone, erlotinib alone or Ab #6 plus erlotinib on the growth of ACHN xenograft tumors in nude mice.

In a first experiment, mice bearing ACHN (a renal tumor cell line) xenograft tumors were prepared by establishing tumors in nude mice (Charles River Laboratories). The tumor-bearing mice were dosed intraperitoneally (IP) every three days with Ab #6 (300 μg) or vehicle. Erlotinib (25 mg/kg) was administered orally once daily, either alone or in combination with the Ab #6 treatment. Tumor size (length× width) was measured twice a week and measurements were used to calculate tumor volume (p/6 (L×W2). The results are shown in FIG. 31A, which demonstrates that while Ab #6 or erlotinib alone inhibited tumor growth, inhibition by the combination therapy (Ab #6 plus erlotinib) was greater than either single agent alone resulting in an additive effect.

Figure 31B:
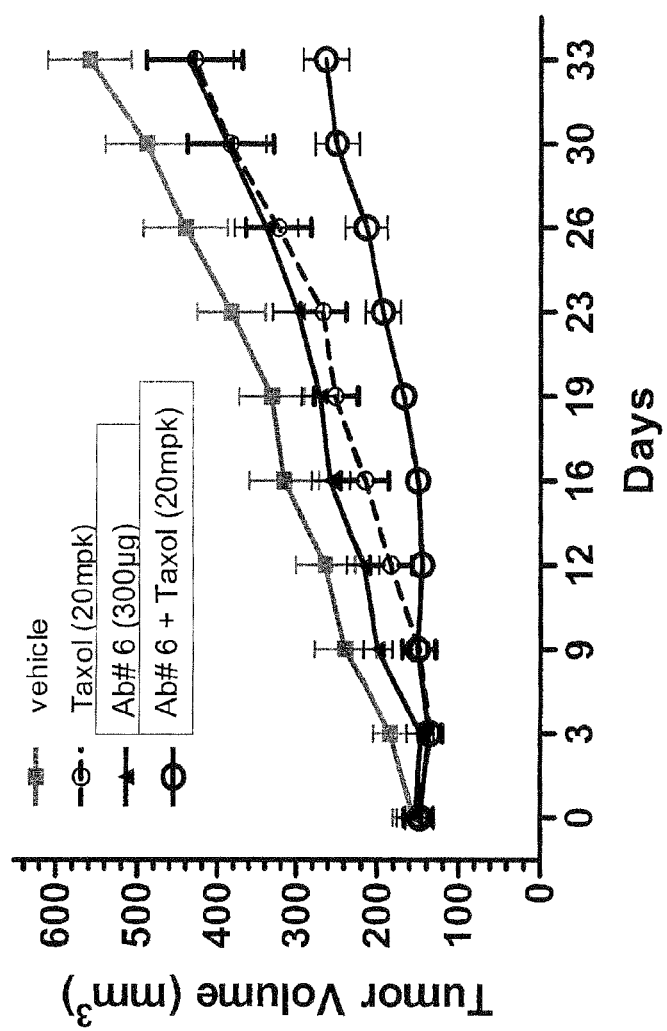
FIG. 31B is a graph showing the effect of Ab #6 alone, taxol alone or Ab #6 plus taxol on the growth of DU145 xenograft tumors in nude mice.

In a second experiment, mice bearing DU145 (a prostate tumor cell line) xenograft tumors were prepared by establishing tumors in nude mice (Charles River Laboratories). The tumor-bearing mice were dosed intraperitoneally (IP) every three days with Ab #6 (300 μg) or vehicle. Taxol (20 mg/kg) was administered IP once per week, either alone or in combination with the Ab #6 treatment. Again, tumor size was measured twice a week and measurements were used to calculate tumor volume. The results are shown in FIG. 31B, which again demonstrates that while Ab #6 or taxol alone inhibited tumor growth, inhibition by the combination therapy (Ab #6 plus taxol) was greater than either single agent alone resulting in an additive effect.

Example 17

Inhibition of Growth of KRAS Mutant Tumor Cells

In this example, the ability of Ab #6, either alone or in combination with other agents, to inhibit the growth of tumor cells that comprise a KRAS mutation was examined.

Figure 32A:
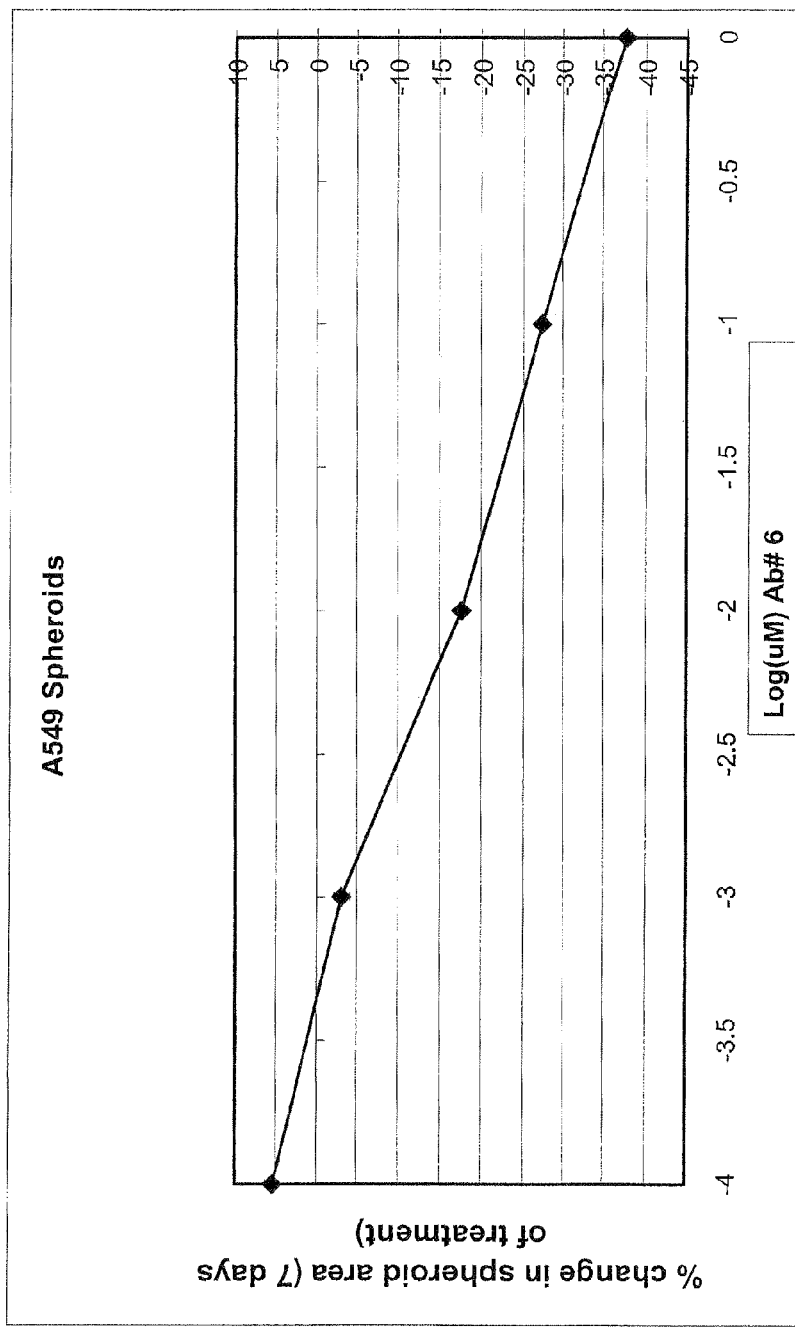
FIG. 32A is a graph showing the effect of Ab #6 treatment alone on the growth of multicellular tumor spheroids of KRAS mutant A549 lung cancer cells. Cells were treated with 0, 0.001, 0.01, 0.1 or 1 μM Ab #6 for seven days. The "−4" on the graph corresponds to the "0" dose.
Figure 32B:
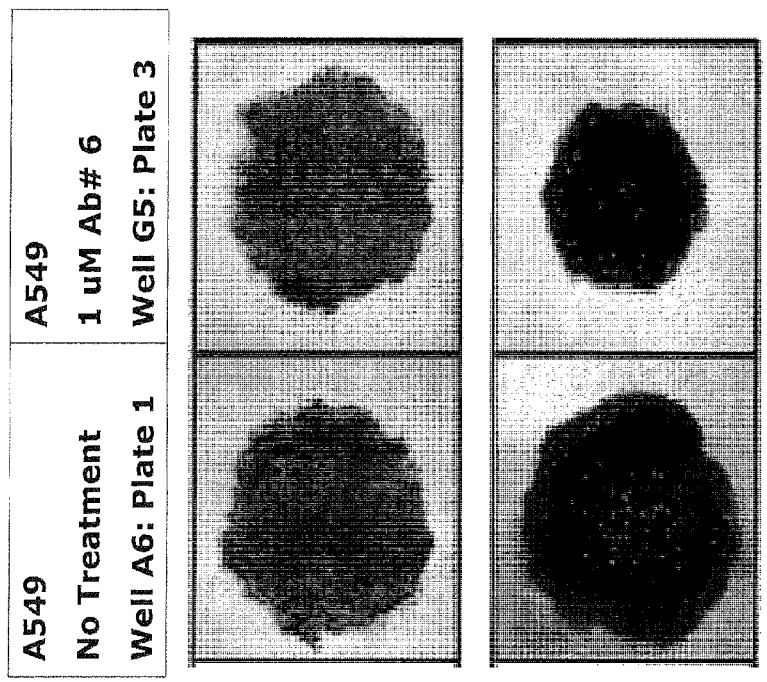
FIG. 32B is a set of photographs of representative A549 spheroids, either untreated or treated with 1 μM Ab #6, on day 1 and day 7 of treatment.

A549 is a lung cancer cell line that comprises a G12S KRAS mutation. This cell line is insensitive to treatment with erlotinib or taxol alone. To test the ability of Ab #6 alone to inhibit growth of A549 cells in vitro, the cells were grown as multicellular tumor spheroids (2000 cells/spheroid/well of a 96 well plate) and then treated with 0, 0.001, 0.01, 0.1 or 1 µM Ab #6 for seven days. The area of the spheroid was measured under 4× magnification using Metamorph software on day 1 and day 7 and the percent change in spheroid ara was calculated ((Initial Area−Final Area/Initial Area×100). The results are shown in the graph of FIG. 32A ("−4" on the graph corresponds to the "0" dose), which demonstrates that Ab #6 treatment alone was sufficient to inhibit the growth of the KRAS mutant A549 tumor cells in vitro. Photographs of representative spheroids are shown in FIG. 32B. Untreated spheroids grew approximately 5% in 7 days versus a 35% reduction in size of spheroids treated with 1 µM Ab #6.

Figure 32C:
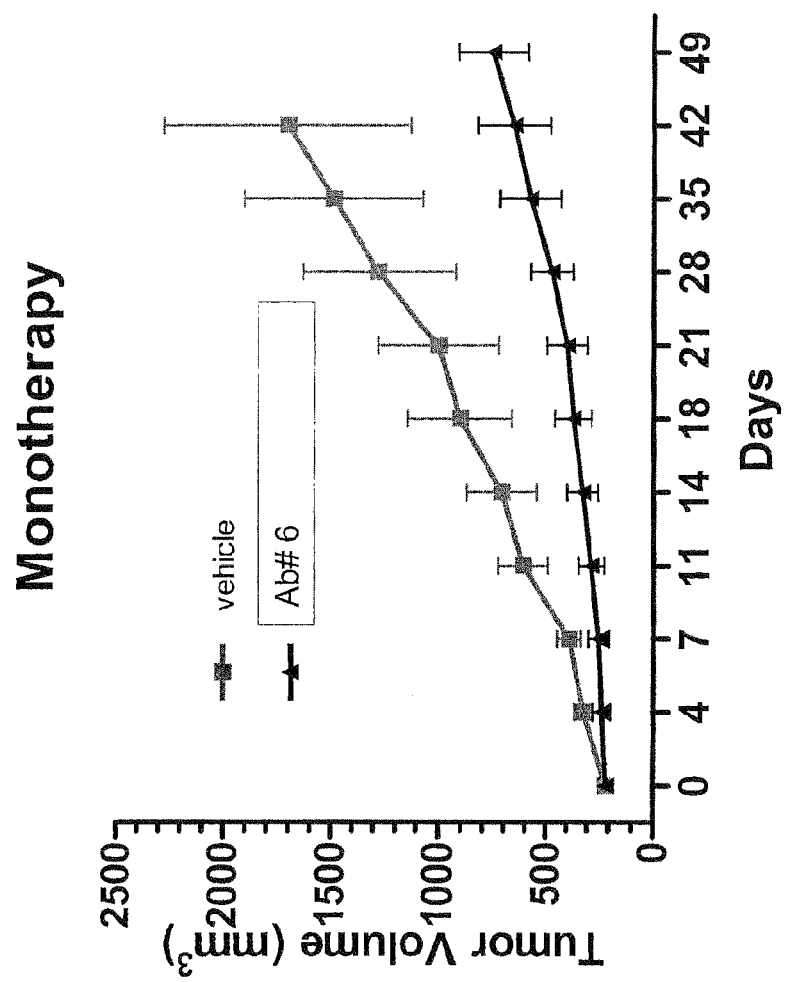
FIG. 32C is a graph showing the effect of Ab #6 treatment alone on the growth of KRAS mutant A549 subcutaneous xenograft tumors in nude mice. Dosing of Ab #6 (600 μg every three days) was stopped on day 22.

To test the ability of Ab #6 alone to inhibit the growth of the KRAS mutant A549 cells in vivo, nude mice bearing A549 subcutaneous xenograft tumors were treated with 600 µg of Ab #6 every three days, followed by measurement of tumor volume. The results are shown in the graph of FIG. 32C, which demonstrates significant tumor growth inhibition by Ab #6 treatment alone, which growth inhibition was retained after dosing stopped on day 22. Thus, Ab #6 alone is able to inhibit the growth of KRAS mutant tumor cells in vivo.

Figure 33A:
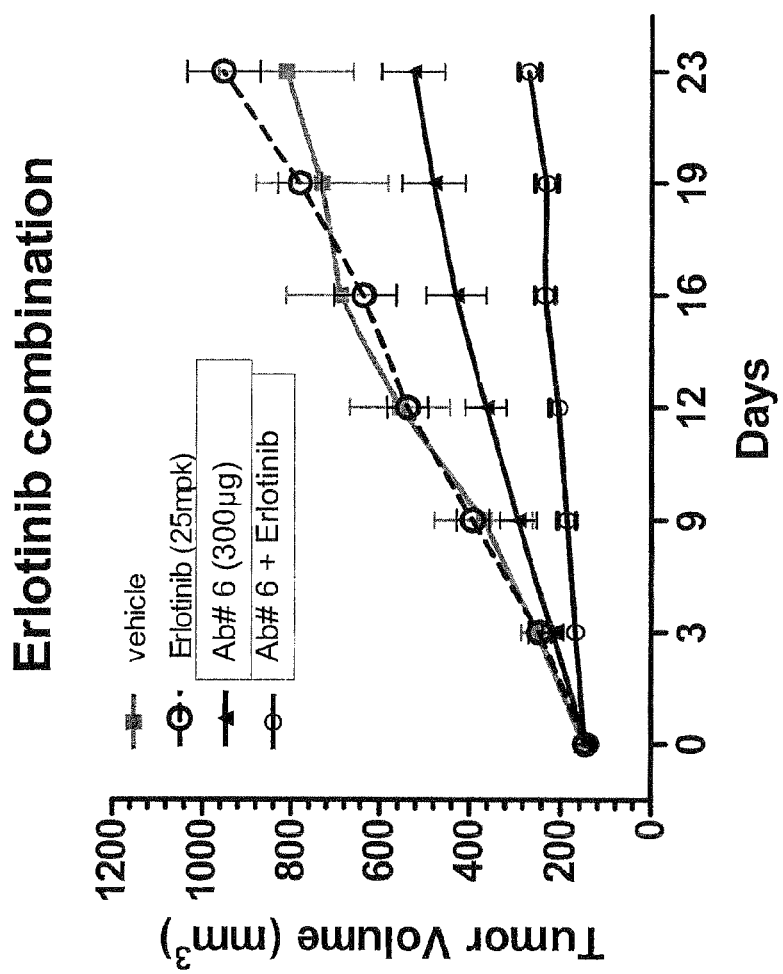
FIG. 33A is a graph showing the effect of Ab #6 treatment alone, erlotinib treatment alone or combined treatment with Ab #6 and erlotinib on the growth of KRAS mutant A549 subcutaneous xenograft tumors in nude mice.
Figure 33B:
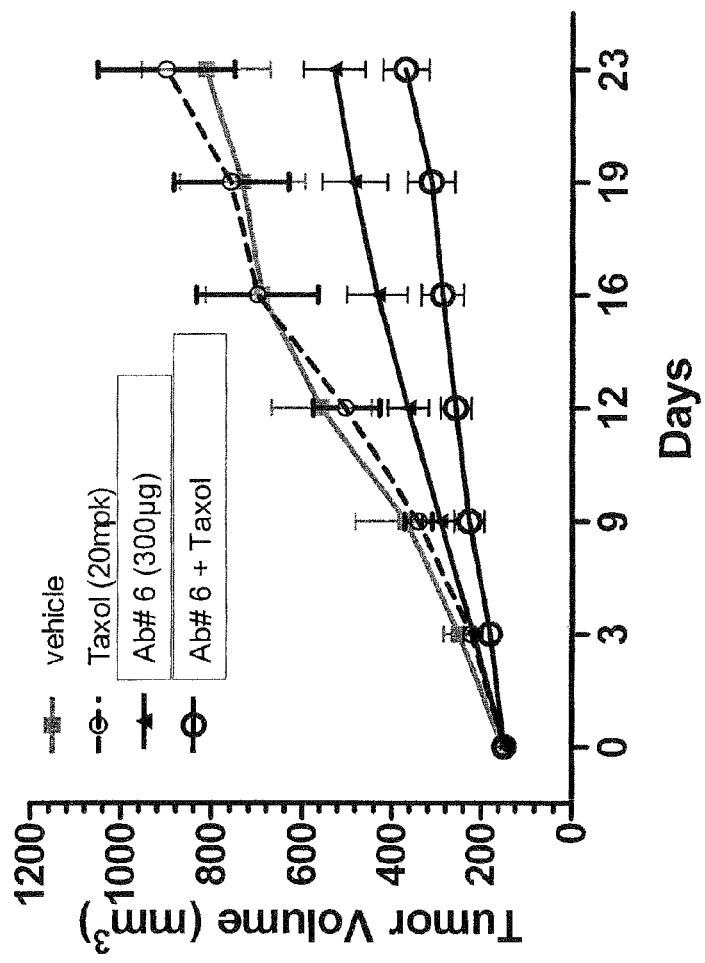
FIG. 33B is a graph showing the effect of Ab #6 treatment alone, taxol treatment alone or combined treatment with Ab #6 and taxol on the growth of KRAS mutant A549 subcutaneous xenograft tumors in nude mice.
Figure 34:
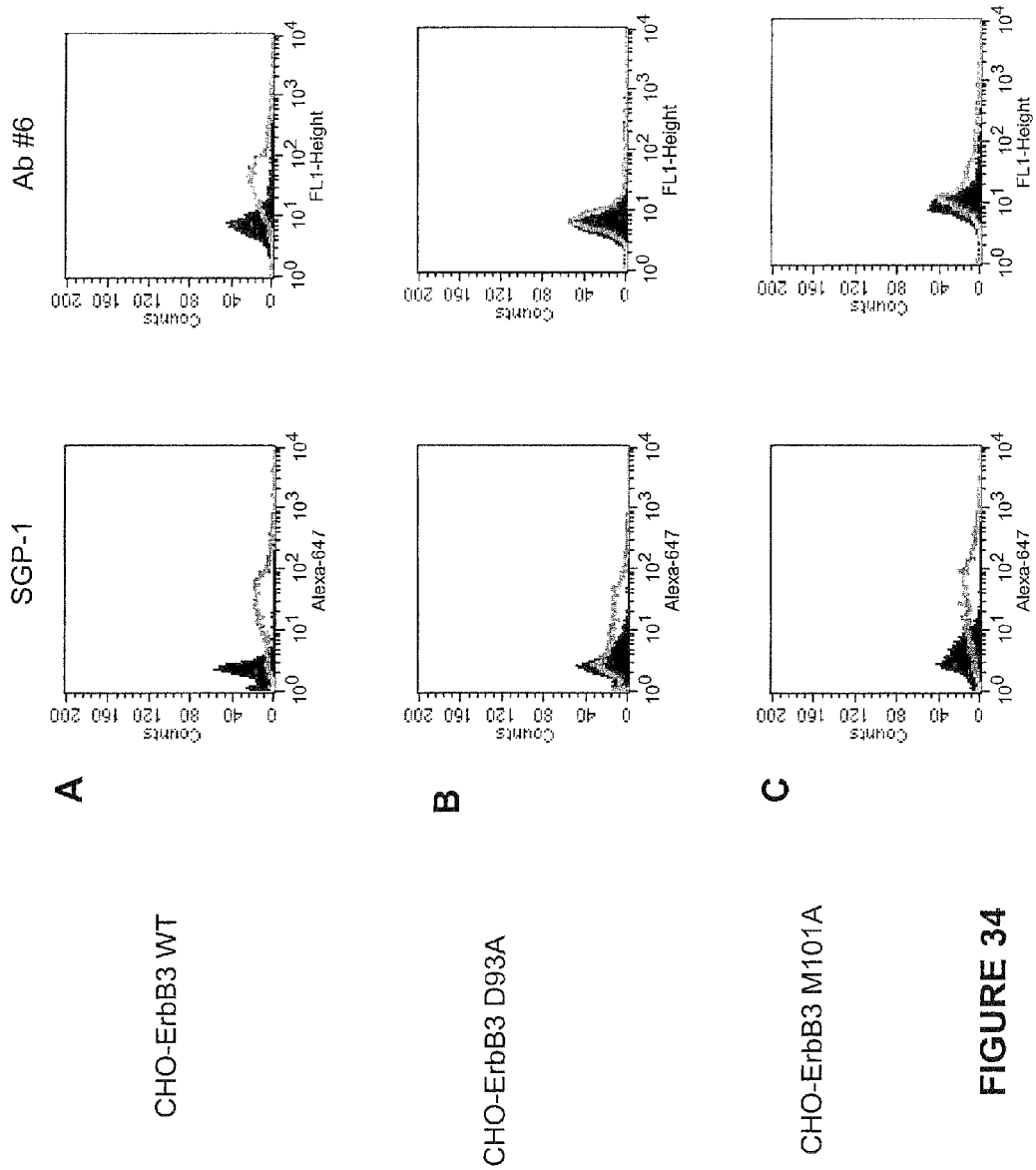
FIGS. 34A-34E shows the results of a FACS analysis for the binding of Ab #6 and a control anti-ErbB3 antibody (SGP1) to CHO cells expressing either wild-type ErbB3 (FIG. 34A) or CHO cells expressing ErbB3 having one of the following point mutations: D93A (FIG. 34B), M101A (FIG. 34C), L102A (FIG. 34D) or Y104A (FIG. 34E).
Figure 34:
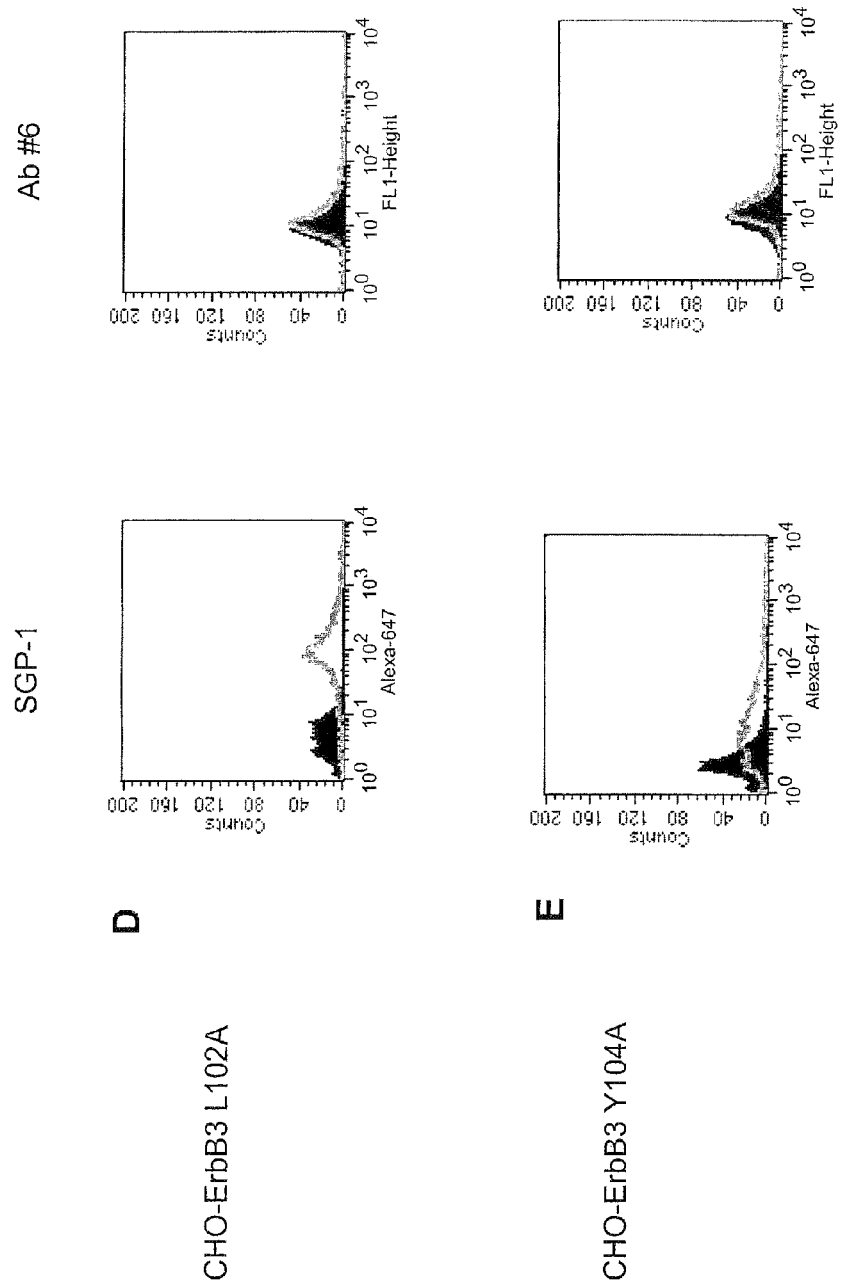

To test the ability of Ab #6 in combination with either erlotinib or taxol to inhibit the growth of the KRAS mutant A549 cells in vivo, nude mice bearing A549 subcutaneous xenograft tumors were treated with either: (i) 300 µg of Ab #6 alone every three day; (ii) 25 mg/kg erlotinib alone every day; (iii) 20 mg/kg taxol alone every 7 days; (iv) Ab #6 and erlotinib in combination (at the same dosing); or (v) Ab #6 and taxol in combination (at the same dosing). The results for the erlotinib experiment are shown in FIG. 33A. The results for the taxol experiment are shown in FIG. 33B. The results from both experiments demonstrate that the KRAS mutant A549 xenografts were insensitive to treatment with either erlotinib or taxol alone, that growth of the KRAS mutant xenografts was inhibited by Ab #6 treatment alone and that combining Ab #6 treatment with either erlotinib or taxol treatment led to even greater tumor growth inhibition that observed with Ab #6 monotherapy.

The ability of Ab #6 to inhibit the growth of tumor cells comprising a KRAS mutation was confirmed in experiments using a second cell line. The LS180 colon cancer cell line comprises a KRAS mutation in codon 12. Xenograft tumor experiments essentially the same as those described above for the A549 cell line were performed with the LS180 cell line. Tumor bearing mice were treated with Ab #6 at 750 µg/injection every three days. Similar to the results observed with the A549 cells, Ab #6 was able to inhibit the growth of LS180 cells in vivo in the xenograft tumor model, thereby demonstrating the ability of the antibody to inhibit the growth of a second KRAS mutant tumor cell line.

Example 18

Epitope Mapping of Ab #6 Binding to ErbB3

In this example, alanine scanning mutagenesis was used to map the epitope within ErbB3 to which Ab # binds.

Since Ab #6 was known to inhibit heregulin (HRG) binding to ErbB3, alanine mutagenesis focused on the predicted HRG binding site in the extracellular domain 1 of ErbB3. To assist in selection of which residues to mutate, the crystal structure of EGFR complexed with TGFα (Garret et al. (2002) *Cell* 110:763-773) was used, since the crystal structure of ErbB3 complexed with HRG is not available. ErbB3 and EGFR are homologous in structure and thus even if the interacting residues are not identical, the structural elements (certain loops or helix faces) should be the same. Accordingly, the residues in EGFR specified to be involved in ligand binding as described in Garret et al., supra, were identified and sequence alignment of ErbB3 and EGFR revealed the corresponding ErbB3 residues. In addition to the ligand binding sites, other faces of the ErbB3 extracellular domain 1 were mutated using the crystal structure of ErbB3 as a guide (Cho and Leahy (2002) *Science* 297:1330-1333).

Accordingly, the following ErbB3 point mutations were made: L14A, N15A, L17A, S18A, V19A, T20A, N25A, K32A, L33A, V47A, L48A, M72A, Y92A, D93A, M101A, L102A, Y104A, N105A, T106A, Y129A, K132A, Q59A, T77A, Q90A, Q114A, Q119A, R145A, R151A, V156A, H168A, K172A and L186A. Mutagenesis was accomplished using standard methods known in the art and the ErbB3 mutants, within the context of the ErbB3 domain 1, were expressed on the surface of yeast cells using standard methods known in the art. All mutants expressed well on the surface of the yeast at levels identical to those of the wild type ErbB3 domain 1. Expression of the ErbB3 domain 1 mutants on yeast allowed for the ability to examine binding of Ab #6 to the mutants using FACS without first purifying the recombinant proteins.

Binding of Ab #6 to the ErbB3 domain 1 mutants was determined by standard FACS analysis. A second anti-ErbB3 antibody (SGP1; LabVision), which has a non-overlapping epitope with Ab #6, was used as a control to ensure that the mutations were not just generally destabilizing the ErbB3 structure. Thus, mutations that affected the binding of both antibodies were excluded from further characterization. For FACS analysis, yeast cells expressing the different mutant version of ErbB3 domain 1 on their surface were labeled simultaneously with Ab #6 (followed by a goat anti-human Ab-Alexa 488 as secondary antibody) and with SGP1-Alexa 647. Four of the alanine point mutations were found to affect Ab #6 binding to the ErbB3 domain 1 while not affecting the binding of the control anti-ErbB3 antibody (SGP1): D93A, M101A, L102A and Y104A.

To further confirm that the Ab #6 epitope comprises residues 93, 101, 102 and 104 of ErbB3, these four mutants (D93A, M101A, L102A, Y104A), in the context of the full-length ErbB3 receptor, were transfected stably into CHO K1 cells in order to examine their effect within the context of the full length ErbB3. CHO K1 cells expressing wild type full-length ErbB3 served as a positive control. High expressing clones were selected for each mutant and labeled for standard FACS analysis either with Ab #6 or SGP1, another anti-ErbB3 antibody that has a non-overlapping epitope with Ab #6 (to confirm proper folding of ErbB3). SGP1 was directly labeled with Alexa 647 dye and Ab #6 was directly labeled with Alexa 488.

The results are shown in FIGS. 34A-34E, which show the binding of SGP1 or Ab #6 to wild type ErbB3, the D93A mutant, the M101A mutant, the L102A mutant or the Y104A mutant, respectively. The results demonstrate that the control anti-ErbB3 antibody (SGP1) was able to bind all four mutants, whereas Ab #6 displayed essentially no binding to three of the mutants (D93A, L102A and Y104A) and only very minimal binding to the fourth mutant (M101A). Thus, the full-length ErbB3 CHO cell expression experiments confirmed that the Ab #6 epitope on ErbB3 comprises residues 93, 101, 102 and 104. These four residue are located on strand 3 of a 5 stand parallel beta-sheet within ErbB3.

Example 19

Inhibition of Growth of PI3K Mutant Tumor Cells

In this example, the ability of Ab #6, either alone or in combination with another agent, to inhibit the growth of tumor cells that comprise a PI3K mutation was examined.

Figure 35A:
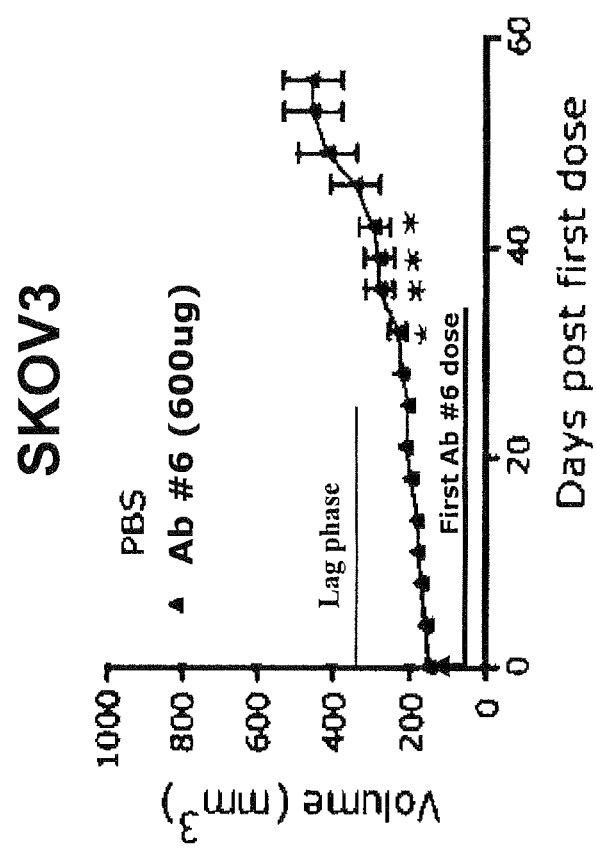
FIG. 35A is a graph showing the showing the effect of Ab #6 treatment alone on the growth of PI3K mutant SKOV3 xenograft tumors in mice.

SKOV3 is an ovarian cancer cell line that comprises a PI3K mutation. To test the ability of Ab #6 alone to inhibit the growth of the PI3K mutant SKOV3 cells in vivo, nude mice bearing SKOV3 subcutaneous xenograft tumors (tumor volume of 150-200 mm$^3$) were treated with 600 μg of Ab #6 every three days, followed by measurement of tumor volume. The results are shown in the graph of FIG. 35A, which demonstrates Ab #6 treatment alone resulted in partial tumor growth inhibition. In this experiment, a "lag phase" in tumor growth of approximately 30 days was observed even in the vehicle-treated mice, indicating that this tumor was slow to grow in vivo. Nevertheless, the decrease in the tumor volume after 30 days in the Ab #6 treated mice as compared to the vehicle treated mice demonstrates that Ab #6 treatment alone is able to inhibit the growth of PI3K mutant tumor cells in vivo.

Figure 35B:
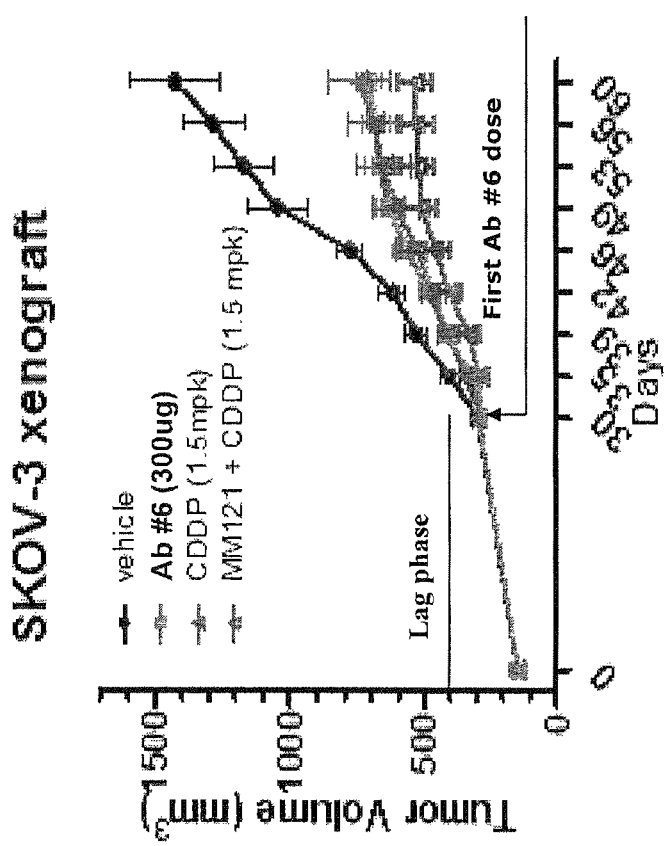
FIG. 35B is a graph showing the showing the effect of Ab #6 treatment alone, or in combination with cisplatin (CDDP), on the growth of PI3K mutant SKOV3 xenograft tumors in mice.

To test the ability of Ab #6 in combination with cisplatin to inhibit the growth of the PI3K mutant SKOV3 cells in vivo, nude mice bearing SKOV3 subcutaneous xenograft tumors were treated with either: (i) 300 μg of Ab #6 alone every three day (a suboptimal dose of Ab #6); (ii) 1.5 mg/kg cisplatin (CDDP) alone; or (iii) Ab #6 and cisplatin in combination (at the same dosing). Given the 30 day "lag phase" observed in the Ab #6 monotherapy experiment described above, dosing with Ab #6 in the combination experiment was not begun until after the 30 day lag phase had elapsed. The results for the combination therapy experiment are shown in FIG. 35B. The results demonstrate that both Ab #6 and cisplatin alone were able to inhibit the growth of the SKOV3 xenografts and that the combination treatment led to even greater tumor growth inhibition than either agent alone, thereby demonstrating the enhanced effectiveness of Ab #6 treatment when combined with a second therapeutic agent, such as cisplatin.

EQUIVALENTS

Those skilled in the art will recognize, or be able to ascertain using no more than routine experimentation, many equivalents of the specific embodiments of the invention described herein. Such equivalents are intended to be encompassed by the following claims. Any combination of the embodiments disclosed in the dependent claims are contemplated to be within the scope of the invention.

INCORPORATION BY REFERENCE

All publications, patents, and pending patent applications referred to herein are hereby incorporated by reference in their entirety.

We claim:

1. An isolated monoclonal antibody or antigen binding portion thereof that specifically binds to ErbB3 and comprises heavy chain variable region CDR1, CDR2, and CDR3 amino acid sequences as set forth in SEQ ID NOs: 7, 8, and 9, respectively, and light chain variable region CDR1, CDR2, and CDR3 amino acid sequences as set forth in SEQ ID NOs: 10, 11, and 12, respectively.

2. An isolated monoclonal antibody, or antigen binding portion thereof, that specifically binds to ErbB3 and comprises heavy and light chain variable regions as set forth in SEQ ID NOs: 1 and 2, respectively.

3. The monoclonal antibody, or antigen binding portion thereof, of claim 1 or 2, wherein the antibody, or antigen binding portion thereof, inhibits the migration of MCF-7 cells induced by fetal bovine serum.

4. The monoclonal antibody, or antigen binding portion thereof, of claim 3, wherein the monoclonal antibody, or antigen binding portion thereof, binds to ErbB3 with an affinity of $10^7$ to $10^{10}$ $M^{-1}$ as measured by a surface plasmon resonance assay or a cell binding assay.

5. The monoclonal antibody, or antigen binding portion thereof, of claim 4, wherein the affinity is an affinity of $5\times10^8$ to $10^{10}$ $M^{-1}$.

6. The monoclonal antibody, or antigen binding portion thereof, of claim 5 wherein the affinity is an affinity of about 4 nM.

7. The monoclonal antibody, or antigen binding portion thereof, of claim 1 or 2, wherein the antibody downregulates the ErbB3 receptor on MALME-3M cells, as measured using FACS analysis.

8. The monoclonal antibody, or antigen binding portion thereof, of claim 1 or 2, wherein the antibody inhibits proliferation of ACHN cells.

9. The monoclonal antibody, or antigen binding portion thereof, of claim 1 or 2, wherein the antibody inhibits VEGF secretion by heregulin-stimulated MCF-7 cells.

10. The monoclonal antibody or antigen binding portion thereof of claim 1 or 2, wherein the antibody or antigen binding portion thereof is a human or humanized antibody or antigen binding portion thereof.

11. The monoclonal antibody of claim 1 or 2, wherein the monoclonal antibody is a human or humanized antibody; or is an IgG1, an IgG2, an IgG3, an IgG4, an IgM, an IgA1, an IgA2, an IgAsec, an IgD, or an IgE isotype monoclonal antibody; or is a human or humanized IgG1, IgG2, IgG3, IgG4, IgM, IgA1, IgA2, IgAsec, IgD, or IgE isotype monoclonal antibody.

12. The monoclonal antibody of claim 1 or 2, wherein the antibody is a whole antibody.

13. A composition comprising the monoclonal antibody of claim 1 or 2 in a pharmaceutically acceptable carrier.

14. The composition of claim 13, wherein the composition is a sterile aqueous solution or dispersion suitable for injection or infusion, or the composition is a sterile powder for the extemporaneous preparation of a sterile injectable solution or dispersion suitable for injection or infusion.

15. A sterile aqueous pharmaceutical composition according to claim 13.

* * * * *

SEQUENCE LISTING

```
<160> NUMBER OF SEQ ID NOS: 53

<210> SEQ ID NO 1
<211> LENGTH: 119
<212> TYPE: PRT
<213> ORGANISM: Artificial Sequence
<220> FEATURE:
<223> OTHER INFORMATION: /note="Description of Artificial Sequence:
      Synthetic polypeptide"

<400> SEQUENCE: 1

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
            20                  25                  30

Val Met Ala Trp Val Arg Gln Ala Pro Gly Lys Gly Leu Glu Trp Val
        35                  40                  45

Ser Ser Ile Ser Ser Ser Gly Gly Trp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Leu Lys Met Ala Thr Ile Phe Asp Tyr Trp Gly Gln Gly
            100                 105                 110

Thr Leu Val Thr Val Ser Ser
        115

<210> SEQ ID NO 2
<211> LENGTH: 111
<212> TYPE: PRT
<213> ORGANISM: Artificial Sequence
<220> FEATURE:
<223> OTHER INFORMATION: /note="Description of Artificial Sequence:
      Synthetic polypeptide"
```

<400> SEQUENCE: 2

```
Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Ser Tyr
                 20                  25                  30

Asn Val Val Ser Trp Tyr Gln Gln His Pro Gly Lys Ala Pro Lys Leu
             35                  40                  45

Ile Ile Tyr Glu Val Ser Gln Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Thr Glu Asp Glu Ala Asp Tyr Tyr Cys Cys Ser Tyr Ala Gly Ser
                 85                  90                  95

Ser Ile Phe Val Ile Phe Gly Gly Gly Thr Lys Val Thr Val Leu
            100                 105                 110
```

<210> SEQ ID NO 3
<211> LENGTH: 118
<212> TYPE: PRT
<213> ORGANISM: Artificial Sequence
<220> FEATURE:
<223> OTHER INFORMATION: /note="Description of Artificial Sequence: Synthetic polypeptide"

<400> SEQUENCE: 3

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ala Tyr
                 20                  25                  30

Asn Met Arg Trp Val Arg Gln Ala Pro Gly Lys Gly Leu Glu Trp Val
             35                  40                  45

Ser Val Ile Tyr Pro Ser Gly Ala Thr Arg Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Tyr Tyr Tyr Gly Met Asp Val Trp Gly Gln Gly Thr
            100                 105                 110

Leu Val Thr Val Ser Ser
            115
```

<210> SEQ ID NO 4
<211> LENGTH: 110
<212> TYPE: PRT
<213> ORGANISM: Artificial Sequence
<220> FEATURE:
<223> OTHER INFORMATION: /note="Description of Artificial Sequence: Synthetic polypeptide"

<400> SEQUENCE: 4

```
Gln Ser Val Leu Thr Gln Pro Pro Ser Ala Ser Gly Thr Pro Gly Gln
  1               5                  10                  15

Arg Val Thr Ile Ser Cys Ser Gly Ser Asp Ser Asn Ile Gly Arg Asn
                 20                  25                  30

Tyr Ile Tyr Trp Tyr Gln Gln Phe Pro Gly Thr Ala Pro Lys Leu Leu
             35                  40                  45
```

Ile Tyr Arg Asn Asn Gln Arg Pro Ser Gly Val Pro Asp Arg Ile Ser
                 50                  55                  60

Gly Ser Lys Ser Gly Thr Ser Ala Ser Leu Ala Ile Ser Gly Leu Arg
 65                  70                  75                  80

Ser Glu Asp Glu Ala Glu Tyr His Cys Gly Thr Trp Asp Asp Ser Leu
                 85                  90                  95

Ser Gly Pro Val Phe Gly Gly Gly Thr Lys Leu Thr Val Leu
            100                 105                 110

<210> SEQ ID NO 5
<211> LENGTH: 122
<212> TYPE: PRT
<213> ORGANISM: Artificial Sequence
<220> FEATURE:
<223> OTHER INFORMATION: /note="Description of Artificial Sequence:
      Synthetic polypeptide"

<400> SEQUENCE: 5

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ala Tyr
             20                  25                  30

Gly Met Gly Trp Val Arg Gln Ala Pro Gly Lys Gly Leu Glu Trp Val
         35                  40                  45

Ser Tyr Ile Ser Pro Ser Gly His Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Leu Glu Thr Gly Leu Leu Val Asp Ala Phe Asp Ile Trp
            100                 105                 110

Gly Gln Gly Thr Met Val Thr Val Ser Ser
            115                 120

<210> SEQ ID NO 6
<211> LENGTH: 106
<212> TYPE: PRT
<213> ORGANISM: Artificial Sequence
<220> FEATURE:
<223> OTHER INFORMATION: /note="Description of Artificial Sequence:
      Synthetic polypeptide"

<400> SEQUENCE: 6

Gln Tyr Glu Leu Thr Gln Pro Pro Ser Val Ser Val Tyr Pro Gly Gln
 1               5                  10                  15

Thr Ala Ser Ile Thr Cys Ser Gly Asp Gln Leu Gly Ser Lys Phe Val
             20                  25                  30

Ser Trp Tyr Gln Gln Arg Pro Gly Gln Ser Pro Val Leu Val Met Tyr
         35                  40                  45

Lys Asp Lys Arg Arg Pro Ser Glu Ile Pro Glu Arg Phe Ser Gly Ser
 50                  55                  60

Asn Ser Gly Asn Thr Ala Thr Leu Thr Ile Ser Gly Thr Gln Ala Ile
 65                  70                  75                  80

Asp Glu Ala Asp Tyr Tyr Cys Gln Ala Trp Asp Ser Ser Thr Tyr Val
                 85                  90                  95

Phe Gly Thr Gly Thr Lys Val Thr Val Leu
            100                 105

```
<210> SEQ ID NO 7
<211> LENGTH: 5
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 7

His Tyr Val Met Ala
  1               5

<210> SEQ ID NO 8
<211> LENGTH: 17
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 8

Ser Ile Ser Ser Ser Gly Gly Trp Thr Leu Tyr Ala Asp Ser Val Lys
  1               5                  10                  15

Gly

<210> SEQ ID NO 9
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 9

Gly Leu Lys Met Ala Thr Ile Phe Asp Tyr
  1               5                  10

<210> SEQ ID NO 10
<211> LENGTH: 14
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 10

Thr Gly Thr Ser Ser Asp Val Gly Ser Tyr Asn Val Val Ser
  1               5                  10

<210> SEQ ID NO 11
<211> LENGTH: 7
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 11

Glu Val Ser Gln Arg Pro Ser
  1               5

<210> SEQ ID NO 12
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"
```

```
<400> SEQUENCE: 12

Cys Ser Tyr Ala Gly Ser Ser Ile Phe Val Ile
  1               5                  10

<210> SEQ ID NO 13
<211> LENGTH: 5
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 13

Ala Tyr Asn Met Arg
  1               5

<210> SEQ ID NO 14
<211> LENGTH: 17
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 14

Val Ile Tyr Pro Ser Gly Gly Ala Thr Arg Tyr Ala Asp Ser Val Lys
  1               5                  10                  15

Gly

<210> SEQ ID NO 15
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 15

Gly Tyr Tyr Tyr Tyr Gly Met Asp Val
  1               5

<210> SEQ ID NO 16
<211> LENGTH: 13
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 16

Ser Gly Ser Asp Ser Asn Ile Gly Arg Asn Tyr Ile Tyr
  1               5                  10

<210> SEQ ID NO 17
<211> LENGTH: 7
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 17

Arg Asn Asn Gln Arg Pro Ser
  1               5
```

```
<210> SEQ ID NO 18
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 18

Gly Thr Trp Asp Asp Ser Leu Ser Gly Pro Val
 1               5                  10

<210> SEQ ID NO 19
<211> LENGTH: 5
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 19

Ala Tyr Gly Met Gly
 1               5

<210> SEQ ID NO 20
<211> LENGTH: 17
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 20

Tyr Ile Ser Pro Ser Gly Gly His Thr Lys Tyr Ala Asp Ser Val Lys
 1               5                  10                  15

Gly

<210> SEQ ID NO 21
<211> LENGTH: 13
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 21

Val Leu Glu Thr Gly Leu Leu Val Asp Ala Phe Asp Ile
 1               5                  10

<210> SEQ ID NO 22
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 22

Ser Gly Asp Gln Leu Gly Ser Lys Phe Val Ser
 1               5                  10

<210> SEQ ID NO 23
<211> LENGTH: 8
<212> TYPE: PRT
<213> ORGANISM: Artificial Sequence
<220> FEATURE:
<223> OTHER INFORMATION: /note="Description of Artificial Sequence:
      Synthetic peptide"
```

<400> SEQUENCE: 23

Tyr Lys Asp Lys Arg Arg Pro Ser
 1               5

<210> SEQ ID NO 24
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 24

Gln Ala Trp Asp Ser Ser Thr Tyr Val
 1               5

<210> SEQ ID NO 25
<211> LENGTH: 357
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 25

| | | |
|---|---|---|
| gaggtgcagc tgctggagag cggcggaggg ctggtccagc caggcggcag cctgaggctg | 60 |
| tcctgcgccg ccagcggctt caccttcagc cactacgtga tggcctgggt gcggcaggcc | 120 |
| ccaggcaagg gcctggaatg ggtgtccagc atcagcagca gcggcggctg daccctgtac | 180 |
| gccgacagcg tgaagggcag gttcaccatc agcagggaca cagcaagaa caccctgtac | 240 |
| ctgcagatga acagcctgag ggccgaggac accgccgtgt actactgcac caggggcctg | 300 |
| aagatggcca ccatcttcga ctactgggc cagggcaccc tggtgaccgt gagcagc | 357 |

<210> SEQ ID NO 26
<211> LENGTH: 333
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 26

| | | |
|---|---|---|
| cagtccgccc tgacccagcc cgccagcgtg agcggcagcc caggccagag catcaccatc | 60 |
| agctgcaccg gcaccagcag cgacgtgggc agctacaacg tggtgtcctg gtatcagcag | 120 |
| caccccggca aggcccccaa gctgatcatc tacgaggtgt cccagaggcc cagcggcgtg | 180 |
| agcaacaggt tcagcggcag caagagcggc aacaccgcca gcctgaccat cagcggcctg | 240 |
| cagaccgagg acgaggccga ctactactgc tgcagctacg ccggcagcag catcttcgtg | 300 |
| atcttcggcg gagggaccaa ggtgaccgtc cta | 333 |

<210> SEQ ID NO 27
<211> LENGTH: 354
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 27

| | | |
|---|---|---|
| gaggtgcagc tgctggaaag cggcggaggg ctggtgcagc caggcggcag cctgaggctg | 60 |
| tcctgcgccg ccagcggctt caccttcagc gcctacaaca tgagatgggt gcggcaggcc | 120 |

```
ccaggcaagg gcctggaatg ggtgtccgtg atctacccca gcggcggagc caccagatac    180
gccgacagcg tgaagggcag gttcaccatc agcagggaca acagcaagaa cacccctgtac    240 ctgcagatga acagcctgag ggccgaggac accgccgtgt actactgcgc caggggctac    300
tactactacg gcatggacgt gtggggccag ggcaccctgg tgaccgtgag cagc           354

<210> SEQ ID NO 28
<211> LENGTH: 330
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 28
cagagcgtgc tgacccagcc cccaagcgcc agcggcaccc caggccagag ggtgaccatc     60
agctgcagcg gcagcgacag caacatcggc aggaactaca tctactggta tcagcagttc    120
cccggcaccg cccccaagct gctgatctac aggaacaacc agaggcccag cggcgtgccc    180
gacaggatca gcggcagcaa gagcggcacc agcgccagcc tggccatcag cggcctgaga    240
agcgaggacg aggccgagta ccactgcggc acctgggacg acagcctgag cggcccagtg    300
ttcggcggag ggaccaagct gaccgtccta                                      330

<210> SEQ ID NO 29
<211> LENGTH: 366
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 29
gaagttcaat tgttagagtc tggtggcggt cttgttcagc ctggtggttc tttacgtctt     60
tcttgcgctg cttccggatt cactttctct gcttacggta tgggttgggt tcgccaagct    120
cctggtaaag gtttggagtg gtttcttat atctctcctt ctggtggcca tactaagtat    180
gctgactccg ttaaaggtcg cttcactatc tctagagaca actctaagaa tactctctac    240
ttgcagatga acagcttaag ggctgaggac acggccgtat attactgtgc gaaagtactg    300
gaaactggct tattggttga tgcttttgat atctggggcc aagggacaat ggtcaccgtc    360
tcaagc                                                                366

<210> SEQ ID NO 30
<211> LENGTH: 318
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 30
cagtacgaat tgactcagcc accctcagtg tccgtgtacc caggacagac agccagcatc     60
acctgctctg gagatcaatt ggggagtaaa tttgtttcct ggtatcagca gaggccaggc    120
cagtcccctg tgttggtcat gtataaagat aaaaggcggc cgtcagagat ccctgagcga    180
ttctctggct ccaactctgg gaacacagcc actctgacca tcagcgggac ccaggctata    240
gatgaggctg actattattg tcaggcgtgg gacagcagca cttatgtctt cggcactggg    300
accaaggtca ccgtccta                                                   318
```

<210> SEQ ID NO 31
<211> LENGTH: 357
<212> TYPE: DNA
<213> ORGANISM: Artificial Sequence
<220> FEATURE:
<223> OTHER INFORMATION: /note="Description of Artificial Sequence: Synthetic polynucleotide"

<400> SEQUENCE: 31

```
gaagttcaat tgttagagtc tggtggcggt cttgttcagc ctggtggttc tttacgtctt      60
tcttgcgctg cttccggatt cactttctct cattacgtta tggcttgggt tcgccaagct     120
cctggtaaag gtttggagtg gtttcttcct atctcttctt ctggtggctg gactctttat     180
gctgactccg ttaaaggtcg cttcactatc tctagagaca actctaagaa tactctctac     240
ttgcagatga acagcttaag ggctgaggac acagccgtgt attactgtac tagaggtctc     300
aagatggcta caattttttga ctactggggc cagggcaccc tggtcaccgt ctcaagc       357
```

<210> SEQ ID NO 32
<211> LENGTH: 333
<212> TYPE: DNA
<213> ORGANISM: Artificial Sequence
<220> FEATURE:
<223> OTHER INFORMATION: /note="Description of Artificial Sequence: Synthetic polynucleotide"

<400> SEQUENCE: 32

```
cagagcgctt tgactcagcc tgcctccgtg tctgggtctc ctggacagtc gatcaccatc      60
tcctgcactg gaaccagcag tgatgttggg agttataatg ttgtctcctg gtaccaacaa     120
cacccaggca aagcccccaa actcatcatt tatgaggtca gtcagcggcc ctcagggqtt     180 tctaatcgct tctctggctc caagtctggc aacacggcct ccctgacaat ctctgggctc     240
cagactgagg acgaggctga ttattactgc tgctcatatg caggtagtag tatttttcgtg     300 atattcggcg gagggaccaa ggtgaccgtc cta                                  333
```

<210> SEQ ID NO 33
<211> LENGTH: 354
<212> TYPE: DNA
<213> ORGANISM: Artificial Sequence
<220> FEATURE:
<223> OTHER INFORMATION: /note="Description of Artificial Sequence: Synthetic polynucleotide"

<400> SEQUENCE: 33

```
gaagttcaat tgttagagtc tggtggcggt cttgttcagc ctggtggttc tttacgtctt      60
tcttgcgctg cttccggatt cactttctct gcttacaata tgcgttgggt tcgccaagct     120
cctggtaaag gtttggagtg gtttctgtt atctatcctt ctggtggcgc tactcgttat      180
gctgactccg ttaaaggtcg cttcactatc tctagagaca actctaagaa tactctctac     240
ttgcagatga acagcttaag ggctgaggac acggccgtgt attactgtgc gagagggtac     300
tactactacg gtatggacgt ctggggccaa ggcaccctgg tcaccgtctc aagc           354
```

<210> SEQ ID NO 34
<211> LENGTH: 330
<212> TYPE: DNA
<213> ORGANISM: Artificial Sequence
<220> FEATURE:
<223> OTHER INFORMATION: /note="Description of Artificial Sequence: Synthetic polynucleotide"

<400> SEQUENCE: 34

```
cagagcgtct tgactcagcc accctcagcg tctgggaccc ccgggcagag ggtcaccatc    60
tcgtgttctg gaagcgactc caacatcgga agaaattata tatattggta ccagcaattc   120
ccaggaacgg ccccccaagct cctcatctat aggaataatc agcggccctc aggggtccct   180
gaccgaatct ctggctccaa gtctggcacc tcagcctccc tggccatcag tgggctccgg   240
tccgaggatg aggctgagta tcactgtgga acatgggatg acagcctgag tggtccggta   300
ttcggcggag ggactaagct gaccgtccta                                     330
```

<210> SEQ ID NO 35
<211> LENGTH: 118
<212> TYPE: PRT
<213> ORGANISM: Artificial Sequence
<220> FEATURE:
<223> OTHER INFORMATION: /note="Description of Artificial Sequence: Synthetic polypeptide"

<400> SEQUENCE: 35

```
Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Ser Trp Tyr
             20                  25                  30
Gly Met Gly Trp Val Arg Gln Ala Pro Gly Lys Gly Leu Glu Trp Val
         35                  40                  45
Ser Tyr Ile Ser Pro Ser Gly Gly Ile Thr Val Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Leu Asn Tyr Tyr Tyr Gly Leu Asp Val Trp Gly Gln Gly Thr
            100                 105                 110
Thr Val Thr Val Ser Ser
        115
```

<210> SEQ ID NO 36
<211> LENGTH: 108
<212> TYPE: PRT
<213> ORGANISM: Artificial Sequence
<220> FEATURE:
<223> OTHER INFORMATION: /note="Description of Artificial Sequence: Synthetic polypeptide"

<400> SEQUENCE: 36

```
Gln Asp Ile Gln Met Thr Gln Ser Pro Ser Ser Leu Ser Ala Ser Val
  1               5                  10                  15
Gly Asp Arg Ile Thr Ile Thr Cys Gln Ala Ser Gln Asp Ile Gly Asp
             20                  25                  30
Ser Leu Asn Trp Tyr Gln Gln Lys Pro Gly Lys Ala Pro Arg Leu Leu
         35                  40                  45
Ile Tyr Asp Ala Ser Asn Leu Glu Thr Gly Val Pro Pro Arg Phe Ser
     50                  55                  60
Gly Ser Gly Ser Gly Thr Asp Phe Thr Phe Thr Phe Arg Ser Leu Gln
 65                  70                  75                  80
```

```
Pro Glu Asp Ile Ala Thr Tyr Phe Cys Gln Gln Ser Ala Asn Ala Pro
                85                  90                  95

Phe Thr Phe Gly Pro Gly Thr Lys Val Asp Ile Lys
            100                 105

<210> SEQ ID NO 37
<211> LENGTH: 119
<212> TYPE: PRT
<213> ORGANISM: Artificial Sequence
<220> FEATURE:
<223> OTHER INFORMATION: /note="Description of Artificial Sequence:
      Synthetic polypeptide"

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Trp Trp Val Arg Gln Ala Pro Gly Lys Gly Leu Glu Trp Val
        35                  40                  45

Ser Tyr Ile Gly Ser Ser Gly Gly Pro Thr Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Arg Gly Thr Pro Tyr Tyr Phe Asp Ser Trp Gly Gln Gly
            100                 105                 110

Thr Leu Val Thr Val Ser Ser
        115

<210> SEQ ID NO 38
<211> LENGTH: 110
<212> TYPE: PRT
<213> ORGANISM: Artificial Sequence
<220> FEATURE:
<223> OTHER INFORMATION: /note="Description of Artificial Sequence:
      Synthetic polypeptide"

<400> SEQUENCE: 38

Gln Tyr Glu Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Arg Trp
            20                  25                  30

Asn Ile Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
            100                 105                 110

<210> SEQ ID NO 39
<211> LENGTH: 5
<212> TYPE: PRT
<213> ORGANISM: Artificial Sequence
```

<220> FEATURE:
<223> OTHER INFORMATION: /note="Description of Artificial Sequence:
      Synthetic peptide"

<400> SEQUENCE: 39

Trp Tyr Gly Met Gly
 1               5

<210> SEQ ID NO 40
<211> LENGTH: 17
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 40

Tyr Ile Ser Pro Ser Gly Gly Ile Thr Val Tyr Ala Asp Ser Val Lys
 1               5                  10                  15

Gly

<210> SEQ ID NO 41
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 41

Leu Asn Tyr Tyr Tyr Gly Leu Asp Val
 1               5

<210> SEQ ID NO 42
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 42

Gln Ala Ser Gln Asp Ile Gly Asp Ser Leu Asn
 1               5                  10

<210> SEQ ID NO 43
<211> LENGTH: 7
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 43

Asp Ala Ser Asn Leu Glu Thr
 1               5

<210> SEQ ID NO 44
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide"

```
<400> SEQUENCE: 44

Gln Gln Ser Ala Asn Ala Pro Phe Thr
  1               5

<210> SEQ ID NO 45
<211> LENGTH: 5
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 45

Arg Tyr Gly Met Trp
  1               5

<210> SEQ ID NO 46
<211> LENGTH: 17
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 46

Tyr Ile Gly Ser Ser Gly Gly Pro Thr Tyr Tyr Val Asp Ser Val Lys
  1               5                  10                  15

Gly

<210> SEQ ID NO 47
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 47

Gly Arg Gly Thr Pro Tyr Tyr Phe Asp Ser
  1               5                  10

<210> SEQ ID NO 48
<211> LENGTH: 14
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 48

Thr Gly Thr Ser Ser Asp Ile Gly Arg Trp Asn Ile Val Ser
  1               5                  10

<210> SEQ ID NO 49
<211> LENGTH: 7
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 49

Asp Val Ser Asn Arg Pro Ser
  1               5
```

```
<210> SEQ ID NO 50
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 50

Ser Ser Tyr Thr Ser Ser Ser Thr Trp Val
 1               5                  10

<210> SEQ ID NO 51
<211> LENGTH: 111
<212> TYPE: PRT
<213> ORGANISM: Artificial Sequence
<220> FEATURE:
<223> OTHER INFORMATION: /note="Description of Artificial Sequence:
      Synthetic polypeptide"

<400> SEQUENCE: 51

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
             20                  25                  30

Asn Val Val Ser Trp Tyr Gln Gln His Pro Gly Lys Ala Pro Lys Leu
         35                  40                  45

Met Ile Tyr Glu Val Ser Lys Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Ser Ile Phe Val Ile Phe Gly Gly Gly Thr Lys Val Thr Val Leu
            100                 105                 110

<210> SEQ ID NO 52
<211> LENGTH: 108
<212> TYPE: PRT
<213> ORGANISM: Artificial Sequence
<220> FEATURE:
<223> OTHER INFORMATION: /note="Description of Artificial Sequence:
      Synthetic polypeptide"

<400> SEQUENCE: 52

Gln Asp Ile Gln Met Thr Gln Ser Pro Ser Ser Leu Ser Ala Ser Val
 1               5                  10                  15

Gly Asp Arg Ile Thr Ile Thr Cys Gln Ala Ser Gln Asp Ile Gly Asp
             20                  25                  30

Ser Leu Asn Trp Tyr Gln Gln Lys Pro Gly Lys Ala Pro Arg Leu Leu
         35                  40                  45

Ile Tyr Asp Ala Ser Asn Leu Glu Thr Gly Val Pro Pro Arg Phe Ser
     50                  55                  60

Gly Ser Gly Ser Gly Thr Asp Phe Thr Phe Thr Phe Arg Ser Leu Gln
 65                  70                  75                  80

Pro Glu Asp Ile Ala Thr Tyr Phe Cys Gln Gln Ser Ala Asn Ala Pro
                 85                  90                  95

Phe Thr Phe Gly Pro Gly Thr Lys Val Asp Ile Arg
            100                 105
```

```
<210> SEQ ID NO 53
<211> LENGTH: 110
<212> TYPE: PRT
<213> ORGANISM: Artificial Sequence
<220> FEATURE:
<223> OTHER INFORMATION: /note="Description of Artificial Sequence:
      Synthetic polypeptide"

<400> SEQUENCE: 53

Gln Tyr Glu Leu Thr Gln Pro Ala Ser Val Ser Gly Ser Pro Gly Gln
 1               5                  10                  15

Ser Ile Thr Ile Ser Cys Thr Gly Thr Ser Ser Asp Ile Gly Arg Trp
            20                  25                  30

Asn Ile Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Val Val Phe Gly Gly Gly Thr Lys Leu Thr Val Leu
            100                 105                 110
```